US010465200B2

(12) United States Patent
Chittoor et al.

(10) Patent No.: US 10,465,200 B2
(45) Date of Patent: Nov. 5, 2019

(54) **PLANT REGULATORY ELEMENTS DERIVED FROM *MEDICAGO TRUNCATULA* 3'UTR SEQUENCES, AND USES THEREOF**

(71) Applicant: MONSANTO TECHNOLOGY, LLC, St. Louis, MO (US)

(72) Inventors: Jaishree M. Chittoor, Wildwood, MO (US); Amy J. Miyamoto, Belleville, WI (US); Amy M. Nichols, Mt. Horeb, WI (US); Mohammed Oufattole, Wildwood, MO (US); Michael W. Petersen, Sauk City, WI (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/882,957

(22) Filed: Jan. 29, 2018

(65) Prior Publication Data

US 2018/0230478 A1  Aug. 16, 2018

Related U.S. Application Data

(62) Division of application No. 14/949,694, filed on Nov. 23, 2015, now Pat. No. 9,938,535, which is a division of application No. 14/205,251, filed on Mar. 11, 2014, now Pat. No. 9,222,099.

(60) Provisional application No. 61/785,268, filed on Mar. 14, 2013.

(51) Int. Cl.
*C12N 15/82* (2006.01)

(52) U.S. Cl.
CPC ..... *C12N 15/8216* (2013.01); *C12N 15/8241* (2013.01); *C12N 15/8261* (2013.01); *C12N 15/8274* (2013.01); *C12N 15/8279* (2013.01)

(58) Field of Classification Search
None
See application file for complete search history.

(56) References Cited

U.S. PATENT DOCUMENTS

| | | | |
|---|---|---|---|
| 6,255,560 B1 | 7/2001 | Fraley et al. | |
| 7,534,932 B2 | 5/2009 | Harrison et al. | |
| 2005/0233346 A1* | 10/2005 | Dixon | C07K 14/415 435/6.12 |
| 2010/0017913 A1 | 1/2010 | Uppalapati | |
| 2016/0076047 A1 | 3/2016 | Chittoor et al. | |
| 2016/0083740 A1 | 3/2016 | Chittoor et al. | |
| 2018/0230479 A1 | 8/2018 | Chittoor et al. | |

FOREIGN PATENT DOCUMENTS

| WO | 2007078599 A2 | 7/2007 |
|---|---|---|
| WO | WO 2010/143138 | 12/2010 |
| WO | WO 2011/088299 | 7/2011 |

OTHER PUBLICATIONS

Medicago truncatula clone mth2-16g15, GenBank accession No. AC122162.32, published Sep. 17, 2010.*
Tong et al., 2012, J. Exp. Zool. 3188: 531-544.*
Wang et al., 2010, Proceedings of the National Academy of Sciences USA 107: 22338-22343, with supporting information.*
Pesole et al., 2000, The untranslated regions of eukaryotic mRNAs: Structure, function, evolution and bioinformatic tools for their analysis, Briefings in Bioinformatics 1: 236-249.*
Mignone and Pesole, 2011, "mRNA Untranslated Regions(UTRs)", In: eLS, John Wiley & Sons, pp. 1-5.*
U.S. Appl. No. 14/949,690, filed Nov. 23, 2015, Chittoor et al.
Ammerer, "Expression of Genes in Yeast Using the ADCI Promoter," *Methods in Enzymology* 101:192-201, 1983.
Benfey et al., "The CaMV 35S enhancer contains at least two domains which can confer different developmental and tissue-specific expression patterns," *EMBO J* 8(8):2195-2202, 1989.
Cho et al., "Regulation of root hair initiation and expansin gene expression in *Arabidopsis*," *Plant Cell* 14:3237-3253, 2002.
European Extended Search Report for European Application No. 14776232, dated Jul. 18, 2016.
GenBank Accession No. AC122161, dated Sep. 17, 2010.
GenBank Accession No. AC139600, dated Sep. 17, 2010.
GenBank Accession No. AC145767, dated Sep. 17, 2010.
GenBank Accession No. AC174341, dated Sep. 17, 2010.
GenBank Accession No. AF000354, dated Mar. 15, 1999.
GenBank Accession No. BG645158, dated Apr. 24, 2001.
GenBank Accession No. XM 003589997, dated Nov. 21, 2011.
GenBank Accession No. BT140834, dated May 25, 2012.
International Search Report and Written Opinion for PCT Application No. PCT/US14/23648, dated Aug. 29, 2014.
Iwase et al., "Manipulation of plant metabolism by transcription factors," *Plant Biotechnology* 26:29-38, 2009.
Kim et al., "A 20 nucleotide upstream element is essential for the nopaline synthase (nos) promoter activity," *Plant Mol Biol* 24(1):105-117, 1994.
Kim et al., "Isolation and Characterization of *Medicago truncatula* U6 Promoters for the Construction of Small Hairpin RNA-Mediated Gene Silencing Vectors," *Plant Mol. Biol. Rep.* 31:581-593, 2013.
Li et al., "Evaluation of seed storage protein gene 3'-untranslated regions in enhancing gene expression in transgenic rice seed," *Transgenic Res.* 21:545-553, 2012.
Li et al., "Cloning and Analysis of an Inducement-responsive Promoter MsZPP of *Medicago sativa* L.," Chinese Academy of Agricultural Sciences Dissertation dated May 2012.
Liu et al., "Cloning and Characterization of Two Phosphate Transporters from *Medicago truncatula* Roots: Regulation in Response to Phosphate and Colonization by Arbuscular Mycorrhizal (AM) Fungi," *Molecular Plant Microbe Interactions* 11:14-22, 1996.

(Continued)

*Primary Examiner* — Bratislav Stankovic
(74) *Attorney, Agent, or Firm* — Dentons US LLP; Timothy Ball; Carine Doyle

(57) ABSTRACT

Recombinant DNA molecules and constructs useful for modulating gene expression in plants, including molecules derived from *Medicago truncatula* sequences, are provided. Plants, plant cells, plant parts, and seeds comprising recombinant DNA molecules operably linked to heterologous transcribable DNA molecules are further provided, as are methods of their use.

14 Claims, 1 Drawing Sheet
Specification includes a Sequence Listing.

(56) References Cited

OTHER PUBLICATIONS

Mignone et al., "mRNA Untranslated Regions (UTRs)," In: eLS, John Wiley & Sons, pp. 1-5, 2011.
Office Action regarding Chinese Application No. 201480022713.6, dated Jan. 25, 2017.
Odell et al., "Identification of DNA sequences required for activity of the cauliflower mosaic virus 35S promoter," *Nature* 313:810-812, 1985.
Ortega et al., "The 3' untranslated region of a soybean cytosolic glutamine synthetase ($GS_1$) affects transcript stability and protein accumulation in transgenic alfalfa," *The Plant Journal* 45:832-846, 2006.
Pesole et al., "The untranslated regions of eukaryotic mRNAs: Structure, function, evolution and bioinformatic tools for their analysis," *Briefings in Bioinformatics* 1:236-249, 2000.
Piechulla et al., "Identification of tomato Lhc promoter regions necessary for circadian expression," *Plant Molec Biol* 38(4):655-662, 1998.
Sherf et al., "Dual-Luciferase™ Reporter Assay: An Advanced Co-Reporter Technology Integratign Firefly and *Renilla* Luciferase Assays," *Promega Notes Magazine* No. 57:2, 1996.
Song et al., "Expression of Two Tissue-Specific Promoters in Transgenic Cotton Plants," *The Journal of Cotton Science* 4:217-223, 2000.
Tesniere et al., "Effect of different 3' flanking regions on the activity of the Vitis vinifera alcohol dehydrogenase 2 promoter," *Vitis* 44(1):1-4, 2005.
Tong et al., "Sequence Divergence in the 3'-Untranslated Region Has an Effect on the Subfunctionalization of Duplicate Genes," *J. Exp. Zool.* 3188:531-544, 2012.
Wei et al., "Comparative expression analysis of two sugarcane polyubiquitin promoters and flanking sequences in transgenic plants," *Journal of Plant Physiology* 160:1241-1251, 2003.
Welsch et al., "Structural and functional characterization of the phytoene synthase promoter from *Arabidopsis thaliana*," *Planta* 216:523-534, 2003.
Xiao et al., "Isolation and Characterization of Root-Specific Phosphate Transporter Promoters from *Medicago truncatula*," *Plant Biol.* 8:439-449, 2006.
USPTO: Non-Final Office Action regarding U.S. Appl. No. 14/949,690, dated Apr. 6, 2017.
GenBank Accession No. AC122162, dated Sep. 17, 2010.
GenBank Accession No. AC122171, dated Sep. 17, 2010.
GenBank Accession No. AC122727, dated Sep. 17, 2010.
GenBank Accession No. AC123575, dated Sep. 17, 2010.
GenBank Accession No. AC125478, dated Sep. 17, 2010.
GenBank Accession No. AC126009, dated Sep. 17, 2010.
GenBank Accession No. AC126014, dated Sep. 17, 2010.
GenBank Accession No. AC126794, dated Sep. 17, 2010.
GenBank Accession No. AC127429, dated Sep. 17, 2010.
GenBank Accession No. AC133139, dated Sep. 17, 2010.
GenBank Accession No. AC135505, dated Sep. 17, 2010.
GenBank Accession No. AC136138, dated Sep. 17, 2010.
GenBank Accession No. AC137554, dated Sep. 17, 2010.
GenBank Accession No. AC137668, dated Sep. 17, 2010.
GenBank Accession No. AC137822, dated Sep. 17, 2010.
GenBank Accession No. AC140914, dated Sep. 17, 2010.
GenBank Accession No. AC144723, dated Oct. 21, 2008.
GenBank Accession No. AC144765, dated Sep. 17, 2010.
GenBank Accession No. AC145164, dated Sep. 17, 2010.
GenBank Accession No. AC146307, dated Sep. 17, 2010.
GenBank Accession No. AC146308, dated Sep. 17, 2010.
GenBank Accession No. AC146555, dated Sep. 17, 2010.
GenBank Accession No. AC146572, dated Apr. 24, 2009.
GenBank Accession No. AC150978, dated Sep. 17, 2010.
GenBank Accession No. AC153125, dated Apr. 4, 2007.
GenBank Accession No. AC174287, dated Sep. 17, 2010.
GenBank Accession No. AC175311, dated Dec. 12, 2008.
GenBank Accession No. CR931735, dated Dec. 10, 2004.
GenBank Accession No. CT010481, dated Feb. 28, 2006.
GenBank Accession No. CT571263, dated Dec. 12, 2005.
GenBank Accession No. CT573354, dated Jul. 21, 2006.
GenBank Accession No. CT573507, dated Mar. 14, 2006.
GenBank Accession No. C1967313, dated Jul. 22, 2006.
GenBank Accession No. CU207236, dated Jan. 18, 2007.
GenBank Accession No. GZ210007 dated Apr. 3, 2012.
Response to Non-Final Office Action regarding U.S. Appl. No. 14/949,690, dated Jun. 26, 2017.
Office Action regarding Chinese Application No. 2014800227136, dated Jul. 20, 2017.
USPTO: Final Office Action regarding U.S. Appl. No. 14/949,690, dated Sep. 5, 2017.
USPTO: Applicant Initiated Interview Summary regarding U.S. Appl. No. 14/949,690, dated Nov. 1, 2017.
Response to Final Office Action regarding U.S. Appl. No. 14/949,690, dated Nov. 2, 2017.
GenBank Accession No. XM 003589991.1, dated Nov. 21, 2011.
U.S. Appl. No. 15/882,964, filed Jan. 29, 2018, Chittoor et al.
USPTO: Notice of Allowance and Fee(s) Due regarding U.S. Appl. No. 14/949,690, dated Nov. 30, 2017.
USPTO: Notice of Allowance and Fee(s) Due regarding U.S. Appl. No. 14/949,694, dated Nov. 30, 2017.
USPTO: Non-Final Office Action regarding U.S. Appl. No. 15/882,964, dated Apr. 17, 2019.
GenBank Accession No. CR492243, dated Nov. 17, 2004.
Response to Non-Final Office Action regarding U.S. Appl. No. 15/882,964, dated Jun. 17, 2019.
USPTO: Notice of Allowance and Fee(s) Due regarding U.S. Appl. No. 15/882,964, dated Jul. 25, 2019.
Examination Report regarding Australian Application No. 2018204576, dated Aug. 12, 2019, 8 pages.
Examination Report regarding Australian Application No. 2018204541, dated Sep. 17, 2019, 8 pages.
GenBank Accession No. BI310369, Jul. 20, 2001.
Examination Report regarding Australian Application No. 2018204531, dated Sep. 23, 2019, 7 pages.
GenBank Accession No. CA991284, Jan. 6, 2003.

\* cited by examiner

Transgene Cassette Configuration 1
| Promoter or chimeric promoter [A] | Leader [B] | Intron [C] | Coding Region [D] | 3' UTR [E] |
Transgene Cassette Configuration 2
| Promoter or chimeric promoter [F] | Leader [G] | Intron [H] | Leader [I] | Coding Region [J] | 3' UTR [K] |
Transgene Cassette Configuration 3
| Promoter or chimeric promoter [L] | Leader [M] | Coding Region [N] | Intron [O] | Coding Region [P] | 3' UTR [Q] |

PLANT REGULATORY ELEMENTS DERIVED FROM *MEDICAGO TRUNCATULA* 3'UTR SEQUENCES, AND USES THEREOF

REFERENCE TO RELATED APPLICATIONS

This application is a divisional of U.S. application Ser. No. 14/949,694, filed Nov. 23, 2015 (pending), which is a divisional of U.S. application Ser. No. 14/205,251, filed Mar. 11, 2014, now U.S. Pat. No. 9,222,099 issued Dec. 29, 2015, which claims the benefit of U.S. provisional application Ser. No. 61/785,268, filed Mar. 14, 2013, each of which is incorporated herein by reference in its entirety.

INCORPORATION OF SEQUENCE LISTING

The sequence listing that is contained in the file named "MONS332US.txt", which is 52.7 kilobytes (as measured in Microsoft Windows®) and was created on Mar. 11, 2014, is filed herewith by electronic submission and is incorporated by reference herein.

FIELD OF THE INVENTION

The invention relates to the field of plant molecular biology, plant genetic engineering, and DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides novel regulatory elements for use in plants, and constructs comprising the regulatory elements. The invention also provides transgenic plant cells, plants, and seeds comprising the regulatory elements. In one embodiment disclosed herein, the regulatory elements are operably linked to a transcribable DNA molecule. In certain embodiments, the transcribable DNA molecule is heterologous with respect to the regulatory sequence. Also provided herein are methods for making and using the regulatory elements disclosed herein, including constructs comprising the regulatory elements, and the transgenic plant cells, plants, and seeds comprising the regulatory elements operably linked to a transcribable DNA molecule that is heterologous with respect to the regulatory element.

Thus, in one aspect, the invention provides a recombinant DNA molecule comprising a DNA sequence selected from the group consisting of: (a) a DNA sequence with at least about 85 percent sequence identity to any of SEQ ID NOs: 1-37; (b) a DNA sequence comprising any of SEQ ID NOs: 1-37; and (c) a fragment of any of SEQ ID NOs: 1-37, wherein the fragment has gene-regulatory activity; wherein the DNA sequence is operably linked to a heterologous transcribable DNA molecule. By "heterologous transcribable DNA molecule," it is meant that the transcribable DNA molecule is heterologous with respect to the DNA sequence to which it is operably linked. In specific embodiments, the recombinant DNA molecule comprises a DNA sequence having at least 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs: 1-37. In particular embodiments, the heterologous transcribable DNA molecule comprises a gene of agronomic interest, such as a gene capable of providing herbicide resistance or pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a DNA sequence with at least about 85 percent sequence identity to any of SEQ ID NOs: 1-37; (b) a DNA sequence comprising any of SEQ ID NOs: 1-37; and (c) a fragment of any of SEQ ID NOs: 1-37, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a DNA sequence with at least 85 percent sequence identity to any of SEQ ID NOs: 1-37; b) a DNA sequence comprising any of SEQ ID NOs: 1-37; and c) a fragment of any of SEQ ID NOs: 1-37, wherein the fragment has gene-regulatory activity; wherein the DNA sequence is operably linked to a heterologous transcribable DNA molecule. In specific embodiments, the transgenic plant is a progeny plant of any generation relative to a starting transgenic plant and comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is processed seeds, grains, plant parts, and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE FIGURES

FIG. 1: Shows expression cassette configurations of the invention.

BRIEF DESCRIPTION OF THE SEQUENCES

SEQ ID NOs: 1-30, 38-41, 49 and 56 are 3' UTR sequences.

SEQ ID NOs: 31, 35, 42, 47, 48, 50, 51, 52, 53, 54 and 55 are DNA sequences of regulatory expression element groups (EXPs) comprising a promoter sequence operably linked 5' to a leader sequence, which is operably linked 5' to an intron sequence; or a promoter sequence operably linked 5' to a leader sequence.

SEQ ID NOs: 32, 36, and 43 are promoter sequences.

SEQ ID NOs: 33 and 37 are leader sequences.

SEQ ID NO: 34 is an intron sequence.

SEQ ID NO: 44 is a coding sequence for β-glucuronidase (GUS) that possesses a processable intron.

SEQ ID NOs: 45 and 46 are luciferase coding sequences.

DETAILED DESCRIPTION OF THE INVENTION

The invention provides DNA molecules having gene-regulatory activity in plants. The nucleotide sequences of these DNA molecules are provided as SEQ ID NOs: 1-37. These DNA molecules are capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing the recombinant DNA molecules of the invention, and methods for preparing and using the same.

The following definitions and methods are provided to better define the invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases. As used herein, the term "DNA sequence" to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation.

As used herein, the term "sequence identity" refers to the extent to which two optimally aligned DNA sequences are identical. An optimal sequence alignment is created by manually aligning two sequences, e.g., a reference sequence and another DNA sequence, to maximize the number of nucleotide matches in the sequence alignment with appropriate internal nucleotide insertions, deletions, or gaps. As used herein, the term "reference sequence" refers to a DNA sequence provided as SEQ ID NOs: 1-37.

As used herein, the term "percent sequence identity" or "percent identity" or "% identity" is the identity fraction multiplied by 100. The "identity fraction" for a DNA sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a DNA sequence that, when optimally aligned to a reference sequence, provided herein as SEQ ID NOs: 1-37, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders, enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence, which is in turn operably linked 5' to an intron sequence.

Regulatory elements may be characterized by their gene expression pattern, e.g., positive and/or negative effects such as constitutive, temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially identified from the 5' untranslated region (5' UTR) of a gene. Alternately, promoters may be synthetically produced or manipulated DNA molecules. Promoters may also be chimeric. Chimeric promoters are produced through the fusion of two or more heterologous DNA molecules. Promoters useful in practicing the invention include SEQ ID NOs: 32 and 36, including fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters, or in combination with other EXPs and EXP fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. Methods for producing such fragments from a starting promoter molecule are well known in the art.

Compositions derived from any of the promoters presented as SEQ ID NOs: 32 and 36, such as internal or 5' deletions, for example, can be produced using methods well known in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoters presented as SEQ ID NOs: 32 and 36 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythm) effects on expression. Any of the promoters presented as SEQ ID NOs: 32 and 36 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule identified from the untranslated 5' region (5' UTR) of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in practicing the invention include SEQ ID NOs: 33 and 37 or fragments or variants thereof. In specific embodiments, such DNA sequences may be defined as being capable of acting as a leader in a host cell, including, for example, a transgenic plant cell. In one embodiment, such DNA sequences may be decoded as comprising leader activity.

The leader sequences presented as SEQ ID NOs: 33 and 37 may be comprised of regulatory elements, or may adopt secondary structures that can have an effect on transcription or translation of an operably linked transcribable DNA molecule. The leader sequences presented as SEQ ID NOs: 33 and 37 can be used in accordance with the invention to make chimeric regulatory elements that affect transcription or translation of an operably linked DNA molecule.

As used herein, the term "intron" refers to a DNA molecule that may be identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant has been shown, in certain circumstances, to exhibit disadvantages. In those cases, it is necessary to have a collection of basic control elements for the construction of appropriate recombinant DNA elements.

Introns useful in practicing the invention include SEQ IN NO: 34. Compositions derived from the intron presented as SEQ ID NO: 34 can be comprised of internal deletions or duplications of cis-regulatory elements; and/or alterations of the 5' and 3' DNA sequences comprising the intron/exon splice junctions can be used to improve expression or specificity of expression when operably linked to a promoter+leader or chimeric promoter+leader and coding sequence. When modifying intron/exon boundary sequences, it may be beneficial to avoid using the nucleotide sequence AT or the nucleotide A just prior to the 5' end of the splice site (GT) and the nucleotide G or the nucleotide sequence TG, respectively, just after the 3' end of the splice site (AG) to eliminate the potential of unwanted start codons from being formed during processing of the messenger RNA into the final transcript. The DNA sequence around the 5' or 3' end splice junction sites of the intron can thus be modified in this manner. Intron and intron variants altered as described herein and through methods known in the art can be tested empirically as described in the working examples to determine the intron's effect on expression of an operably linked DNA molecule. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods can be difficult in that there are few conserved DNA sequences that would allow for easy prediction of an effective 3' UTR.

From a practical standpoint, it is typically beneficial that a 3' UTR used in an expression cassette possesses the following characteristics. The 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. In plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked transcribable DNA molecule. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays; or by DNA sequence similarity analysis using known cis-element motifs or enhancer elements as a target sequence or target motif with conventional DNA sequence comparison methods, such as the Basic Local Alignment Search Tool (BLAST®, National Library of Medicine). The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be found in that configuration, i.e., fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the present invention.

As used herein, the term "variant" refers to a second DNA molecule, such as a regulatory element, that is similar in composition, but not identical to, a first DNA molecule, and wherein the second DNA molecule still maintains the general functionality, i.e., same or similar expression pattern, for instance through more or less or equivalent transcriptional or translational activity, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. Regulatory element "variants" also encompass variants arising from mutations that occur during or as a result of bacterial and plant cell transformation. In the invention, a DNA sequence provided as SEQ ID NOs: 1-37 may be used to create variants that are in similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, a DNA sequence provided as SEQ ID NOs: 1-30 or 31-37 may provide a regulatory element reference sequence, wherein the constituent elements that comprise the reference sequence may be joined by methods known in the art and may comprise substitutions, deletions, and/or insertions of one or more nucleotides or mutations that naturally occur in bacterial and plant cell transformation.

The efficacy of the modifications, duplications, or deletions described herein on the desired expression aspects of a particular transcribable DNA molecule may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e., operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are arranged so that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter is capable of affecting the transcription or translation of the transcribable DNA molecule.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. For example, typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transcribable DNA molecule encoding non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-37, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379;

6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), luciferase, green fluorescent protein (GFP), proteins that confer antibiotic resistance, and proteins that confer herbicide tolerance.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also includes progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique,* (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NO:1-37. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Regulatory expression element groups (EXPs) and transcription termination regions (3' UTRs) were identified and cloned from the genomic DNA of the dicot species *Medicago truncatula* (Barrel Medic). The selection of the *Medicago truncatula* 3' UTRs was, in part, based on expression patterns observed in homologous soybean genes.

The identification and cloning of *Medicago truncatula* 3' UTRs began with the selection of soybean genes of interest based upon the soybean genes' expression pattern in soy tissue surveys and proprietary transcript profiling experiments. The selected soybean genes were then used to find homologous genes in *Medicago truncatula* using publicly available DNA sequences. Next, tissue samples derived from *Medicago truncatula* were isolated from plants grown under different environmental conditions. Then, messenger RNA (mRNA) was isolated from the *Medicago* tissues and used in real time polymerase chain reaction (PCR) experiments to determine the expression pattern of the *Medicago* genes. From these experiments, a subset of the *Medicago truncatula* genome was selected for cloning and characterization.

Using public *Medicago truncatula* sequence data, a bioinformatic analysis was performed to identify regulatory elements within the selected *Medicago* gene loci. For example, bioinformatic analysis was performed to identify 3' UTR sequences that comprise the polyadenylation and termination regions of the mRNA and sequences extending further to the end of the identified gene locus. Amplification primers were then designed and used to amplify each of the identified regulatory element DNA fragments, such as 3' UTR DNA fragments, DNA fragments comprising a promoter, leader and intron, and DNA fragments comprising a promoter and leader. The resulting DNA fragments were ligated into base plant expression vectors and sequenced.

For applicable DNA fragments, an analysis of the regulatory element transcription start site (TSS) and intron/exon splice junctions was then performed using transformed plant protoplasts. In this analysis, the protoplasts were transformed with the plant expression vectors comprising the cloned DNA fragments operably linked to a heterologous transcribable DNA molecule. Next, the 5' RACE System for Rapid Amplification of cDNA Ends, Version 2.0 (Invitrogen, Carlsbad, Calif. 92008) was used to confirm the regulatory element TSS and intron/exon splice junctions by analyzing the DNA sequence of the produced mRNA transcripts.

The DNA sequences of the identified 3' UTRs are provided herein as SEQ ID NOs: 1-30. In addition, identified promoter DNA sequences are provided herein as SEQ ID NOs: 32 and 36; identified leader DNA sequences are provided herein as SEQ ID NOs: 33 and 37; and an identified intron DNA sequence is provided as SEQ ID NO: 34. Further, the DNA sequences of the identified EXPs are provided herein as SEQ ID NOs: 31 and 35. The regulatory expression element group EXP-Mt.Ubq2:1:2 (SEQ ID NO: 31) comprises a promoter element, P-Mt.Ubq2-1:1:1 (SEQ ID NO: 32), operably linked 5' to a leader element, L-Mt.Ubq2-1:1:1 (SEQ ID NO: 33), operably linked 5' to an intron element, I-Mt.Ubq2-1:1:2 (SEQ ID NO: 34) and the regulatory expression element group EXP-Mt.AC145767v28:1:1 (SEQ ID NO: 35) comprises a promoter element, P-Mt.AC145767v28-1:2:1 (SEQ ID NO: 36), operably linked 5' to a leader element, L-Mt.AC145767v28-1:1:2 (SEQ ID NO: 37). Each of the DNA sequences identified and cloned from *Medicago truncatula* are listed in Table 1.

TABLE 1

3' UTRs, Regulatory expression element groups, promoters, leaders, and introns cloned from *Medicago truncatula*.

| Description | SEQ ID NO: | Annotation |
|---|---|---|
| T-Mt.AC145767v28-1:1:2 | 1 | AC145767.28 |
| T-Mt.AC140914v20-1:2:1 | 2 | AC140914.20 |
| T-Mt.AC139600v16-1:2:1 | 3 | AC139600.16 |
| T-Mt.AC153125V10-1:2:1 | 4 | AC153125.10 |
| T-Mt.Apx-1:1:2 | 5 | cytosolic ascorbate peroxidase |
| T-Mt.EF1a-1:1:2 | 6 | elongation factor 1 alpha |
| T-Mt.Expr1-1:2:1 | 7 | putative oxidoreductase |
| T-Mt.FBA-1:1:5 | 8 | fructose biphasphate aldolase, cytoplasmic isozyme 2 |
| T-Mt.FBA-1:2:1 | 9 | fructose biphasphate aldolase, cytoplasmic isozyme 2 |
| T-Mt.Gapdh-1:2:1 | 10 | glyceraldehyde-3-phosphate dehydrogenase |
| T-Mt.Gpi-1:2:1 | 11 | GPI-anchored protein |
| T-Mt.Hsp20-1:2:1 | 12 | heat shock protein 20 |
| T-Mt.Lhcb2-1:2:1 | 13 | chlorophyll a/b binding protein type II precursor |
| T-Mt.Lox-1-1:2:1 | 14 | lipoxygenase |
| T-Mt.Methm-1:2:1 | 15 | 5-methyltetrahydropteroyltriglutamate-homocysteine S-methyltransferase |
| T-Mt.MP21-1:2:1 | 16 | seed maturation protein |
| T-Mt.Oxr-1:2:1 | 17 | putative oxidoreductase |
| T-Mt.Pip1-1:2:1 | 18 | plasma membrane integral protein |
| T-Mt.Prx-1:1:1 | 19 | peroxidase |
| T-Mt.PSII-T_A-1:2:1 | 20 | photosystem II 5 kDa protein, chloroplast precursor |
| T-Mt.PSII-T_B-1:2:1 | 21 | photosystem II 5 kDa protein, chloroplast precursor |
| T-Mt.Pt1-1:2:2 | 22 | phosphate Transporter |
| T-Mt.Pt2-1:2:2 | 23 | phosphate Transporter |
| T-Mt.RD22-1:2:1 | 24 | dehydration-responsive protein |
| T-Mt.RpL3-1:2:1 | 25 | ribosomal protein L3 |
| T-Mt.Sali3-2-1:2:1 | 26 | aluminum-induced Sali3-2 protein |
| T-Mt.Scp-1:2:1 | 27 | serine carboxypeptidase-related protein |
| T-Mt.SeqID#21-1:2:1 | 28 | peroxidase |
| T-Mt.Sui1-1:1:2 | 29 | SUI1 translation initiation factor |
| T-Mt.Zfp-1:2:1 | 30 | CCCH-type zinc finger protein |
| EXP-Mt.Ubq2:1:2 | 31 | Ubiquitin 2 |
| P-Mt.Ubq2-1:1:1 | 32 | Ubiquitin 2 |
| L-Mt.Ubq2-1:1:1 | 33 | Ubiquitin 2 |
| I-Mt.Ubq2-1:1:2 | 34 | Ubiquitin 2 |
| EXP-Mt.AC145767v28:1:1 | 35 | AC145767.28 |
| P-Mt.AC145767v28-1:2:1 | 36 | AC145767.28 |
| L-Mt.AC145767v28-1:1:2 | 37 | AC145767.28 |

Example 2

Analysis of the Effect of 3' UTRs on Constitutive GUS Expression in Soybean Leaf Protoplasts Soybean leaf protoplasts were transformed with vectors, specifically plasmid constructs, to assess the effect of selected *Medicago truncatula* 3' UTRs on expression. Soybean leaf protoplasts were transformed with DNA vectors containing a constitutive EXP sequence driving expression of the β-glucuronidase (GUS) transgene operably linked to a *Medicago* 3' UTR. These *Medicago* 3' UTR-transformed soybean leaf protoplasts were compared to soybean leaf protoplast in which expression of the GUS transgene was driven by a constitutive promoter, and the GUS transgene was operably linked to a 3' UTR derived from *Gossypium hirsutum* or *Gossypium barbadense*.

The plant vectors utilized in these experiments were built using cloning methods known in the art. The resulting vectors comprised a left border region from *A. tumefaciens*; a first transgene expression cassette for selection of transformed plant cells that confers resistance to either the herbicide glyphosate or the antibiotic spectinomycin (both driven by the *Arabidopsis* Actin 7 promoter); a second transgene expression cassette used to assess the activity of the 3' UTR, which comprised an EXP or promoter sequence operably linked 5' to a DNA sequence for GUS that possesses a processable intron (GUS-2, SEQ ID NO: 44), which is operably linked 5' to 3' UTR derived from *Medicago truncatula*, *Gossypium hirsutum*, or *Gossypium barbadense*; and a right border region from *A. tumefaciens*. The vectors that comprised a 3' UTR derived from *Medicago* (i.e., pMON109593, pMON116803, pMON116812, pMON116813, pMON116815, pMON116826, pMON116827, pMON116830, pMON122852, pMON122853, pMON122854, pMON122855, pMON122856, pMON122857, pMON122858, pMON122859, pMON122862, pMON122864, pMON122865, pMON122866, pMON122867, and pMON122868) used the constitutive regulatory expression element group EXP-CaMV.35S-enh+Ph.DnaK:1:3 (SEQ ID NO: 42) to drive GUS. The vectors that comprised a 3' UTR derived from *Gossypium hirsutum* or *Gossypium barbadense* (i.e., pMON81345, pMON81347, and pMON83002) used the constitutive promoter P-CaMV.35S-enh-1:1:11 (SEQ ID NO: 43) to drive GUS.

Table 2 provides the plasmid constructs with the corresponding 3' UTR and SEQ ID NO used to transform the soybean protoplasts in experiments presented in this Example.

TABLE 2

Plasmid constructs used to transform soybean leaf protoplasts and 3' UTR descriptions.

| Plasmid Construct | 3' UTR Description | SEQ ID NO: |
|---|---|---|
| pMON81345 | T-Gb.FbL2-1:1:1 | 41 |
| pMON81347 | T-Gh.E6-4A-0:2:1 | 38 |
| pMON83002 | T-Gb.H6-1:2:1 | 39 |
| pMON109593 | T-Mt.Pt1-1:2:2 | 22 |
| pMON116803 | T-Mt.AC140914v20-1:2:1 | 2 |
| pMON116812 | T-Mt.Lhcb2-1:2:1 | 13 |
| pMON116813 | T-Mt.PSII-T_B-1:2:1 | 21 |
| pMON116815 | T-Mt.AC145767v28-1:1:2 | 1 |
| pMON116826 | T-Mt.Lox-1-1:2:1 | 14 |
| pMON116827 | T-Mt.Gpi-1:2:1 | 11 |
| pMON116830 | T-Mt.Scp-1:2:1 | 27 |
| pMON122852 | T-Mt.Methm-1:2:1 | 15 |
| pMON122853 | T-Mt.Prx-1:1:1 | 19 |
| pMON122854 | T-Mt.Gapdh-1:2:1 | 10 |
| pMON122855 | T-Mt.FBA-1:1:5 | 8 |
| pMON122856 | T-Mt.Zfp-1:2:1 | 30 |
| pMON122857 | T-Mt.AC139600v16-1:2:1 | 3 |
| pMON122858 | T-Mt.MP21-1:2:1 | 16 |
| pMON122859 | T-Mt.Oxr-1:2:1 | 17 |
| pMON122862 | T-Mt.Sui1-1:1:2 | 29 |
| pMON122864 | T-Mt.Pip1-1:2:1 | 18 |
| pMON122865 | T-Mt.AC153125V10-1:2:1 | 4 |
| pMON122866 | T-Mt.Sali3-2-1:2:1 | 26 |
| pMON122867 | T-Mt.Hsp20-1:2:1 | 12 |
| pMON122868 | T-Mt.Expr1-1:2:1 | 7 |

Two plant vectors, specifically plasmid constructs, for use in co-transformation and normalization of data were also built using cloning methods known in the art. Each of these plasmid constructs contained a specific luciferase coding sequence that was driven by a constitutive EXP. The plant vector pMON19437 comprised an expression cassette with a constitutive EXP comprising a promoter operably linked 5' to a leader sequence which is operably linked 5' to an intron (EXP-CaMV.35S-enh+Zm.DnaK:1:1, SEQ ID NO: 47), operably linked 5' to a firefly (*Photinus pyralis*) luciferase coding sequence (LUCIFERASE:1:3, SEQ ID NO: 45), operably linked 5' to a 3' UTR from the *Agrobacterium tumefaciens* nopaline synthase gene (T-AGRtu.nos-1:1:13, SEQ ID NO: 49). The plant vector pMON63934 comprised an expression cassette with a constitutive EXP sequence comprising a promoter operably linked 5' to a leader sequence (EXP-CaMV.35S-enh-Lhcb1, SEQ ID NO: 48), operably linked 5' to a sea pansy (*Renilla reniformis*) luciferase coding sequence (CR-Ren.hRenilla Lucife-0:0:1, SEQ ID NO: 46), operably linked 5' to a 3' UTR from the *Agrobacterium tumefaciens* nopaline synthase gene (T-AGRtu.nos-1:1:13, SEQ ID NO: 49).

The soybean leaf protoplasts were transformed using a polyethylene glycol (PEG)-based transformation method, as is well known in the art. Each protoplast cell was transformed with the pMON19437 plasmid construct, the pMON63934 plasmid construct, and one of the plasmid constructs presented in Table 2. After transformation, the transformed soybean leaf protoplasts were incubated overnight in total darkness. Next, measurement of GUS and luciferase was conducted by placing aliquots of a lysed preparation of transformed cells into two different small-well trays. One tray was used for GUS measurements, and a second tray was used to perform a dual luciferase assay using the dual luciferase reporter assay system (Promega Corp., Madison, Wis.; see, e.g., Promega Notes Magazine, NO: 57, 1996, p.02).

One or two transformations were performed for each plasmid construct presented in Table 2. The mean expression values for each 3' UTR were determined from several samples from each transformation. Sample measurements were made using four replicates of each plasmid construct transformation, or alternatively, three replicates of each plasmid construct per one of two transformation experiments. The mean GUS and luciferase expression levels are provided in Table 3. In this Table, the firefly luciferase values (e.g., from expression of pMON19437) are provided in the column labeled "FLuc" and the sea pansy luciferase values (e.g., from expression of pMON63934) are provided in the column labeled "RLuc."

TABLE 3

Mean GUS and Luciferase assay values in transformed soybean leaf protoplasts.

| Plasmid Construct | 3' UTR Description | SEQ ID NO: | GUS | FLuc | RLuc |
|---|---|---|---|---|---|
| pMON81345 | T-Gb.FbL2-1:1:1 | 41 | 795 | 2332.5 | 3701 |
| pMON81347 | T-Gh.E6-4A-0:2:1 | 38 | 73 | 584.3 | 802 |
| pMON83002 | T-Gb.H6-1:2:1 | 39 | 91 | 1142.8 | 1995 |
| pMON109593 | T-Mt.Pt1-1:2:2 | 22 | 4783 | 3619 | 12341 |
| pMON116803 | T-Mt.AC140914v20-1:2:1 | 2 | 15053 | 4801.7 | 15876 |
| pMON116812 | T-Mt.Lhcb2-1:2:1 | 13 | 9771 | 4202.3 | 10976 |
| pMON116813 | T-Mt.PSII-T_B-1:2:1 | 21 | 7482 | 3347.3 | 8395 |
| pMON116815 | T-Mt.AC145767v28-1:1:2 | 1 | 30469 | 6428 | 17764 |
| pMON116826 | T-Mt.Lox-1-1:2:1 | 14 | 22330 | 3580.5 | 9984 |
| pMON116827 | T-Mt.Gpi-1:2:1 | 11 | 269 | 343.7 | 478 |
| pMON116830 | T-Mt.Scp-1:2:1 | 27 | 3909 | 4683.7 | 10180 |
| pMON122852 | T-Mt.Methm-1:2:1 | 15 | 33403 | 11049 | 28226 |
| pMON122853 | T-Mt.Prx-1:1:1 | 19 | 12833 | 11198 | 22722 |
| pMON122854 | T-Mt.Gapdh-1:2:1 | 10 | 14811 | 8775.5 | 25229 |
| pMON122855 | T-Mt.FBA-1:1:5 | 8 | 40383 | 17826 | 50299 |
| pMON122856 | T-Mt.Zfp-1:2:1 | 30 | 21870 | 16141.3 | 56362 |
| pMON122857 | T-Mt.AC139600v16-1:2:1 | 3 | 24386 | 6782.7 | 15024 |
| pMON122858 | T-Mt.MP21-1:2:1 | 16 | 30753 | 12929.8 | 40571 |
| pMON122859 | T-Mt.Oxr-1:2:1 | 17 | 14499 | 5586.7 | 15222 |
| pMON122862 | T-Mt.Sui1-1:1:2 | 29 | 27768 | 14680 | 35263 |
| pMON122864 | T-Mt.Pip1-1:2:1 | 18 | 40579 | 15837.7 | 36515 |
| pMON122865 | T-Mt.AC153125V10-1:2:1 | 4 | 34867 | 17285.5 | 52519 |

TABLE 3-continued

Mean GUS and Luciferase assay values in transformed soybean leaf protoplasts.

| Plasmid Construct | 3' UTR Description | SEQ ID NO: | GUS | FLuc | RLuc |
|---|---|---|---|---|---|
| pMON122866 | T-Mt.Sali3-2-1:2:1 | 26 | 33664 | 11923 | 27663 |
| pMON122867 | T-Mt.Hsp20-1:2:1 | 12 | 7088 | 9885.3 | 19590 |
| pMON122868 | T-Mt.Expr1-1:2:1 | 7 | 14539 | 7563.5 | 22320 |

Further, to compare the relative activity of each 3' UTR, GUS values were expressed as a ratio of GUS to luciferase activity and normalized to the best expressing non-*Medicago* 3' UTR, i.e., T-Gb.FbL2-1:1:1 (SEQ ID NO: 41). Table 4 shows the GUS/Luciferase ratios and the normalized ratios. Again, in this Table, the firefly luciferase values are labeled "FLuc" and the sea pansy luciferase values are labeled "RLuc."

TABLE 4

GUS/FLuc and GUS/RLuc ratios of expression normalized with respect to T-Gb.FbL2-1:1:1 (SEQ ID NO: 41) in transformed soybean leaf protoplasts.

| 3' UTR Description | SEQ ID NO: | GUS/FLuc | GUS/RLuc | GUS/FLuc Normalized to T-Gb.FbL2-1:1:1 | GUS/RLuc Normalized to T-Gb.FbL2-1:1:1 |
|---|---|---|---|---|---|
| T-Gb.FbL2-1:1:1 | 41 | 0.34 | 0.21 | 1.00 | 1.00 |
| T-Gh.E6-4A-0:2:1 | 38 | 0.12 | 0.09 | 0.37 | 0.42 |
| T-Gb.H6-1:2:1 | 39 | 0.08 | 0.05 | 0.23 | 0.21 |
| T-Mt.Pt1-1:2:2 | 22 | 1.32 | 0.39 | 3.88 | 1.80 |
| T-Mt.AC140914v20-1:2:1 | 2 | 3.13 | 0.95 | 9.20 | 4.41 |
| T-Mt.Lhcb2-1:2:1 | 13 | 2.33 | 0.89 | 6.82 | 4.14 |
| T-Mt.PSII-T_B-1:2:1 | 21 | 2.24 | 0.89 | 6.56 | 4.15 |
| T-Mt.AC145767v28-1:1:2 | 1 | 4.74 | 1.72 | 13.91 | 7.98 |
| T-Mt.Lox-1-1:2:1 | 14 | 6.24 | 2.24 | 18.30 | 10.41 |
| T-Mt.Gpi-1:2:1 | 11 | 0.78 | 0.56 | 2.30 | 2.62 |
| T-Mt.Scp-1:2:1 | 27 | 0.83 | 0.38 | 2.45 | 1.79 |
| T-Mt.Methm-1:2:1 | 15 | 3.02 | 1.18 | 8.87 | 5.51 |
| T-Mt.Prx-1:1:1 | 19 | 1.15 | 0.56 | 3.36 | 2.63 |
| T-Mt.Gapdh-1:2:1 | 10 | 1.69 | 0.59 | 4.95 | 2.73 |
| T-Mt.FBA-1:1:5 | 8 | 2.27 | 0.80 | 6.65 | 3.74 |
| T-Mt.Zfp-1:2:1 | 30 | 1.35 | 0.39 | 3.98 | 1.81 |
| T-Mt.AC139600v16-1:2:1 | 3 | 3.60 | 1.62 | 10.55 | 7.56 |
| T-Mt.MP21-1:2:1 | 16 | 2.38 | 0.76 | 6.98 | 3.53 |
| T-Mt.Oxr-1:2:1 | 17 | 2.60 | 0.95 | 7.61 | 4.43 |
| T-Mt.Sui1-1:1:2 | 29 | 1.89 | 0.79 | 5.55 | 3.67 |
| T-Mt.Pip1-1:2:1 | 18 | 2.56 | 1.11 | 7.52 | 5.17 |
| T-Mt.AC153125V10-1:2:1 | 4 | 2.02 | 0.66 | 5.92 | 3.09 |
| T-Mt.Sali3-2-1:2:1 | 26 | 2.82 | 1.22 | 8.28 | 5.67 |
| T-Mt.Hsp20-1:2:1 | 12 | 0.72 | 0.36 | 2.10 | 1.68 |
| T-Mt.Expr1-1:2:1 | 7 | 1.92 | 0.65 | 5.64 | 3.03 |

As demonstrated in Table 4, GUS expression was enhanced using all of the selected *Medicago* 3' UTRs compared to the 3' UTRs derived from *Gossypium hirsutum* or *Gossypium barbadense*. For example, expression of GUS was 2.1- to 18.3-fold higher using a *Medicago*-derived 3' UTR based upon the GUS/FLuc ratios normalized with respect to T-Gb.FbL2-1:1:1, the best expressing 3' UTR of those derived from *Gossypium hirsutum* or *Gossypium barbadense*. Similarly, expression of GUS was 1.61- to 10.48-fold higher using a *Medicago*-derived 3' UTR based upon the GUS/RLuc ratios normalized with respect to T-Gb-.FbL2-1:1:1.

Example 3

Analysis of the Effect of 3' UTRs on Constitutive GUS Expression in Stably Transformed Soybean Plants Soybean plants were transformed with vectors, specifically plasmid constructs, to assess the effect of selected *Medicago truncatula* 3' UTRs on expression. Specifically, soybean plants were transformed with vectors containing a constitutive EXP sequence driving expression of the β-glucuronidase (GUS) transgene operably linked to a *Medicago* 3' UTR. These *Medicago* 3' UTR-transformed soybean plants were compared to transformed soybean plants in which expression of the GUS transgene was driven by a constitutive promoter, and the GUS transgene was operably linked to a 3' UTR derived from *Gossypium barbadense*.

The plant vectors utilized in these experiments were built using cloning methods known in the art. The resulting vectors comprised a left border region from *A. tumefaciens*; a first transgene expression cassette for selection of transformed plant cells that confers resistance to the antibiotic spectinomycin (driven by the *Arabidopsis* Actin 7 promoter); a second transgene expression cassette used to assess the activity of the 3' UTR, which comprised the regulatory expression element group EXP-CaMV.35S-enh+Ph.DnaK:1:3 (SEQ ID NO: 42) operably linked 5' to a coding sequence for GUS that possesses a processable intron (GUS-2, SEQ ID NO: 44), which is operably linked 5' to a 3' UTR derived from *Medicago truncatula* or *Gossypium barbadense*; and a right border region from *A. tumefaciens*. The vectors that comprised a 3' UTR derived from *Medicago* were pMON109593, pMON116803, pMON116812, pMON116813, pMON116815, pMON116826, pMON116827, pMON116830, pMON122850, pMON122851, pMON122852, pMON122853, pMON122854, pMON122855, pMON122856, pMON122857, pMON122858, pMON122859, pMON122861, pMON122862, pMON122863, pMON122864, pMON122865, pMON122866, pMON122867, and pMON122868. The vector that comprised a 3' UTR from *Gossypium barbadense* was pMON102167.

Table 5 provides the plasmid constructs with the corresponding 3' UTR and SEQ ID NO used to transform the soybean plants in experiments presented in this Example.

TABLE 5

Plasmid constructs used to transform soybean plants and the 3' UTR descriptions.

| Plasmid Construct | 3' UTR Description | SEQ ID NO: |
|---|---|---|
| pMON102167 | T-Gb.E6-3b:1:1 | 40 |
| pMON109593 | T-Mt.Pt1-1:2:2 | 22 |
| pMON116803 | T-Mt.AC140914v20-1:2:1 | 2 |
| pMON116812 | T-Mt.Lhcb2-1:2:1 | 13 |
| pMON116813 | T-Mt.PSII-T_B-1:2:1 | 21 |
| pMON116815 | T-Mt.AC145767v28-1:1:2 | 1 |
| pMON116826 | T-Mt.Lox-1-1:2:1 | 14 |
| pMON116827 | T-Mt.Gpi-1:2:1 | 11 |
| pMON116830 | T-Mt.Scp-1:2:1 | 27 |
| pMON122850 | T-Mt.RpL3-1:2:1 | 25 |
| pMON122851 | T-Mt.RD22-1:2:1 | 24 |
| pMON122852 | T-Mt.Methm-1:2:1 | 15 |
| pMON122853 | T-Mt.Prx-1:1:1 | 19 |
| pMON122854 | T-Mt.Gapdh-1:2:1 | 10 |
| pMON122855 | T-Mt.FBA-1:1:5 | 8 |
| pMON122856 | T-Mt.Zfp-1:2:1 | 30 |
| pMON122857 | T-Mt.AC139600v16-1:2:1 | 3 |
| pMON122858 | T-Mt.MP21-1:2:1 | 16 |
| pMON122859 | T-Mt.Oxr-1:2:1 | 17 |
| pMON122861 | T-Mt.Apx-1:1:2 | 5 |
| pMON122862 | T-Mt.Sui1-1:1:2 | 29 |
| pMON122863 | T-Mt.EF1a-1:1:2 | 6 |
| pMON122864 | T-Mt.Pip1-1:2:1 | 18 |
| pMON122865 | T-Mt.AC153125V10-1:2:1 | 4 |
| pMON122866 | T-Mt.Sali3-2-1:2:1 | 26 |

TABLE 5-continued

Plasmid constructs used to transform soybean plants and the 3' UTR descriptions.

| Plasmid Construct | 3' UTR Description | SEQ ID NO: |
|---|---|---|
| pMON122867 | T-Mt.Hsp20-1:2:1 | 12 |
| pMON122868 | T-Mt.Expr1-1:2:1 | 7 |

The soybean plants were transformed using *Agrobacterium*-mediated transformation methods known in the art. Expression of GUS was assayed qualitatively using histological sections of selected tissues. For the histochemical GUS analysis, whole tissue sections were incubated with the GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, Vn5 Sink Leaf, Vn5 Source Leaf, R1 Source Leaf, R1 Petiole, R1 Flower, Yellow Pod Embryo (approximately R8 development stage), Yellow Pod Cotyledon (approximately R8 development stage), R3 Immature Seed, R3 Pod, and R5 Cotyledon.

The quantitative changes of GUS expression relative to expression imparted by pMON102167, which comprised the 3' UTR derived from *Gossypium barbadense*, was also analyzed, as demonstrated in Tables 6-13. For this quantitative analysis, total protein was extracted from selected tissues of transformed plants. One microgram of total protein was used with the fluorogenic substrate 4-methyleumbelliferyl-β-D-glucuronide (MUG) in a total reaction volume of 50 µl. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm, emission 3 nm.

Tables 6 and 7 show the mean quantitative expression levels measured in the $R_0$ generation plant tissues. Those tissues not assayed are shown as blank cells in both tables.

TABLE 6

Mean GUS expression in $R_0$ generation plants in Vn5 Root, Vn5 Sink Leaf, Vn5 Source Leaf, R1 Source Leaf, R1 Petiole, and R1 Flower.

| Plasmid Construct | 3' UTR Description | SEQ ID NO: | Vn5 Root | Vn5 Sink Leaf | Vn5 Source Leaf | R1 Source Leaf | R1 Petiole | R1 Flower |
|---|---|---|---|---|---|---|---|---|
| pMON102167 | T-Gb.E6-3b:1:1 | 40 | 400.90 | 551.61 | 605.29 | 350.93 | | 412.30 |
| pMON109593 | T-Mt.Pt1-1:2:2 | 22 | 740.77 | 654.50 | 946.25 | 579.76 | 342.11 | 215.37 |
| pMON116803 | T-Mt.AC140914v20-1:2:1 | 2 | 1306.76 | 2269.95 | 2187.61 | 344.78 | 480.47 | 243.11 |
| pMON116812 | T-Mt.Lhcb2-1:2:1 | 13 | 649.15 | 785.16 | 1103.30 | 644.76 | 297.30 | 294.38 |
| pMON116813 | T-Mt.PSII-T B-1:2:1 | 21 | 382.80 | 891.91 | 1026.78 | 262.82 | 253.94 | 179.31 |
| pMON116815 | T-Mt.AC145767v28-1:1:2 | 1 | 3817.28 | 1939.40 | 3250.38 | 1393.65 | 1001.37 | 876.08 |
| pMON116826 | T-Mt.Lox-1-1:2:1 | 14 | 1093.15 | 1626.41 | 2030.11 | 3315.25 | 1376.39 | 1980.93 |
| pMON116827 | T-Mt.Gpi-1:2:1 | 11 | 839.31 | 1263.82 | 1172.16 | 617.58 | 457.17 | 235.01 |
| pMON116830 | T-Mt.Scp-1:2:1 | 27 | 240.31 | 187.07 | 330.49 | 113.50 | 20.79 | 41.73 |
| pMON122850 | T-Mt.RpL3-1:2:1 | 25 | 479.50 | 673.20 | 687.00 | 388.10 | 524.10 | 202.68 |
| pMON122851 | T-Mt.RD22-1:2:1 | 24 | 897.98 | 287.52 | 667.63 | 325.50 | 1056.16 | 407.35 |
| pMON122852 | T-Mt.Methm-1:2:1 | 15 | 852.05 | 1003.70 | 456.38 | 883.30 | 560.70 | 184.02 |
| pMON122853 | T-Mt.Prx-1:1:1 | 19 | 858.88 | 591.51 | 362.40 | 841.82 | 459.48 | 220.29 |
| pMON122854 | T-Mt.Gapdh-1:2:1 | 10 | 957.90 | 910.53 | 343.90 | 583.62 | 570.15 | 198.11 |
| pMON122855 | T-Mt.FBA-1:1:5 | 8 | 1293.27 | 396.14 | 338.26 | 167.55 | 113.14 | 94.21 |
| pMON122856 | T-Mt.Zfp-1:2:1 | 30 | 254.48 | 250.56 | 154.27 | 425.90 | 223.53 | 115.33 |
| pMON122857 | T-Mt.AC139600v16-1:2:1 | 3 | 1035.43 | 1014.18 | 579.85 | 1631.94 | 921.34 | 421.81 |
| pMON122858 | T-Mt.MP21-1:2:1 | 16 | 408.94 | 299.07 | 282.34 | 315.48 | 562.46 | 308.11 |

TABLE 6-continued

Mean GUS expression in R₀ generation plants in Vn5 Root, Vn5 Sink Leaf, Vn5 Source Leaf, R1 Source Leaf, R1 Petiole, and R1 Flower.

| Plasmid Construct | 3' UTR Description | SEQ ID NO: | Vn5 Root | Vn5 Sink Leaf | Vn5 Source Leaf | R1 Source Leaf | R1 Petiole | R1 Flower |
|---|---|---|---|---|---|---|---|---|
| pMON122859 | T-Mt.Oxr-1:2:1 | 17 | 3228.98 | 1315.58 | 2092.77 | 849.69 | 406.58 | 98.10 |
| pMON122861 | T-Mt.Apx-1:1:2 | 5 | 974.70 | 433.60 | 510.50 | 263.00 | 103.70 | 117.70 |
| pMON122862 | T-Mt.Sui1-1:1:2 | 29 | 1131.24 | 710.62 | 604.88 | 342.22 | 182.58 | 219.67 |
| pMON122863 | T-Mt.EF1a-1:1:2 | 6 | 667.00 | 281.00 | 398.30 | 171.40 | 323.10 | 281.30 |
| pMON122864 | T-Mt.Pip1-1:2:1 | 18 | 448.00 | 203.00 | 240.00 | 401.00 | 369.00 | 355.00 |
| pMON122865 | T-Mt.AC153125V10-1:2:1 | 4 | 385.42 | 160.51 | 298.16 | 239.01 | 104.64 | 32.62 |
| pMON122866 | T-Mt.Sali3-2-1:2:1 | 26 | 2274.70 | 1176.10 | 1490.54 | 976.91 | 753.02 | 45.26 |
| pMON122867 | T-Mt.Hsp20-1:2:1 | 12 | 753.94 | 544.73 | 395.30 | 675.68 | 668.83 | 255.68 |
| pMON122868 | T-Mt.Expr1-1:2:1 | 7 | 1151.60 | 608.21 | 692.82 | 235.62 | 87.40 | 157.45 |

TABLE 7

Mean GUS expression in R₀ generation plants in Yellow Pod Embryo, Yellow Pod Cotyledon, R3 Immature Seed, R3 Pod, and R5 Cotyledon.

| Plasmid Construct | 3' UTR Description | SEQ ID NO: | Yellow Pod Embryo | Yellow Pod Cotyledon | R3 Immature Seed | R3 Pod | R5 Cotyledon |
|---|---|---|---|---|---|---|---|
| pMON102167 | T-Gb.E6-3b:1:1 | 40 | 47.86 | 49.45 | 67.45 | 433.54 | 101.34 |
| pMON109593 | T-Mt.Pt1-1:2:2 | 22 | 18.56 | 170.11 | 28.63 | 406.13 | 71.91 |
| pMON116803 | T-Mt.AC140914v20-1:2:1 | 2 | 100.42 | 181.62 | 209.92 | 467.72 | 190.51 |
| pMON116812 | T-Mt.Lhcb2-1:2:1 | 13 | 74.53 | 120.30 | 163.76 | 526.08 | 407.40 |
| pMON116813 | T-Mt.PSII-T B-1:2:1 | 21 | 127.65 | 279.84 | 78.12 | 282.34 | 50.92 |
| pMON116815 | T-Mt.AC145767v28-1:1:2 | 1 | 358.03 | 1192.69 | 989.47 | 2309.72 | 566.93 |
| pMON116826 | T-Mt.Lox-1:2:1 | 14 | 280.48 | 577.87 | 231.15 | 2868.17 | 341.60 |
| pMON116827 | T-Mt.Gpi-1:2:1 | 11 | 118.18 | 127.74 | 10.96 | 37.22 | 27.80 |
| pMON116830 | T-Mt.Scp-1:2:1 | 27 | 57.11 | 72.33 | 23.96 | 271.88 | 98.36 |
| pMON122850 | T-Mt.RpL3-1:2:1 | 25 | 265.30 | 489.70 | 57.40 | 487.50 | 264.40 |
| pMON122851 | T-Mt.RD22-1:2:1 | 24 | 95.88 | 189.41 | 121.12 | 1045.20 | 72.23 |
| pMON122852 | T-Mt.Methm-1:2:1 | 15 | 153.46 | 320.64 | 53.24 | 686.92 | 518.51 |
| pMON122853 | T-Mt.Prx-1:1:1 | 19 | 46.64 | 146.53 | 38.64 | 360.48 | 103.28 |
| pMON122854 | T-Mt.Gapdh-1:2:1 | 10 | 165.11 | 160.40 | 66.44 | 464.75 | 245.85 |
| pMON122855 | T-Mt.FBA-1:1:5 | 8 | 172.21 | 381.32 | 111.57 | 496.04 | 306.13 |
| pMON122856 | T-Mt.Zfp-1:2:1 | 30 | 46.37 | 44.66 | 87.51 | 775.69 | 57.17 |
| pMON122857 | T-Mt.AC139600v16-1:2:1 | 3 | 142.78 | 243.74 | 45.58 | 615.99 | 452.09 |
| pMON122858 | T-Mt.MP21-1:2:1 | 16 | 102.11 | 260.98 | 137.76 | 667.18 | 169.16 |
| pMON122859 | T-Mt.Oxr-1:2:1 | 17 | 192.92 | 539.13 | 74.44 | 950.85 | 43.69 |
| pMON122861 | T-Mt.Apx-1:1:2 | 5 | 53.50 | 217.70 | 37.90 | 95.30 | 174.50 |
| pMON122862 | T-Mt.Sui1-1:1:2 | 29 | 195.81 | 502.37 | 62.10 | 135.60 | 500.71 |
| pMON122863 | T-Mt.EF1a-1:1:2 | 6 | 136.80 | 270.20 | 127.20 | 387.10 | 150.00 |
| pMON122864 | T-Mt.Pip1-1:2:1 | 18 | 140.00 | 220.00 | 87.00 | 398.00 | 102.00 |
| pMON122865 | T-Mt.AC153125V10-1:2:1 | 4 | 20.55 | 56.64 | | | 11.83 |
| pMON122866 | T-Mt.Sali3-2-1:2:1 | 26 | 126.53 | 334.27 | | | 59.33 |
| pMON122867 | T-Mt.Hsp20-1:2:1 | 12 | 136.36 | 242.52 | 77.11 | 509.01 | 73.23 |
| pMON122868 | T-Mt.Expr1-1:2:1 | 7 | 201.21 | 186.14 | 208.37 | 1264.62 | 203.90 |

As demonstrated in Tables 6 and 7, expression driven by the same EXP was distinct in tissues of stably transformed soybean plants comprising different *Medicago* 3' UTRs when compared to the *Gossypium barbadense*-derived 3' UTR.

Tables 8 and 9 show the fold expression differences in the tissues of stably transformed soybean plants comprising different *Medicago* 3' UTRs when compared to the *Gossypium barbadense*-derived 3' UTR.

TABLE 8

Fold expression in R₀ generation transformed soybean plants in Vn5 Root, Vn5 Sink Leaf, Vn5 Source Leaf, R1 Source Leaf, R1 Petiole, and R1 Flower.

| Plasmid Construct | 3' UTR Description | SEQ ID NO: | Vn5 Root | Vn5 Sink Leaf | Vn5 Source Leaf | R1 Source Leaf | R1 Flower |
|---|---|---|---|---|---|---|---|
| pMON102167 | T-Gb.E6-3b:1:1 | 40 | 1.00 | 1.00 | 1.00 | 1.00 | 1.00 |
| pMON109593 | T-Mt.Pt1-1:2:2 | 22 | 1.85 | 1.19 | 1.56 | 1.65 | 0.52 |
| pMON116803 | T-Mt.AC140914v20-1:2:1 | 2 | 3.26 | 4.12 | 3.61 | 0.98 | 0.59 |

TABLE 8-continued

Fold expression in $R_0$ generation transformed soybean plants in Vn5 Root, Vn5 Sink Leaf, Vn5 Source Leaf, R1 Source Leaf, R1 Petiole, and R1 Flower.

| Plasmid Construct | 3' UTR Description | SEQ ID NO: | Vn5 Root | Vn5 Sink Leaf | Vn5 Source Leaf | R1 Source Leaf | R1 Flower |
|---|---|---|---|---|---|---|---|
| pMON116812 | T-Mt.Lhcb2-1:2:1 | 13 | 1.62 | 1.42 | 1.82 | 1.84 | 0.71 |
| pMON116813 | T-Mt.PSII-T B-1:2:1 | 21 | 0.95 | 1.62 | 1.70 | 0.75 | 0.43 |
| pMON116815 | T-Mt.AC145767v28-1:1:2 | 1 | 9.52 | 3.52 | 5.37 | 3.97 | 2.12 |
| pMON116826 | T-Mt.Lox-1-1:2:1 | 14 | 2.73 | 2.95 | 3.35 | 9.45 | 4.80 |
| pMON116827 | T-Mt.Gpi-1:2:1 | 11 | 2.09 | 2.29 | 1.94 | 1.76 | 0.57 |
| pMON116830 | T-Mt.Scp-1:2:1 | 27 | 0.60 | 0.34 | 0.55 | 0.32 | 0.10 |
| pMON122850 | T-Mt.RpL3-1:2:1 | 25 | 1.20 | 1.22 | 1.14 | 1.11 | 0.49 |
| pMON122851 | T-Mt.RD22-1:2:1 | 24 | 2.24 | 0.52 | 1.10 | 0.93 | 0.99 |
| pMON122852 | T-Mt.Methm-1:2:1 | 15 | 2.13 | 1.82 | 0.75 | 2.52 | 0.45 |
| pMON122853 | T-Mt.Prx-1:1:1 | 19 | 2.14 | 1.07 | 0.60 | 2.40 | 0.53 |
| pMON122854 | T-Mt.Gapdh-1:2:1 | 10 | 2.39 | 1.65 | 0.57 | 1.66 | 0.48 |
| pMON122855 | T-Mt.FBA-1:1:5 | 8 | 3.23 | 0.72 | 0.56 | 0.48 | 0.23 |
| pMON122856 | T-Mt.Zfp-1:2:1 | 30 | 0.63 | 0.45 | 0.25 | 1.21 | 0.28 |
| pMON122857 | T-Mt.AC139600v16-1:2:1 | 3 | 2.58 | 1.84 | 0.96 | 4.65 | 1.02 |
| pMON122858 | T-Mt.MP21-1:2:1 | 16 | 1.02 | 0.54 | 0.47 | 0.90 | 0.75 |
| pMON122859 | T-Mt.Oxr-1:2:1 | 17 | 8.05 | 2.39 | 3.46 | 2.42 | 0.24 |
| pMON122861 | T-Mt.Apx-1:1:2 | 5 | 2.43 | 0.79 | 0.84 | 0.75 | 0.29 |
| pMON122862 | T-Mt.Sui1-1:1:2 | 29 | 2.82 | 1.29 | 1.00 | 0.98 | 0.53 |
| pMON122863 | T-Mt.EF1a-1:1:2 | 6 | 1.66 | 0.51 | 0.66 | 0.49 | 0.68 |
| pMON122864 | T-Mt.Pip1-1:2:1 | 18 | 1.12 | 0.37 | 0.40 | 1.14 | 0.86 |
| pMON122865 | T-Mt.AC153125V10-1:2:1 | 4 | 0.96 | 0.29 | 0.49 | 0.68 | 0.08 |
| pMON122866 | T-Mt.Sali3-2-1:2:1 | 26 | 5.67 | 2.13 | 2.46 | 2.78 | 0.11 |
| pMON122867 | T-Mt.Hsp20-1:2:1 | 12 | 1.88 | 0.99 | 0.65 | 1.93 | 0.62 |
| pMON122868 | T-Mt.Expr1-1:2:1 | 7 | 2.87 | 1.10 | 1.14 | 0.67 | 0.38 |

TABLE 9

Fold expression in $R_0$ generation transformed soybean plants in Yellow Pod Embryo, Yellow Pod Cotyledon, R3 Immature Seed, R3 Pod, and R5 Cotyledon.

| Plasmid Construct | 3' UTR Description | SEQ ID NO: | Yellow Pod Embryo | Yellow Pod Cotyledon | R3 Immature Seed | R3 Pod | R5 Cotyledon |
|---|---|---|---|---|---|---|---|
| pMON102167 | T-Gb.E6-3b:1:1 | 40 | 1.00 | 1.00 | 1.00 | 1.00 | 1.00 |
| pMON109593 | T-Mt.Pt1-1:2:2 | 22 | 0.39 | 3.44 | 0.42 | 0.94 | 0.71 |
| pMON116803 | T-Mt.AC140914v20-1:2:1 | 2 | 2.10 | 3.67 | 3.11 | 1.08 | 1.88 |
| pMON116812 | T-Mt.Lhcb2-1:2:1 | 13 | 1.56 | 2.43 | 2.43 | 1.21 | 4.02 |
| pMON116813 | T-Mt.PSII-T B-1:2:1 | 21 | 2.67 | 5.66 | 1.16 | 0.65 | 0.50 |
| pMON116815 | T-Mt.AC145767v28-1:1:2 | 1 | 7.48 | 24.12 | 14.67 | 5.33 | 5.59 |
| pMON116826 | T-Mt.Lox-1-1:2:1 | 14 | 5.86 | 11.69 | 3.43 | 6.62 | 3.37 |
| pMON116827 | T-Mt.Gpi-1:2:1 | 11 | 2.47 | 2.58 | 0.16 | 0.09 | 0.27 |
| pMON116830 | T-Mt.Scp-1:2:1 | 27 | 1.19 | 1.46 | 0.36 | 0.63 | 0.97 |
| pMON122850 | T-Mt.RpL3-1:2:1 | 25 | 5.54 | 9.90 | 0.85 | 1.12 | 2.61 |
| pMON122851 | T-Mt.RD22-1:2:1 | 24 | 2.00 | 3.83 | 1.80 | 2.41 | 0.71 |
| pMON122852 | T-Mt.Methm-1:2:1 | 15 | 3.21 | 6.48 | 0.79 | 1.58 | 5.12 |
| pMON122853 | T-Mt.Prx-1:1:1 | 19 | 0.97 | 2.96 | 0.57 | 0.83 | 1.02 |
| pMON122854 | T-Mt.Gapdh-1:2:1 | 10 | 3.45 | 3.24 | 0.99 | 1.07 | 2.43 |
| pMON122855 | T-Mt.FBA-1:1:5 | 8 | 3.60 | 7.71 | 1.65 | 1.14 | 3.02 |
| pMON122856 | T-Mt.Zfp-1:2:1 | 30 | 0.97 | 0.90 | 1.30 | 1.79 | 0.56 |
| pMON122857 | T-Mt.AC139600v16-1:2:1 | 3 | 2.98 | 4.93 | 0.68 | 1.42 | 4.46 |
| pMON122858 | T-Mt.MP21-1:2:1 | 16 | 2.13 | 5.28 | 2.04 | 1.54 | 1.67 |
| pMON122859 | T-Mt.Oxr-1:2:1 | 17 | 4.03 | 10.90 | 1.10 | 2.19 | 0.43 |
| pMON122861 | T-Mt.Apx-1:1:2 | 5 | 1.12 | 4.40 | 0.56 | 0.22 | 1.72 |
| pMON122862 | T-Mt.Sui1-1:1:2 | 29 | 4.09 | 10.16 | 0.92 | 0.31 | 4.94 |
| pMON122863 | T-Mt.EF1a-1:1:2 | 6 | 2.86 | 5.46 | 1.89 | 0.89 | 1.48 |
| pMON122864 | T-Mt.Pip1-1:2:1 | 18 | 2.93 | 4.45 | 1.29 | 0.92 | 1.01 |
| pMON122865 | T-Mt.AC153125V10-1:2:1 | 4 | 0.43 | 1.15 | | | 0.12 |
| pMON122866 | T-Mt.Sali3-2-1:2:1 | 26 | 2.64 | 6.76 | | | 0.59 |
| pMON122867 | T-Mt.Hsp20-1:2:1 | 12 | 2.85 | 4.90 | 1.14 | 1.17 | 0.72 |
| pMON122868 | T-Mt.Expr1-1:2:1 | 7 | 4.20 | 3.76 | 3.09 | 2.92 | 2.01 |

As demonstrated in Tables 8 and 9, expression in the tissues of transformed soybean plants comprising different *Medicago* 3' UTRs was distinct when compared to that of soybean plants transformed with pMON102167, which comprised a 3' UTR derived from *Gossypium barbadense*. For example, two *Medicago* 3' UTRs, T-Mt.AC145767v28-1:1:2 (SEQ ID NO: 1) and T-Mt.Lox-1-1:2:1 (SEQ ID NO: 14) caused enhanced expression of the constitutive EXP, EXP-CaMV.35S-enh+Ph.DnaK:1:3 (SEQ ID NO: 42), across all tissues. Other *Medicago* 3' UTRs provided enhanced expression of the constitutive EXP in some tissues, while reducing expression in others. For example, the 3' UTR T-Mt.Sali3-2-1:2:1 (SEQ ID NO: 26) provided a 2.19- to 8.05-fold increase in expression in the Vn5 Root, Vn5 Sink Leaf, Vn5 Source Leaf, R1 Source Leaf, Yellow Pod Embryo, and Yellow Pod Cotyledon, while reducing expression in the R1 Flower and R5 Cotyledon. Further, the 3' UTR T-Mt.AC140914v20-1:2:1 (SEQ ID NO: 2) provided a 1.88- to 4.12-fold increase in expression in Vn5 Root, Vn5 Sink Leaf, Vn5 Source Leaf, Yellow Pod Embryo, Yellow Pod Cotyledon, R3 Immature Seed, and R5 Cotyledon, while reducing expression in the R1 Source Leaf, R1 Flower, and keeping expression relatively the same in the R3 Pod. In addition, the 3' UTR T-Mt.Oxr-1:2:1 (SEQ ID NO: 17) provided a 2.19-to 10.90-fold increase in expression in Vn5 Root, Vn5 Sink Leaf, Vn5 Source Leaf, R1 Source Leaf, Yellow Pod Embryo, Yellow Pod Cotyledon, and R3 Pod, while reducing expression in the R1 Flower and R5 Cotyledon, and keeping expression relatively the same in R3 Immature Seed.

Some of the transformed soybean plants comprising different *Medicago* 3' UTRs were taken to the $R_1$ generation. Tables 10 and 11 show the mean GUS expression values of the assayed tissues. Tables 12 and 13 show the fold difference in expression relative to the 3'UTR derived from *Gossypium barbadense*.

TABLE 10

Mean GUS expression in $R_1$ generation transformed soybean plants in Vn5 Root, Vn5 Sink Leaf, Vn5 Source Leaf, R1 Source Leaf, R1 Petiole, and R1 Flower.

| Plasmid Construct | 3' UTR Description | SEQ ID NO: | Vn5 Root | Vn5 Sink Leaf | Vn5 Source Leaf | R1 Source Leaf | R1 Petiole | R1 Flower |
|---|---|---|---|---|---|---|---|---|
| pMON102167 | T-Gb.E6-3b:1:1 | 40 | 934.22 | 992.31 | 1210.30 | 856.01 | 570.64 | 603.61 |
| pMON116813 | T-Mt.PSII-T B-1:2:1 | 21 | 1462.92 | 1169.79 | 1495.65 | 1159.28 | 647.86 | 506.70 |
| pMON116815 | T-Mt.AC145767v28-1:1:2 | 1 | 5555.77 | 5146.48 | 4447.42 | 2654.13 | 2825.41 | 2584.82 |
| pMON122859 | T-Mt.Oxr-1:2:1 | 17 | 3726.08 | 3090.41 | 3862.55 | 2666.68 | 1160.66 | 1041.40 |
| pMON122866 | T-Mt.Sali3-2-1:2:1 | 26 | 3438.35 | 2856.04 | 2510.49 | 2012.63 | 1087.69 | 919.57 |

TABLE 11

Mean GUS expression in $R_1$ generation transformed soybean plants in Yellow Pod Embryo, Yellow Pod Cotyledon, R3 Immature Seed, R3 Pod and R5 Cotyledon.

| Plasmid Construct | 3' UTR Description | SEQ ID NO: | Yellow Pod Embryo | Yellow Pod Cotyledon | R3 Immature Seed | R3 Pod | R5 Cotyledon |
|---|---|---|---|---|---|---|---|
| pMON102167 | T-Gb.E6-3b:1:1 | 40 | 85.27 | 174.11 | 298.03 | 567.48 | 85.11 |
| pMON116813 | T-Mt.PSII-T B-1:2:1 | 21 | 468.66 | 537.77 | 171.00 | 976.84 | 342.29 |
| pMON116815 | T-Mt.AC145767v28-1:1:2 | 1 | 1314.44 | 2134.97 | 1039.30 | 4506.45 | 1842.61 |
| pMON122859 | T-Mt.Oxr-1:2:1 | 17 | 730.81 | 1098.62 | 245.45 | 1947.45 | 423.40 |
| pMON122866 | T-Mt.Sali3-2-1:2:1 | 26 | 686.08 | 988.27 | 488.62 | 1068.10 | 757.12 |

As demonstrated in Tables 10 and 11, expression driven by the same EXP was distinct in tissues of stably transformed soybean plants comprising different *Medicago* 3' UTRs when compared to the *Gossypium barbadense*-derived 3' UTR. Tables 12 and 13 show the fold expression differences in the tissues of stably transformed soybean plants comprising different *Medicago* 3' UTRs relative to tissues transformed with pMON102167, which comprised a 3' UTR derived from *Gossypium barbadense*.

TABLE 12

Fold expression differences in $R_1$ generation transformed soybean plants in Vn5 Root, Vn5 Sink Leaf, Vn5 Source Leaf, R1 Source Leaf, R1 Petiole, and R1.

| Plasmid Construct | 3' UTR Description | SEQ ID NO: | Vn5 Root | Vn5 Sink Leaf | Vn5 Source Leaf | R1 Source Leaf | R1 Petiole | R1 Flower |
|---|---|---|---|---|---|---|---|---|
| pMON102167 | T-Gb.E6-3b:1:1 | 40 | 1.00 | 1.00 | 1.00 | 1.00 | 1.00 | 1.00 |
| pMON116813 | T-Mt.PSII-T B-1:2:1 | 21 | 1.57 | 1.18 | 1.24 | 1.35 | 1.14 | 0.84 |
| pMON116815 | T-Mt.AC145767v28-1:1:2 | 1 | 5.95 | 5.19 | 3.67 | 3.10 | 4.95 | 4.28 |
| pMON122859 | T-Mt.Oxr-1:2:1 | 17 | 3.99 | 3.11 | 3.19 | 3.12 | 2.03 | 1.73 |
| pMON122866 | T-Mt.Sali3-2-1:2:1 | 26 | 3.68 | 2.88 | 2.07 | 2.35 | 1.91 | 1.52 |

TABLE 13

Fold expression differences in $R_1$ generation transformed soybean plants in Yellow Pod Embryo, Yellow Pod Cotyledon, R3 Immature Seed, R3 Pod and R5 Cotyledon.

| Plasmid Construct | 3' UTR Description | SEQ ID NO: | Yellow Pod Embryo | Yellow Pod Cotyledon | R3 Immature Seed | R3 Pod | R5 Cotyledon |
|---|---|---|---|---|---|---|---|
| pMON102167 | T-Gb.E6-3b:1:1 | 40 | 1.00 | 1.00 | 1.00 | 1.00 | 1.00 |
| pMON116813 | T-Mt.PSII-T B-1:2:1 | 21 | 5.50 | 3.09 | 0.57 | 1.72 | 4.02 |
| pMON116815 | T-Mt.AC145767v28-1:1:2 | 1 | 15.42 | 12.26 | 3.49 | 7.94 | 21.65 |
| pMON122859 | T-Mt.Oxr-1:2:1 | 17 | 8.57 | 6.31 | 0.82 | 3.43 | 4.97 |
| pMON122866 | T-Mt.Sali3-2-1:2:1 | 26 | 8.05 | 5.68 | 1.64 | 1.88 | 8.90 |

As demonstrated in Tables 12 and 13, several of the *Medicago* 3' UTRs enhanced expression of the constitutive EXP element, EXP-CaMV.35S-enh+Ph.DnaK:1:3 (SEQ ID NO: 42), relative to plants transformed with pMON102167, which comprised a 3' UTR derived from *Gossypium barbadense* in the $R_1$ generation. For example, the 3' UTR T-Mt.AC145767v28-1:1:2 (SEQ ID NO: 1) provided a 3.10- to 21.65-fold enhancement of GUS expression in all of the tissues assayed. The 3' UTR T-Mt.Sali3-2-1:2:1 (SEQ ID NO: 26) provided a 1.52- to 8.90-fold enhancement of GUS expression in all of the tissues assayed. The 3' UTR T-Mt.Oxr-1:2:1 (SEQ ID NO: 17) provided enhancement in most tissues, but reduced expression in the R3 Immature Seed relative to plants transformed with T-Gb.E6-3b:1:1 (SEQ ID NO: 40).

The forgoing experiments demonstrate that the *Medicago truncatula* derived 3' UTR elements affected expression of the constitutive EXP element EXP-CaMV.35S-enh+Ph-.DnaK:1:3 (SEQ ID NO: 42) in different ways depending upon the specific 3' UTR selected. In many cases, there was an enhancement of expression in certain tissues of plants transformed with plant expression vectors comprising a *Medicago* 3' UTRs relative to plants transformed with pMON102167, which comprised a 3' UTR derived from *Gossypium barbadense*. However, the enhancement effect was not seen in all plant tissues and, in many cases, expression was attenuated in some tissues and enhanced in others using a *Medicago* 3' UTR. Thus, the use of selected *Medicago* 3' UTRs allows for one to "fine tune" the expression profile of a particular transgene and can be used in combination with different expression elements, such as promoters, leaders and introns, in operable linkage with a transcribable DNA molecule to provide optimal expression in specific tissues, while reducing expression in tissues that are less desirable for a specific transcribable DNA molecule.

Example 4

Analysis of the Effect of 3' UTRs on Seed Preferred GUS Expression in Stably Transformed Soybean Plants Soybean plants were transformed with vectors, specifically plasmid constructs, to assess the effect of selected *Medicago* 3' UTRs on expression. Specifically, soybean plants were transformed with DNA vectors containing a seed expressing EXP sequence driving expression of the β-glucuronidase (GUS) transgene operably linked to a *Medicago* 3' UTR. These *Medicago* 3' UTR-transformed soybean plants were compared to transformed soybean plants in which expression of the GUS transgene was driven by a seed expressing EXP sequence and the GUS transgene was operably linked to 3' UTR derived from *Gossypium barbadense*.

The plant vectors utilized in these experiments were built using cloning methods known in the art. The resulting vectors comprised a left border region from *A. tumefaciens*; a first transgene expression cassette for selection of transformed plant cells that confers resistance to the antibiotic spectinomycin (driven by the *Arabidopsis* Actin 7 promoter); a second transgene expression cassette used to assess the activity of the 3' UTR, which comprised the EXP element, EXP-Gm.Sphas1:1:1 (SEQ ID NO: 50), which provides seed preferred expression, operably linked 5' to a coding sequence for GUS that possesses a processable intron (GUS-2, SEQ ID NO: 44), which is operably linked 5' to a 3' UTR derived from *Medicago truncatula* or *Gossypium barbadense*; and a right border region from *A. tumefaciens*. The plant expression vectors that comprised a 3' UTR derived from *Medicago* were pMON116832, pMON116834, pMON116835, pMON116841, pMON122869, pMON122870, pMON122871, pMON122872, pMON122873, pMON122874, pMON122875, pMON122876, pMON122878, pMON122879, pMON122880, pMON122881, pMON122882, pMON122883, pMON122885, pMON122887, pMON122888, and pMON126122. The vector that comprised a 3' UTR from *Gossypium barbadense* was pMON83028.

Table 14 provides the plasmid constructs with the corresponding 3' UTR, SEQ ID NO, and generation for which quantitative assay data is provided.

TABLE 14

Plasmid constructs used to transform soybean plants and corresponding 3' UTR.

| Plasmid Construct | 3' UTR Description | SEQ ID NO: | Generation For which Data is Provided |
|---|---|---|---|
| pMON83028 | T-Gb.E6-3b:1:1 | 40 | $R_1$ |
| pMON116832 | T-Mt.AC140914v20-1:2:1 | 2 | $R_0$ |
| pMON116834 | T-Mt.PSII-T_A-1:2:1 | 20 | $R_0$ |
| pMON116835 | T-Mt.AC145767v28-1:1:2 | 1 | $R_0$ |
| pMON116841 | T-Mt.PSII-T_B-1:2:1 | 21 | $R_0$ |
| pMON122869 | T-Mt.RpL3-1:2:1 | 25 | $R_0$ |
| pMON122870 | T-Mt.RD22-1:2:1 | 24 | $R_0$ |
| pMON122871 | T-Mt.Methm-1:2:1 | 15 | $R_0$ |
| pMON122872 | T-Mt.Prx-1:1:1 | 19 | $R_0$ |
| pMON122873 | T-Mt.Gapdh-1:2:1 | 10 | $R_0$ |
| pMON122874 | T-Mt.FBA-1:2:1 | 9 | $R_0$ |
| pMON122875 | T-Mt.Zfp-1:2:1 | 30 | $R_0$ and $R_1$ |
| pMON122876 | T-Mt.AC139600v16-1:1:2 | 3 | $R_0$ |
| pMON122878 | T-Mt.Oxr-1:2:1 | 17 | $R_0$ |
| pMON122879 | T-Mt.Apx-1:1:2 | 5 | $R_0$ and $R_1$ |
| pMON122880 | T-Mt.Sui1-1:1:2 | 29 | $R_0$ and $R_1$ |

TABLE 14-continued

Plasmid constructs used to transform soybean plants and corresponding 3' UTR.

| Plasmid Construct | 3' UTR Description | SEQ ID NO: | Generation For which Data is Provided |
|---|---|---|---|
| pMON122881 | T-Mt.EF1a-1:1:2 | 6 | $R_0$ and $R_1$ |
| pMON122882 | T-Mt.Pip1-1:2:1 | 18 | $R_0$ |
| pMON122883 | T-Mt.AC153125V10-1:2:1 | 4 | $R_0$ |
| pMON122885 | T-Mt.Expr1-1:2:1 | 7 | $R_0$ |
| pMON122887 | T-Mt.Pt1-1:2:2 | 22 | $R_0$ |
| pMON122888 | T-Mt.Pt2-1:2:2 | 23 | $R_0$ |
| pMON126122 | T-Mt.Expr1-1:2:1 | 7 | $R_0$ |

The soybean plants were transformed and GUS assayed as described in Example 3. Tables 15 and 16 provide the quantitative mean GUS values for the $R_0$ generation of stably transformed soybean plants.

TABLE 15

Mean GUS expression in $R_0$ generation of transformed soybean plants in Yellow Pod Embryo, Yellow Pod Cotyledon, R3 Immature Seed, R3 Pod, and R5 Cotyledon.

| 3'UTR Description | SEQ ID NO: | Yellow Pod Embryo | Yellow Pod Cotyledon | R3 Immature Seed | R3 Pod | R5 Cotyledon |
|---|---|---|---|---|---|---|
| T-Mt.AC140914v20-1:2:1 | 2 | 572 | 1045 | 9 | 6 | 8 |
| T-Mt.PSII-T_A-1:2:1 | 20 | 210 | 371 | 7 | 6 | 61 |
| T-Mt.AC145767v28-1:1:2 | 1 | 1445 | 4264 | 11 | 8 | 47 |
| T-Mt.PSII-T_B-1:2:1 | 21 | 218 | 774 | 15 | 16 | 60 |
| T-Mt.RpL3-1:2:1 | 25 | 683 | 1087 | | | |
| T-Mt.RD22-1:2:1 | 24 | 3164 | 6809 | 30 | 15 | 24 |
| T-Mt.Methm-1:2:1 | 15 | 459 | 2136 | 7 | 6 | 74 |
| T-Mt.Prx-1:1:1 | 19 | 109 | 794 | 9 | 6 | 42 |
| T-Mt.Gapdh-1:2:1 | 10 | 241 | 745 | 6 | 5 | |
| T-Mt.FBA-1:2:1 | 9 | 622 | 772 | 10 | 6 | 100 |
| T-Mt.Zfp-1:2:1 | 30 | 192 | 193 | 2 | 2 | 31 |
| T-Mt.AC139600v16-1:2:1 | 3 | 319 | 2150 | 8 | 6 | 157 |
| T-Mt.Oxr-1:2:1 | 17 | 995 | 3220 | 5 | 4 | 235 |
| T-Mt.Apx-1:1:2 | 5 | 41 | 272 | 10 | 9 | 10 |
| T-Mt.Sui1-1:1:2 | 29 | 120 | 546 | 15 | 116 | 16 |
| T-Mt.EF1a-1:1:2 | 6 | | | 10 | 9 | 17 |
| T-Mt.Pip1-1:2:1 | 18 | 670 | 614 | 8 | 9 | 5 |
| T-Mt.AC153125V10-1:2:1 | 4 | 2079 | 4192 | 8 | 6 | 62 |
| T-Mt.Expr1-1:2:1 | 7 | 385 | 1092 | 11 | 5 | 299 |
| T-Mt.Pt1-1:2:2 | 22 | 142 | 630 | 14 | 14 | 426 |
| T-Mt.Pt2-1:2:2 | 23 | 440 | 513 | 2 | 1 | 10 |
| T-Mt.Expr1-1:2:1 | 7 | 527 | 1122 | 15 | 6 | 154 |

TABLE 16

Mean GUS expression in $R_0$ generation transformed soybean plants in Vn5 Root, Vn5 Sink Leaf, Vn5 Source Leaf, R1 Source Leaf, R1 Petiole, and R1 Flower.

| 3' UTR Description | SEQ ID NO: | Vn5 Root | Vn5 Sink Leaf | Vn5 Source Leaf | R1 Source Leaf | R1 Petiole | R1 Flower |
|---|---|---|---|---|---|---|---|
| T-Mt.AC140914v20-1:2:1 | 2 | 23 | 4 | 6 | 4 | 4 | 4 |
| T-Mt.PSII-T_A-1:2:1 | 20 | 29 | 5 | 8 | 6 | 3 | 3 |
| T-Mt.AC145767v28-1:1:2 | 1 | 10 | 3 | 4 | 0 | 0 | 0 |
| T-Mt.PSII-T_B-1:2:1 | 21 | 8 | 5 | 5 | 5 | 5 | 6 |
| T-Mt.RpL3-1:2:1 | 25 | 60 | 26 | 22 | 7 | 8 | 9 |
| T-Mt.RD22-1:2:1 | 24 | 21 | 2 | 3 | 12 | 11 | 11 |
| T-Mt.Methm-1:2:1 | 15 | 8 | 4 | 4 | 0 | 0 | 0 |
| T-Mt.Prx-1:1:1 | 19 | 5 | 5 | 5 | 0 | 0 | 0 |
| T-Mt.Gapdh-1:2:1 | 10 | 20 | 8 | 6 | 8 | 6 | 8 |
| T-Mt.FBA-1:2:1 | 9 | 9 | 3 | 3 | 18 | 15 | 17 |
| T-Mt.Zfp-1:2:1 | 30 | 41 | 13 | 14 | 7 | 5 | 6 |
| T-Mt.AC139600v16-1:2:1 | 3 | 7 | 5 | 5 | 0 | 0 | 0 |
| T-Mt.Oxr-1:2:1 | 17 | 7 | 3 | 8 | 0 | 0 | 0 |
| T-Mt.Apx-1:1:2 | 5 | 31 | 16 | 19 | 1173 | 294 | 357 |
| T-Mt.Sui1-1:1:2 | 29 | 29 | 20 | 19 | 10 | 5 | 4 |
| T-Mt.EF1a-1:1:2 | 6 | 8 | 3 | 3 | 16 | 19 | 19 |
| T-Mt.Pip1-1:2:1 | 18 | 15 | 7 | 6 | 8 | 4 | 3 |
| T-Mt.AC153125V10-1:2:1 | 4 | 16 | 5 | 3 | 0 | 0 | 0 |
| T-Mt.Expr1-1:2:1 | 7 | 22 | 8 | 10 | 6 | 3 | 3 |
| T-Mt.Pt1-1:2:2 | 22 | 8 | 6 | 5 | 5 | 6 | 6 |

TABLE 16-continued

Mean GUS expression in R₀ generation transformed soybean plants in Vn5 Root,
Vn5 Sink Leaf, Vn5 Source Leaf, R1 Source Leaf, R1 Petiole, and R1 Flower.

| 3' UTR Description | SEQ ID NO: | Vn5 Root | Vn5 Sink Leaf | Vn5 Source Leaf | R1 Source Leaf | R1 Petiole | R1 Flower |
|---|---|---|---|---|---|---|---|
| T-Mt.Pt2-1:2:2 | 23 | 34 | 11 | 11 | 6 | 6 | 6 |
| T-Mt.Expr1-1:2:1 | 7 | 15 | 6 | 8 | 5 | 4 | 4 |

As can be seen in Tables 15 and 16, most of the *Medicago* 3' UTRs affected expression of the seed preferred EXP element, EXP-Gm.Sphas1:1:1 (SEQ ID NO: 50), in only seed-derived tissues, with the exception of T-Mt.Apx-1:1:2 (SEQ ID NO: 5), which enhanced expression of GUS in the R1 Source Leaf, R1 Petiole, and R1 Flower. Several *Medicago* 3' UTRs provided high expression in the Yellow Pod Embryo and Yellow Pod Cotyledon, such as T-Mt.AC145767v28-1:1:2 (SEQ ID NO: 1), T-Mt.RD22-1:2:1 (SEQ ID NO: 24), and T-Mt.AC153125V10-1:2:1 (SEQ ID NO: 4). Thus, these 3' UTRs may be ideal to enhance expression of a seed promoter during the later stages of seed development. The 3' UTR T-Mt.Expr1-1:2:1 (SEQ ID NO: 7) provided high expression in both R5 Cotyledon and Yellow Pod Cotyledon relative to many of the other 3' UTRs, and thus may be useful in providing high cotyledon expression for a wider window of seed development. In some cases, the 3' UTR provided a more uniform level of seed expression both in the Yellow Pod Embryo and Yellow Pod Cotyledon, such as when T-Mt.FBA-1:2:1 (SEQ ID NO: 9), T-Mt.Zfp-1:2:1 (SEQ ID NO: 30), T-Mt.Pip1-1:2:1 (SEQ ID NO: 18), and T-Mt.Pt2-1:2:2 (SEQ ID NO: 23) were used.

The R₀ generation plants comprising T-Mt.Zfp-1:2:1 (SEQ ID NO: 30), T-Mt.Apx-1:1:2 (SEQ ID NO: 5), T-Mt.Sui1-1:1:2 (SEQ ID NO: 29), and T-Mt.EF1a-1:1:2 (SEQ ID NO: 6) were allowed to set seed and were planted for R₁ generation studies. Table 17 shows a comparison of the mean quantitative assay data for events comprising these R₁ generation plants comprising *Medicago* 3' UTRs and plants transformed with pMON83028, which comprised the 3' UTR T-Gb.E6-3b:1:1 (SEQ ID NO: 40) derived from *Gossypium barbadense*.

TABLE 17

Mean GUS expression in R₁ generation transformed soybean plants
in Yellow Pod Embryo, Yellow Pod Cotyledon, and R5 Cotyledon.

| Plasmid Construct | 3' UTR Description | SEQ ID NO: | Yellow Pod Embryo | Yellow Pod Cotyledon | R5 Cotyledon |
|---|---|---|---|---|---|
| pMON83028 | T-Gb.E6-3b:1:1 | 40 | 102 | 362 | 7 |
| pMON122875 | T-Mt.Zfp-1:2:1 | 30 | 56 | 153 | 498 |
| pMON122879 | T-Mt.Apx-1:1:2 | 5 | 205 | 645 | 777 |
| pMON122880 | T-Mt.Sui1-1:1:2 | 29 | 462 | 1241 | 355 |
| pMON122881 | T-Mt.EF1a-1:1:2 | 6 | 415 | 1059 | 11 |

As can be seen in Table 17, the *Medicago* 3' UTRs affected expression differently than T-Gb.E6-3b:1:1 in the embryo and cotyledon tissues. For example, T-Mt.Apx-1:1:2 (SEQ ID NO: 5) and T-Mt.Sui1-1:1:2 (SEQ ID NO: 29) enhanced expression of the seed-preferred EXP element in the Yellow Pod Embryo, Yellow Pod Cotyledon, and R5 Cotyledon relative to T-Gb.E6-3b:1:1. T-Mt.EF1a-1:1:2 (SEQ ID NO: 6) enhanced expression in the Yellow Pod Embryo and Yellow Pod Cotyledon, but not in the R5 Cotyledon. T-Mt.Zfp-1:2:1 (SEQ ID NO: 30) reduced expression in the later developing Yellow Pod Embryo and Yellow Pod Cotyledon, but enhanced expression in the R5 Cotyledon.

Thus, each of the different *Medicago* 3' UTRs affect expression differentially in the developing seed when in operable linkage with a seed preferred promoter. These differences in the effect on expression can be utilized to provide a more refined and tailored approach to seed expression and may be ideally suited for "fine tuning" the expression profile of specific transcribable DNA molecules where seed expression is desired.

Example 5

Analysis of the Effect of 3' UTRs on Constitutive GUS Expression in Stably Transformed Soybean Plants Soybean plants were transformed with vectors, specifically plasmid constructs, to assess the effect of selected *Medicago truncatula* 3' UTRs on expression. Specifically, soybean plants were transformed with vectors containing two different EXP elements that exhibit a constitutive expression profile driving expression of the β-glucuronidase (GUS) transgene operably linked to a *Medicago* 3' UTR. These *Medicago* 3' UTR-transformed plants were compared to transformed soybean plants in which expression of the GUS transgene was operably linked to a 3' UTR derived from *Gossypium barbadense*.

The plant vectors utilized in these experiments were built using cloning methods known in the art. The resulting vectors comprised a left border region from *A. tumefaciens*; a first transgene expression cassette for selection of transformed plant cells that confers resistance to the antibiotic spectinomycin (driven by the *Arabidopsis* Actin 7 promoter); a second transgene expression cassette used to assess the activity of the 3' UTR, which comprised the EXP elements EXP-CaMV.35S-enh+Ph.DnaK:1:3 (SEQ ID NO: 42) or EXP-DaMV.FLT:1:2 (SEQ ID NO: 51) operably linked 5' to a coding sequence for GUS that possesses a processable intron (GUS-2, SEQ ID NO: 44), which is operably linked 5' to a 3' UTR derived from *Medicago* truncatula or Gossypium barbadense; and a right border region from A. tumefaciens. The vectors that comprised a 3' UTR derived from Medicago were pMON118768, pMON153701 and pMON116803. The vectors that comprised a 3' UTR from Gossypium barbadense were pMON121042 and pMON102167.

Table 18 provides the plasmid constructs with the corresponding EXP element, 3' UTR and SEQ ID NO used to transform the soybean plants presented in this Example.

TABLE 18

Plasmid constructs used to transform soybean plants and the corresponding EXP element and 3' UTR.

| Plasmid Construct | EXP Description | EXP SEQ ID NO: | 3' UTR Description | 3' UTR SEQ ID NO: |
|---|---|---|---|---|
| pMON121042 | EXP-DaMV.FLT:1:2 | 51 | T-Gb.E6-3b:1:1 | 40 |
| pMON118768 | EXP-DaMV.FLT:1:2 | 51 | T-Mt.Sali3-2-1:2:1 | 26 |
| pMON153701 | EXP-DaMV.FLT:1:2 | 51 | T-Mt.AC140914v20-1:2:1 | 2 |
| pMON102167 | EXP-CaMV.35S-enh + Ph.DnaK:1:3 | 42 | T-Gb.E6-3b:1:1 | 40 |
| pMON122866 | EXP-CaMV.35S-enh + Ph.DnaK:1:3 | 42 | T-Mt.Sali3-2-1:2:1 | 26 |
| pMON116803 | EXP-CaMV.35S-enh + Ph.DnaK:1:3 | 42 | T-Mt.AC140914v20-1:2:1 | 2 |

Plants were transformed and GUS assayed as described in Example 3. Tables 19 and 20 provide the quantitative mean GUS values for the $R_0$ generation of stably transformed soybean plants.

As demonstrated in Tables 19 and 20, the Medicago 3' UTRs T-Mt.Sali3-2-1:2:1 (SEQ ID NO: 26) and T-Mt.AC140914v20-1:2:1 (SEQ ID NO: 2) affected expression of the constitutive EXP element EXP-DaMV.FLT:1:2 (SEQ ID NO: 51) differently than the Gossypium barbadense-derived 3' UTR T-Gb.E6-3b:1:1 (SEQ ID NO: 40). In many of the sampled tissues, there was an enhancement of expression using the Medicago 3' UTRs. With respect to the 3' UTR T-Mt.AC140914v20-1:2:1, enhancement was seen in most tissues in plants also comprising the EXP element EXP-CaMV.35S-enh+Ph.DnaK:1:3 (SEQ ID NO: 42). Tables 21 and 22 show the fold differences of the quantitative GUS expression relative to the expression

TABLE 19

Mean GUS expression in $R_0$ generation transformed soybean plants in Vn5 Root, Vn5 Sink Leaf, Vn5 Source Leaf, R1 Source Leaf, R1 Petiole, and R1 Flower.

| EXP Description | 3' UTR Description | Vn5 Root | Vn5 Sink Leaf | Vn5 Source Leaf | R1 Source Leaf | R1 Petiole | R1 Flower |
|---|---|---|---|---|---|---|---|
| EXP-DaMV.FLT:1:2 | T-Gb.E6-3b:1:1 | 780.79 | 688.93 | 509.35 | 320.02 | 379.69 | 467.94 |
| EXP-DaMV.FLT:1:2 | T-Mt.Sali3-2-1:2:1 | 4782.43 | 1009.59 | 1208.48 | 363.55 | 1425.76 | 1398.80 |
| EXP-DaMV.FLT:1:2 | T-Mt.AC140914v20-1:2:1 | 3792.66 | 725.38 | 1106.9 | 1831.99 | 4792.28 | 739.97 |
| EXP-CaMV.35S-enh+Ph.DnaK:1:3 | T-Gb.E6-3b:1:1 | 400.90 | 551.61 | 605.29 | 350.93 | | 412.30 |
| EXP-CaMV.35S-enh+Ph.DnaK:1:3 | T-Mt.Sali3-2-1:2:1 | 2274.70 | 1176.10 | 1490.54 | 976.91 | 753.02 | 45.26 |
| EXP-CaMV.35S-enh+Ph.DnaK:1:3 | T-Mt.AC140914v20-1:2:1 | 1306.76 | 2269.95 | 2187.61 | 344.78 | 480.47 | 243.11 |

TABLE 20

Mean GUS expression in $R_0$ generation transformed soybean plants in Yellow Pod Embryo, Yellow Pod Cotyledon, R3 Immature Seed, R3 Pod and R5 Cotyledon.

| EXP Description | 3' UTR Description | Yellow Pod Embryo | Yellow Pod Cotyledon | R3 Immature Seed | R3 Pod | R5 Cotyledon |
|---|---|---|---|---|---|---|
| EXP-DaMV.FLT:1:2 | T-Gb.E6-3b:1:1 | 104.58 | 115.16 | 340.02 | 859.14 | 64.18 |
| EXP-DaMV.FLT:1:2 | T-Mt.Sali3-2-1:2:1 | 1582.51 | 832.99 | 84.88 | 1157.18 | 247.75 |
| EXP-DaMV.FLT:1:2 | T-Mt.AC140914v20-1:2:1 | 961.14 | 1050.82 | 456.55 | 2455.53 | 861.1 |
| EXP-CaMV.35S-enh+Ph.DnaK:1:3 | T-Gb.E6-3b:1:1 | 47.86 | 49.45 | 67.45 | 433.54 | 101.34 |
| EXP-CaMV.35S-enh+Ph.DnaK:1:3 | T-Mt.Sali3-2-1:2:1 | 126.53 | 334.27 | | | 59.33 |
| EXP-CaMV.35S-enh+Ph.DnaK:1:3 | T-Mt.AC140914v20-1:2:1 | 100.42 | 181.62 | 209.92 | 467.72 | 190.51 | imparted by pMON121042 (T-Gb.E6-3b:1:1 (SEQ ID NO: 40)), which comprises a 3' UTR derived from *Gossypium barbadense*.

Yellow Pod Cotyledon, but reduced expression in the R1 Flower and R5 Cotyledon relative to T-Gb.E6-3b:1:1 (SEQ ID NO: 40).

TABLE 21

Fold expression differences in $R_1$ generation transformed soybean plants in Vn5 Root, Vn5 Sink Leaf, Vn5 Source Leaf, R1 Source Leaf, R1 Petiole and R1 Flower.

| EXP Description | 3' UTR Description | Vn5 Root | Vn5 Sink Leaf | Vn5 Source Leaf | R1 Source Leaf | R1 Petiole | R1 Flower |
|---|---|---|---|---|---|---|---|
| EXP-DaMV.FLT:1:2 | T-Gb.E6-3b:1:1 | 1.00 | 1.00 | 1.00 | 1.00 | 1.00 | 1.00 |
| EXP-DaMV.FLT:1:2 | T-Mt.Sali3-2-1:2:1 | 6.13 | 1.47 | 2.37 | 1.14 | 3.76 | 2.99 |
| EXP-DaMV.FLT:1:2 | T-Mt.AC140914v20-1:2:1 | 4.86 | 1.05 | 2.17 | 5.72 | 12.62 | 1.58 |
| EXP-CaMV.35S-enh+Ph.DnaK:1:3 | T-Gb.E6-3b:1:1 | 1.00 | 1.00 | 1.00 | 1.00 | | 1.00 |
| EXP-CaMV.35S-enh+Ph.DnaK:1:3 | T-Mt.Sali3-2-1:2:1 | 5.67 | 2.13 | 2.46 | 2.78 | | 0.11 |
| EXP-CaMV.35S-enh+Ph.DnaK:1:3 | T-Mt.AC140914v20-1:2:1 | 3.26 | 4.12 | 3.61 | 0.98 | | 0.59 |

TABLE 22

Fold expression differences in $R_1$ generation transformed soybean plants in Yellow Pod Embryo, Yellow Pod Cotyledon, R3 Immature Seed, R3 Pod and R5 Cotyledon.

| EXP Description | 3' UTR Description | Yellow Pod Embryo | Yellow Pod Cotyledon | R3 Immature Seed | R3 Pod | R5 Cotyledon |
|---|---|---|---|---|---|---|
| EXP-DaMV.FLT:1:2 | T-Gb.E6-3b:1:1 | 1.00 | 1.00 | 1.00 | 1.00 | 1.00 |
| EXP-DaMV.FLT:1:2 | T-Mt.Sali3-2-1:2:1 | 15.13 | 7.23 | 0.25 | 1.35 | 3.86 |
| EXP-DaMV.FLT:1:2 | T-Mt.AC140914v20-1:2:1 | 9.19 | 9.13 | 1.34 | 2.86 | 13.42 |
| EXP-CaMV.35S-enh+Ph.DnaK:1:3 | T-Gb.E6-3b:1:1 | 1.00 | 1.00 | 1.00 | 1.00 | 1.00 |
| EXP-CaMV.35S-enh+Ph.DnaK:1:3 | T-Mt.Sali3-2-1:2:1 | 2.64 | 6.76 | | | 0.59 |
| EXP-CaMV.35S-enh+Ph.DnaK:1:3 | T-Mt.AC140914v20-1:2:1 | 2.10 | 3.67 | 3.11 | 1.08 | 1.88 |

The forgoing experiments demonstrate that each of the *Medicago* 3' UTRs has different effects upon the level of expression of each of the constitutive EXP elements relative to pMON121042 (T-Gb.E6-3b:1:1 (SEQ ID NO: 40)), which comprises the 3' UTR derived from *Gossypium barbadense*. For example, expression of EXP-DaMV.FLT:1:2 was enhanced 1.14-to 15.13-fold in Vn5 Root, Vn5 Sink Leaf, Vn5 Source Leaf, R1 Source Leaf, R1 Petiole, R1 Flower, Yellow Pod Embryo, Yellow Pod Cotyledon, R3 Pod, and R5 Cotyledon, but reduced in the R3 Immature Seed using T-Mt.Sali3-2-1:2:1. This same EXP element, when combined with T-Mt.AC140914v20-1:2:1, resulted in a 1.34- to 13.42-fold enhancement in Vn5 Root, Vn5 Source Leaf, R1 Source Leaf, R1 Petiole, R1 Flower, Yellow Pod Embryo, Yellow Pod Cotyledon, R3 Immature Seed, R3 Pod, and R5 Cotyledon, but remained about the same as T-Gb.E6-3b:1:1 (SEQ ID NO: 40) in the V5 Sink Leaf. Expression in Yellow Pod Embryo was about twice that of Yellow Pod Cotyledon using T-Mt.Sali3-2-1:2:1 (15.13- vs. 7.23-fold enhancement), while expression in these two tissues was relatively the same when using T-Mt.AC140914v20-1:2:1 (9.19- vs. 9.13-fold enhancement). With respect to the EXP element EXP-CaMV.35S-enh+Ph.DnaK:1:3, combination with T-Mt.AC140914v20-1:2:1 produced less enhancement in many of the sampled tissues than when this same 3' UTR was combined with EXP-DaMV.FLT:1:2. In R1 Flower, there was a reduction of expression relative to T-Gb.E6-3b:1:1 when EXP-CaMV.35S-enh+Ph.DnaK:1:3 was combined with T-Mt.AC140914v20-1:2:1. The combination of EXP-CaMV.35S-enh+Ph.DnaK:1:3 with T-Mt.Sali3-2-1:2:1 provided enhancement in Vn5 Root, Vn5 Sink Leaf, Vn5 Source Leaf, R1 Source Leaf, Yellow Pod Embryo, and Yellow Pod Cotyledon, but reduced expression in the R1 Flower and R5 Cotyledon relative to T-Gb.E6-3b:1:1 (SEQ ID NO: 40).

Each of the two *Medicago* 3' UTRs, T-Mt.Sali3-2-1:2:1 and T-Mt.AC140914v20-1:2:1, affected the expression of the two different constitutive EXP elements, EXP-DaMV-.FLT:1:2 and EXP-CaMV.35S-enh+Ph.DnaK:1:3, differently. In many tissues, there was an enhancement of expression relative to T-Gb.E6-3b:1:1 (SEQ ID NO: 40), but in some tissues, a reduction of expression occurred. Thus, by using different *Medicago* 3' UTRs, one may be able to more precisely control expression in the plant and better "fine tune" the expression of specific transcribable DNA molecules to provide optimal expression where the expression of the transcribable DNA molecule is required, while reducing expression in tissues that might negatively affect the plant.

Example 6

The *Medicago truncatula* 3' UTR T-Mt.AC145767v28-1:1:2 Causes Enhancement of GUS Expression when Combined with Many Different EXP Elements in Stably Transformed Soybean Plants Soybean plants were transformed with vectors, specifically plasmid constructs, to assess the effect of the *Medicago* 3' UTR T-Mt.AC145767v28-1:1:2 (SEQ ID NO: 1) on expression. Specifically, the soybean plants were transformed with vectors containing several different EXPs with a constitutive expression profile driving expression of the β-glucuronidase (GUS) transgene operably linked to the *Medicago* 3' UTR T-Mt.AC145767v28-1:1:2 (SEQ ID NO: 1). These *Medicago* 3' UTR-transformed soybean plants were compared to transformed soybean plants in which the GUS transgene was operably linked to a 3' UTR derived from *Gossypium barbadense*.

The vectors utilized in these experiments were built using cloning methods known in the art. The resulting vectors comprised a left border region from *A. tumefaciens*; a first transgene expression cassette for selection of transformed plant cells that confers resistance to the antibiotic spectinomycin (driven by the *Arabidopsis* Actin 7 promoter); a second transgene expression cassette used to assess the activity of the 3' UTR T-Mt.AC145767v28-1:1:2 (SEQ ID NO: 1) which comprises the EXP elements, EXP-Mt.AC145767v28:1:1 (SEQ ID NO: 35), EXP-CaMV.35S-enh+Ph.DnaK:1:3 (SEQ ID NO: 42), EXP-BSAcVNV.FLT:1:2 (SEQ ID NO: 52), EXP-CERV.FLT:1:2 (SEQ ID NO: 53), EXP-DaMV.FLT:1:2 (SEQ ID NO: 51), EXP-CUCme.eEF1a:1:1 (SEQ ID NO: 54), or EXP-Mt.Ubq2:1:2 (SEQ ID NO: 31) operably linked 5' to a coding sequence for GUS that possesses a processable intron (GUS-2, SEQ ID NO: 44) which is operably linked 5' to the 3' UTR T-Mt.AC145767v28-1:1:2 (SEQ ID NO: 1) derived from *Medicago truncatula*, or to the 3'UTRs T-Gb.E6-3b:1:1 (SEQ ID NO: 40) or T-Gb.FbL2-1:1:1 (SEQ ID NO: 41) derived from *Gossypium barbadense*; and a right border region from *A. tumefaciens*. The vectors that comprised T-Mt.AC145767v28-1:1:2 (SEQ ID NO: 1) were pMON118798, pMON116815, pMON118769, pMON153709, pMON118771, pMON153707, and pMON155502. Notably, vector pMON118798 comprised the native EXP-Mt.AC145767v28:1:1 which is comprised of a promoter element operably linked to a leader element cloned from the same gene locus as the 3' UTR T-Mt.AC145767v28-1:1:2 (SEQ ID NO: 1). The vectors that comprised the 3'UTR from *Gossypium barbadense* were pMON102167, pMON113874, pMON121030, pMON121042, pMON140827, and pMON125841.

Table 23 provides the plasmid constructs with the corresponding EXP element, 3' UTR, and SEQ ID NO used to transform the soybean plants presented in this Example.

TABLE 23

Plasmid constructs used to transform soybean plants and the corresponding EXP element and 3' UTR.

| Plasmid Construct | EXP Description | EXP SEQ ID NO: | 3' UTR Description | 3' UTR SEQ ID NO: |
|---|---|---|---|---|
| pMON118798 | EXP-Mt.AC145767v28:1:1 | 35 | T-Mt.AC145767v28-1:1:2 | 1 |
| pMON102167 | EXP-CaMV.35S-enh + Ph.DnaK:1:3 | 42 | T-Gb.E6-3b:1:1 | 40 |
| pMON116815 | EXP-CaMV.35S-enh + Ph.DnaK:1:3 | 42 | T-Mt.AC145767v28-1:1:2 | 1 |
| pMON113874 | EXP-BSAcVNV.FLT:1:2 | 52 | T-Gb.E6-3b:1:1 | 40 |
| pMON118769 | EXP-BSAcVNV.FLT:1:2 | 52 | T-Mt.AC145767v28-1:1:2 | 1 |
| pMON121030 | EXP-CERV.FLT:1:2 | 53 | T-Gb.E6-3b:1:1 | 40 |
| pMON153709 | EXP-CERV.FLT:1:2 | 53 | T-Mt.AC145767v28-1:1:2 | 1 |
| pMON121042 | EXP-DaMV.FLT:1:2 | 51 | T-Gb.E6-3b:1:1 | 40 |
| pMON118771 | EXP-DaMV.FLT:1:2 | 51 | T-Mt.AC145767v28-1:1:2 | 1 |
| pMON140827 | EXP-CUCme.eEF1a:1:1 | 54 | T-Gb.FbL2-1:1:1 | 41 |
| pMON153707 | EXP-CUCme.eEF1a:1:1 | 54 | T-Mt.AC145767v28-1:1:2 | 1 |
| pMON125841 | EXP-Mt.Ubq2:1:2 | 31 | T-Gb.FbL2-1:1:1 | 41 |
| pMON155502 | EXP-Mt.Ubq2:1:2 | 31 | T-Mt.AC145767v28-1:1:2 | 1 |

The soybean plants were transformed and GUS assayed as described in Example 3. Tables 24 and 25 provide the quantitative mean GUS values for the $R_0$ generation of stably transformed soybean plants. Table cells marked as "bdl" indicate tissues that were quantitatively analyzed but in which expression was below the level of detection. Tables 26 and 27 provide the fold changes in expression of each EXP element operably linked to T-Mt.AC145767v28-1:1:2 relative to T-Gb.E6-3b:1:1(SEQ ID NO: 40).

TABLE 24

Mean GUS expression in $R_0$ generation transformed soybean plants in Vn5 Root, Vn5 Sink Leaf, Vn5 Source Leaf, R1 Source Leaf, R1 Petiole and R1 Flower.

| EXP Description | 3' UTR Description | Vn5 Root | R1 Root | Vn5 Sink Leaf | Vn5 Source Leaf | R1 Source Leaf | R1 Petiole | R1 Flower |
|---|---|---|---|---|---|---|---|---|
| EXP-Mt.AC145767v28:1:1 | T-Mt.AC145767v28-1:1:2 | 59.00 | 71.00 | 32.00 | 34.00 | 33.00 | 23.00 | bdl |
| EXP-CaMV.35S-enh+Ph.DnaK:1:3 | T-Gb.E6-3b:1:1 | 400.90 | 618.03 | 551.61 | 605.29 | 350.93 | | 412.30 |
| EXP-CaMV.35S-enh+Ph.DnaK:1:3 | T-Mt.AC145767v28-1:1:2 | 3817.28 | | 1939.40 | 3250.38 | 1393.65 | 1001.37 | 876.08 |
| EXP-BSAcVNV.FLT:1:2 | T-Gb.E6-3b:1:1 | 111.12 | | 19.96 | 19.46 | 17.47 | 88.14 | 64.38 |
| EXP-BSAcVNV.FLT:1:2 | T-Mt.AC145767v28-1:1:2 | 6514.58 | 1081.72 | 477.98 | 419.52 | 227.72 | 1380.90 | 581.97 |
| EXP-CERV.FLT:1:2 | T-Gb.E6-3b:1:1 | 378.02 | | 344.15 | 480.25 | 177.64 | 285.15 | 130.87 |
| EXP-CERV.FLT:1:2 | T-Mt.AC145767v28-1:1:2 | 6711.26 | | 1618.72 | 3262.73 | 2995.09 | 5071.90 | 3608.75 |
| EXP-DaMV.FLT:1:2 | T-Gb.E6-3b:1:1 | 780.79 | | 688.93 | 509.35 | 320.02 | 379.69 | 467.94 |
| EXP-DaMV.FLT:1:2 | T-Mt.AC145767v28-1:1:2 | 9322.50 | 3655.79 | 5870.15 | 3923.47 | 2313.08 | 3610.84 | 2131.16 |
| EXP-CUCme.eEF1a:1:1 | T-Gb.FbL2-1:1:1 | 189.24 | 153.52 | 59.60 | 37.44 | 103.01 | 130.60 | 130.38 |
| EXP-CUCme.eEF1a:1:1 | T-Mt.AC145767v28-1:1:2 | 2300.06 | | 160.99 | 216.21 | 744.44 | 1628.65 | 405.97 |
| EXP-Mt.Ubq2:1:2 | T-Gb.FbL2-1:1:1 | 800.93 | | 202.73 | 275.48 | 143.60 | 1195.97 | 482.13 |
| EXP-Mt.Ubq2:1:2 | T-Mt.AC145767v28-1:1:2 | 855.00 | | 293.68 | 1118.76 | 254.25 | 875.67 | 398.10 |

TABLE 25

Mean GUS expression in R₀ generation transformed soybean plants in Yellow Pod Embryo, Yellow Pod Cotyledon, R3 Immature Seed, R3 Pod and R5 Cotyledon.

| EXP Description | 3' UTR Description | Yellow Pod Embryo | Yellow Pod Cotyledon | R3 Immature Seed | R3 Pod | R5 Cotyledon |
|---|---|---|---|---|---|---|
| EXP-Mt.AC145767v28:1:1 | T-Mt.AC145767v28-1:1:2 | 31.00 | 27.00 | bdl | bdl | 26.00 |
| EXP-CaMV.35S-enh+Ph.DnaK:1:3 | T-Gb.E6-3b:1:1 | 47.86 | 49.45 | 67.45 | 433.54 | 101.34 |
| EXP-CaMV.35S-enh+Ph.DnaK:1:3 | T-Mt.AC145767v28-1:1:2 | 358.03 | 1192.69 | 989.47 | 2309.72 | 566.93 |
| EXP-BSAcVNV.FLT:1:2 | T-Gb.E6-3b:1:1 | 28.31 | 62.63 | 24.08 | 115.00 | 11.35 |
| EXP-BSAcVNV.FLT:1:2 | T-Mt.AC145767v28-1:1:2 | 547.47 | 207.69 | 128.15 | 927.48 | 65.67 |
| EXP-CERV.FLT:1:2 | T-Gb.E6-3b:1:1 | 68.57 | 70.12 | 64.42 | 264.62 | 34.43 |
| EXP-CERV.FLT:1:2 | T-Mt.AC145767v28-1:1:2 | 1474.35 | 4242.09 | 2441.01 | 7209.69 | 900.82 |
| EXP-DaMV.FLT:1:2 | T-Gb.E6-3b:1:1 | 104.58 | 115.16 | 340.02 | 859.14 | 64.18 |
| EXP-DaMV.FLT:1:2 | T-Mt.AC145767v28-1:1:2 | 2806.65 | 1814.87 | 518.90 | 3720.59 | 401.66 |
| EXP-CUCme.eEF1a:1:1 | T-Gb.FbL2-1:1:1 | 200.28 | 291.26 | 58.21 | 131.17 | 114.29 |
| EXP-CUCme.eEF1a:1:1 | T-Mt.AC145767v28-1:1:2 | 1029.69 | 1883.48 | 209.77 | 1122.51 | 521.64 |
| EXP-Mt.Ubq2:1:2 | T-Gb.FbL2-1:1:1 | 129.84 | 83.45 | 400.15 | 875.75 | 72.66 |
| EXP-Mt.Ubq2:1:2 | T-Mt.AC145767v28-1:1:2 | | | 247.18 | 1324.98 | 352.81 |

TABLE 26

Fold expression differences in R₁ generation transformed soybean plants in Vn5 Root, Vn5 Sink Leaf, Vn5 Source Leaf, R1 Source Leaf, R1 Petiole and R1 Flower.

| EXP Description | 3' UTR Description | Vn5 Root | Vn5 Sink Leaf | Vn5 Source Leaf | R1 Source Leaf | R1 Petiole | R1 Flower |
|---|---|---|---|---|---|---|---|
| EXP-CaMV.35S-enh+Ph.DnaK:1:3 | T-Gb.E6-3b:1:1 | 1.00 | 1.00 | 1.00 | 1.00 | | 1.00 |
| EXP-CaMV.35S-enh+Ph.DnaK:1:3 | T-Mt.AC145767v28-1:1:2 | 9.52 | 3.52 | 5.37 | 3.97 | | 2.12 |
| EXP-BSAcVNV.FLT:1:2 | T-Gb.E6-3b:1:1 | 1.00 | 1.00 | 1.00 | 1.00 | 1.00 | 1.00 |
| EXP-BSAcVNV.FLT:1:2 | T-Mt.AC145767v28-1:1:2 | 58.63 | 23.94 | 21.56 | 13.03 | 15.67 | 9.04 |
| EXP-CERV.FLT:1:2 | T-Gb.E6-3b:1:1 | 1.00 | 1.00 | 1.00 | 1.00 | 1.00 | 1.00 |
| EXP-CERV.FLT:1:2 | T-Mt.AC145767v28-1:1:2 | 17.75 | 4.70 | 6.79 | 16.86 | 17.79 | 27.57 |
| EXP-DaMV.FLT:1:2 | T-Gb.E6-3b:1:1 | 1.00 | 1.00 | 1.00 | 1.00 | 1.00 | 1.00 |
| EXP-DaMV.FLT:1:2 | T-Mt.AC145767v28-1:1:2 | 11.94 | 8.52 | 7.70 | 7.23 | 9.51 | 4.55 |
| EXP-CUCme.eEF1a:1:1 | T-Gb.FbL2-1:1:1 | 1.00 | 1.00 | 1.00 | 1.00 | 1.00 | 1.00 |
| EXP-CUCme.eEF1a:1:1 | T-Mt.AC145767v28-1:1:2 | 12.15 | 2.70 | 5.77 | 7.23 | 12.47 | 3.11 |
| EXP-Mt.Ubq2:1:2 | T-Gb.FbL2-1:1:1 | 1.00 | 1.00 | 1.00 | 1.00 | 1.00 | 1.00 |
| EXP-Mt.Ubq2:1:2 | T-Mt.AC145767v28-1:1:2 | 1.07 | 1.45 | 4.06 | 1.77 | 0.73 | 0.83 |

TABLE 27

Fold expression differences in R₁ generation transformed soybean plants in Yellow Pod Embryo, Yellow Pod Cotyledon, R3 Immature Seed, R3 Pod and R5 Cotyledon.

| EXP Description | 3' UTR Description | Yellow Pod Embryo | Yellow Pod Cotyledon | R3 Immature Seed | R3 Pod | R5 Cotyledon |
|---|---|---|---|---|---|---|
| EXP-CaMV.35S-enh+Ph.DnaK:1:3 | T-Gb.E6-3b:1:1 | 1.00 | 1.00 | 1.00 | 1.00 | 1.00 |
| EXP-CaMV.35S-enh+Ph.DnaK:1:3 | T-Mt.AC145767v28-1:1:2 | 7.48 | 24.12 | 14.67 | 5.33 | 5.59 |
| EXP-BSAcVNV.FLT:1:2 | T-Gb.E6-3b:1:1 | 1.00 | 1.00 | 1.00 | 1.00 | 1.00 |
| EXP-BSAcVNV.FLT:1:2 | T-Mt.AC145767v28-1:1:2 | 19.34 | 3.32 | 5.32 | 8.07 | 5.78 |
| EXP-CERV.FLT:1:2 | T-Gb.E6-3b:1:1 | 1.00 | 1.00 | 1.00 | 1.00 | 1.00 |
| EXP-CERV.FLT:1:2 | T-Mt.AC145767v28-1:1:2 | 21.50 | 60.50 | 37.89 | 27.25 | 26.16 |
| EXP-DaMV.FLT:1:2 | T-Gb.E6-3b:1:1 | 1.00 | 1.00 | 1.00 | 1.00 | 1.00 |
| EXP-DaMV.FLT:1:2 | T-Mt.AC145767v28-1:1:2 | 26.84 | 15.76 | 1.53 | 4.33 | 6.26 |
| EXP-CUCme.eEF1a:1:1 | T-Gb.FbL2-1:1:1 | 1.00 | 1.00 | 1.00 | 1.00 | 1.00 |
| EXP-CUCme.eEF1a:1:1 | T-Mt.AC145767v28-1:1:2 | 5.14 | 6.47 | 3.60 | 8.56 | 4.56 |
| EXP-Mt.Ubq2:1:2 | T-Gb.FbL2-1:1:1 | | | 1.00 | 1.00 | 1.00 |
| EXP-Mt.Ubq2:1:2 | T-Mt.AC145767v28-1:1:2 | | | 0.62 | 1.51 | 4.86 |

As demonstrated in Tables 24 and 25, the *Medicago* 3' UTR T-Mt.AC145767v28-1:1:2 (SEQ ID NO: 1) boosted expression of the six constitutive EXP elements relative to T-Gb.E6-3b:1:1(SEQ ID NO: 40), but in different ways depending upon the specific EXP element and tissue. The EXP element, EXP-Mt.AC145767v28:1:1, when used to drive GUS and operably linked to its native 3' UTR T-Mt.AC145767v28-1:1:2 expressed very low in all of the tissues assayed and was undetectable in R3 Immature Seed, R3 Pod, and R1 Flower. Some tissues of plants comprising the EXP element EXP-Mt.Ubq2:1:2 and the 3' UTR T-Mt.AC145767v28-1:1:2 demonstrated reduced expression relative to the combination of EXP-Mt.Ubq2:1:2 and T-Gb-.FbL2-1:1:1. This reduced expression was seen in R3 Immature Seed, R1 Flower, and R1 Petiole while, in contrast, Vn5 Sink Leaf and R5 Cotyledon expression was enhanced greater than four-fold. There was no change in root expression (Vn5 Root) with EXP-Mt.Ubq2:1:2 and either 3' UTR.

The regulatory expression element groups EXP-CERV.FLT:1:2 and EXP-DaMV.FLT:1:2 provided the highest levels of expression. As demonstrated in Tables 26 and 27, these two EXPs were enhanced in all tissues with T-Mt.AC145767v28-1:1:2 relative to the same EXPs combined with T-Gb.E6-3b:1:1(SEQ ID NO: 40). The regulatory expression element group EXP-CERV.FLT:1:2 was enhanced 60.50-fold in the developing Yellow Pod Cotyledon and less so in the Yellow Pod Embryo (21.50-fold), while the regulatory expression element group EXP-DaMV.FLT:1:2 was enhanced to a greater degree in the Yellow Pod Embryo than in the Yellow Pod Cotyledon (26.80- vs. 15.76-fold enhancement, respectively). These expression and enhancement differences offer an opportunity to provide tailored expression of a transgene in the later stage developing seed. The regulatory expression element group EXP-BSAcVNV.FLT:1:2 expressed highest in the R3 Pod and Vn5 Root when combined with T-Gb.E6-3b:1:1 (see Tables 25 and 26). The expression of EXP-BSAcVNV.FLT:1:2 in these two tissues was enhanced dramatically when combined with T-Mt.AC145767v28-1:1:2, particularly in Vn5 Root. Further, the expression of EXP-BSAcVNV.FLT:1:2 was boosted 58.63-fold when combined with T-Mt.AC145767v28-1:1:2 relative to this same EXP combined with T-Gb.E6-3b:1:19 (SEQ ID NO: 40)

In sum, the *Medicago truncatula* 3' UTR T-Mt.AC145767v28-1:1:2 (SEQ ID NO: 1) enhanced expression of six different constitutive EXP elements which were derived from both plant and plant viral genomic DNA. In addition, this 3' UTR enhanced expression of the seed-preferred EXP element EXP-Gm.Sphas1:1:1 (SEQ ID NO: 54) relative to most of the other *Medicago*-derived ' UTRs. Accordingly, this 3' UTR is suited for providing enhanced expression of a promoter or combination of operably linked expression elements in a construct.

Example 7

Analysis of EXP-Mt.Ubq2:1:2 (SEQ ID NO: 31) in Stably Transformed Soybean Plants Soybean plants were transformed with vectors, specifically plasmid constructs, comprising the constitutive regulatory expression element group EXP-Mt.Ubq2:1:2 (SEQ ID NO: 31) operably linked to a GUS coding sequence. These transformed plants were then assayed for GUS expression in stably transformed soybean plants.

The plant vectors utilized in these experiments were built using cloning methods known in the art. The resulting vectors comprised a left border region from *A. tumefaciens*; a first transgene expression cassette for selection of transformed plant cells that confers resistance to the antibiotic spectinomycin (driven by the *Arabidopsis* Actin 7 promoter); a second transgene expression cassette used to assess the activity of EXP-Mt.Ubq2:1:2 (SEQ ID NO: 31) which comprised EXP-Mt.Ubq2:1:2 operably linked 5' to a coding sequence for β-glucuronidase (GUS) that possesses a processable intron (GUS-2, SEQ ID NO: 44) operably linked 5' to the 3' UTR T-Mt.AC145767v28-1:1:2 (SEQ ID NO: 1) derived from *Medicago truncatula*, or the 3' UTRs T-Gb.E6-3b:1:1 (SEQ ID NO: 40) or T-Gb.FbL2-1:1:1 (SEQ ID NO: 41) derived from *Gossypium barbadense*; and a right border region from *A. tumefaciens*.

The resulting vectors were used to transform soybean plants as described in Example 3. Tables 28 and 29 show the average quantitative GUS expression values assayed in various tissues and developmental time points for the stably transformed soybean plants.

TABLE 28

Average GUS expression in leaf, root and flower for stably transformed soybean plants comprising EXP-Mt.Ubq2:1:2 (SEQ ID NO: 31).

| Plasmid Construct | 3' UTR Description | Vn5 Root | Vn5 Sink Leaf | Vn5 Source Leaf | R1 Source Leaf | R1 Petiole | R1 Flower |
|---|---|---|---|---|---|---|---|
| pMON125840 | T-Gb.E6-3b:1:1 | 252.58 | 126.69 | 86.01 | 49.05 | 108.41 | 83.23 |
| pMON125841 | T-Gb.FbL2-1:1:1 | 800.93 | 202.73 | 275.48 | 143.6 | 1195.97 | 482.13 |
| pMON155502 | T-Mt.AC145767v28-1:1:2 | 855 | 293.68 | 1118.76 | 254.25 | 875.67 | 398.1 |

TABLE 29

Average GUS expression in pod and seed tissues for stably transformed soybean plants comprising EXP-Mt.Ubq2:1:2 (SEQ ID NO: 31).

| Plasmid Construct | 3' UTR Description | R3 Immature Seed | R3 Pod | R5 Cotyledon | Yellow Pod Embryo | Yellow Pod Cotyledon |
|---|---|---|---|---|---|---|
| pMON125840 | T-Gb.E6-3b:1:1 | 2.22 | 111.19 | 3.21 | 24.31 | 50.98 |
| pMON125841 | T-Gb.FbL2-1:1:1 | 400.15 | 875.75 | 72.66 | 129.84 | 83.45 |
| pMON155502 | T-Mt.AC145767v28-1:1:2 | 247.18 | 1324.98 | 352.81 | | |

As demonstrated in Tables 28 and 29, EXP-Mt.Ubq2:1:2 (SEQ ID NO: 31) is able to drive constitutive expression of a transcribable DNA molecule in stably transformed soybean plants. Further, different 3' UTRs affect the degree of expression in each tissue. For example, combining EXP-Mt.Ubq2:1:2 with T-Gb.E6-3b:1:1 resulted in lower expression in all of the tissues assayed than the other two 3' UTRs, T-Gb.FbL2-1:1:1 and T-Mt.AC145767v28-1:1:2. However, regardless of which 3' UTR was applied, EXP-Mt.Ubq2:1:2 provides medium-to-high constitutive expression, the degree of which can be modulated by a selection of which 3' UTR is operably linked to the EXP.

Example 8

Enhancers Derived from the Regulatory Elements

Enhancers may be derived from the promoter elements provided herein, such as SEQ ID NOs: 32 and 36. An enhancer element may be comprised of one or more cis-regulatory elements that, when operably linked 5' or 3' to a promoter element, or operably linked 5' or 3' to additional enhancer elements that are operably linked to a promoter, can enhance or modulate expression of a transcribable DNA molecule, or provide expression of a transcribable DNA molecule in a specific cell type or plant organ or at a particular time point in development or circadian rhythm. Enhancers are made by removing the TATA box or functionally similar elements and any downstream sequence that allow transcription to be initiated from the promoters or promoter fragments.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements maybe cloned, using methods known in the art, to be operably linked to one or more copies of the enhancer element which are operably linked 5' or 3' to a promoter element, or operably linked 5' or 3' to additional enhancer elements that are operably linked to a promoter. Further, enhancer elements can be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector maybe constructed using methods known in the art similar to the constructs described in the previous Examples in which the resulting plant expression vectors contain a left border region from *A. tumefaciens*; a first transgene selection cassette that confers resistance to an antibiotic or herbicide and is utilized for selection of transformed plant cells; and a second transgene cassette in which an enhancer element is operably linked to a promoter forming a chimeric promoter element, which is operably linked 5' to a leader element, which is operably linked 5' to a coding sequence for GUS that possesses a processable intron (GUS-2, SEQ ID NO: 44), operably linked to a 3' UTR such as T-Gb.E6-3b:1:1 or any of those described above from *Medicago truncatula*; and a right border region from *A. tumefaciens*.

GUS expression driven by a regulatory element comprising one or more enhancers maybe evaluated in stable or transient plant assays as described herein to determine the effects of the enhancer element on expression of a transcribable DNA molecule. Modifications to one or more enhancer elements or duplication of one or more enhancer elements maybe performed based upon empirical experimentation, and the resulting gene expression regulation that is observed using each regulatory element composition. Altering the relative positions of one or more enhancers in the resulting regulatory or chimeric regulatory elements may affect the transcriptional activity or specificity of the regulatory or chimeric regulatory element and is determined empirically to identify the best enhancers for the desired transgene expression profile within a plant.

Example 9

Analysis of the Effect of 3' UTRs on Constitutive GUS Expression in Stably Transformed Corn Plants Corn plants were transformed with binary plasmid constructs to assess the effect of the *Medicago* 3' UTR T-Mt.Oxr-1:2:1 (SEQ ID NO: 17) on expression relative to two 3' UTRs used frequently in corn plants. Specifically, the corn plants were transformed with vectors containing an EXP that exhibited a constitutive expression profile driving expression of the β-glucuronidase (GUS) transgene, which was operably linked to the *Medicago* 3' UTR T-Mt.Oxr-1:2:1 (SEQ ID NO: 17). These transformed corn plants were compared to transformed corn plants in which GUS was operably linked to either the 3' UTR T-AGRtu.nos-1:1:13 (SEQ ID NO: 49) or the 3' UTR T-Os.LTP:1 (SEQ ID NO: 56).

The binary plasmid constructs utilized in these experiments were built using cloning methods known in the art. The resulting vectors contained a right border region from *A. tumefaciens*; a first expression cassette to assay the 3' UTR sequence wherein a constitutive regulatory expression element group EXP-FMV.35S-enh+Ta.Lhcb1+Zm.DnaK:1:2 (SEQ ID NO: 56) is operably linked 5' to a coding sequence for GUS that possesses a processable intron (GUS-2, SEQ ID NO: 44), which is operably linked 5' to one of the following three 3' UTRs: T-Mt.Oxr-1:2:1 (SEQ ID NO: 17), T-AGRtu.nos-1:1:13 (SEQ ID NO: 49) or T-Os.LTP:1 (SEQ ID NO: 56); a second transgene expression cassette used for selection of transformed plant cells that confers resistance to the herbicide glyphosate (driven by the rice Actin 1 promoter); and a left border region from *A. tumefaciens*. The resulting plasmids were used to transform corn plants.

Histochemical GUS analysis was used for qualitative expression analysis of the transformed plants. Whole tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The $R_0$ plants were inspected for expression in the roots and leaves, as well as the anther, silk, and developing seed and embryo, 21 days after pollination (21 DAP).

Quantitative analysis for the transformed corn plants was also performed. For the quantitative analysis, total protein was extracted from selected tissues of the transformed corn plants. One microgram of total protein was used with the fluorogenic substrate 4-methyleumbelliferyl-β-D-glucuronide (MUG) in a total reaction volume of 50 µl. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence is measured with excitation at 365 nm, emission at 445 nm using a Fluoromax-3 (Horiba; Kyoto, Japan) with Micromax Reader, with slit width set at excitation 2 nm and emission 3 nm.

Table 30 shows the average quantitative GUS expression measured demonstrating different effects of each 3' UTR on the same constitutive expressing EXP.

TABLE 30

Average GUS expression in corn plants transformed with different 3' UTRs.

| | | Plasmid Construct | | |
| --- | --- | --- | --- | --- |
| Developmental Stage | Tissue | pMON128881 T-Mt.Oxr-1:2:1 (SEQ ID NO: 17) | pMON119693 T-Os.LTP:1 (SEQ ID NO: 56) | pMON132035 T-AGRtu.nos:13 (SEQ ID NO: 49) |
| V4 | Leaf | 205 | 232 | 222 |
|  | Root | 126 | 134 | 44 |
| V7 | Leaf | 277 | 534 | 293 |
|  | Root | nd | 135 | nd |
| VT | Leaf | 314 | 429 | 194 |
|  | Root | 198 | 1043 | 291 |
|  | Flower/Anther | 527 | 486 | 308 |
| R1 | Cob/Silk | 169 | 1258 | 319 |
| R3 | Embryo 21DAP | 179 | 72 | 101 |
|  | Endosperm 21DAP | 516 | 207 | 243 |

As can be seen in Table 30, each 3' UTR had a different effect on constitutive expression driven by EXP-FMV.35S-enh+Ta.Lhcb1+Zm.DnaK:1:2 (SEQ ID NO: 56). For example, the 3' UTR T-Os.LTP:1 (SEQ ID NO: 56) appeared to enhance expression in the VT Root and R1 Cob/Silk relative to the other two 3' UTRs. The 3' UTR T-Mt.Oxr-1:2:1 (SEQ ID NO: 17) appeared to enhance expression in the R3 seed, both in the 21DAP endosperm and 21DAP Embryo relative to T-AGRtu.nos-1:1:13 (SEQ ID NO: 49) and T-Os-.LTP:1 (SEQ ID NO: 56). Expression in the Flower/Anther was also higher using T-Mt.Oxr-1:2:1 (SEQ ID NO: 17) relative to the other two 3' UTRs. The differences in expression observed for each of the 3' UTRs demonstrates the usefulness of each 3' UTR in modulating expression. Thus, these experiments demonstrate that the selection of a 3' UTR can be used in transgene cassettes to fine tune expression of a particular transcribable DNA molecule. This experiment also demonstrates the ability of a dicot-derived 3' UTR, such as T-Mt.Oxr-1:2:1, to affect transcription in a monocot species such as corn.

Example 10

Analysis of Intron Enhancement of GUS Activity Using Plant Derived Protoplasts Generally, an intron is selected based upon experimentation and comparison with an intronless vector control to empirically select an intron and configuration within the vector transfer DNA (T-DNA) element arrangement for optimal expression of a transgene. For example, in the expression of an herbicide resistance gene, such as CP4 (U.S. RE39247), which confers tolerance to glyphosate, it is desirable to have transgene expression within the reproductive tissues as well as the vegetative tissues in order to prevent the loss of yield when applying the herbicide. An intron in this instance would be selected upon its ability, when operably linked to a constitutive promoter, to enhance expression of the herbicide resistance conferring transgene, particularly within the reproductive cells and tissues of the transgenic plant, and thus providing both vegetative and reproductive tolerance to the transgenic plant when sprayed with the herbicide. In most ubiquitin genes, the 5' UTR is comprised of a leader, which has an intron sequence embedded within it. The regulatory elements derived from such genes are therefore assayed using the entire 5' UTR comprising the promoter, leader, and intron. To achieve different expression profiles or to modulate the level of transgene expression, the intron from such a regulatory element may be removed or substituted with a heterologous intron.

The intron presented herein as SEQ ID NO: 34 was identified using genomic DNA contigs in comparison to expressed sequence tag clusters, or cDNA contigs, to identify exon and intron sequences within the genomic DNA. In addition, 5' UTR or leader sequences were also used to define the intron/exon splice junction of one or more introns under conditions when the gene sequence encodes a leader sequence that is interrupted by one or more introns. Introns were cloned using methods known in the art into a plant transformation vector to be operably linked 3' to a regulatory element and leader fragment and operably linked 5' to either a second leader fragment or to coding sequences, such as the expression cassettes presented in FIG. 1.

Thus, for example, a first possible expression cassette, such as Expression Cassette Configuration 1 in FIG. 1, is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible expression cassette, such as Expression Cassette Configuration 2 in FIG. 1, is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible expression cassette, such as Expression Cassette Configuration 3 in FIG. 1, is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Notably, Expression Cassette Configuration 3 is designed to allow splicing of the intron in such a manner as to produce a complete open reading frame without a frame shift between the first and second fragment of the coding sequence.

As discussed herein, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified.

Introns may be assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive EXP comprised of a promoter and leader such as EXP-CaMV.35S-enh+Ph.DnaK:1:3 (SEQ ID NO: 42), operably linked 5' to a test intron element (e.g. one SEQ ID NO: 34), operably linked to a coding sequence for GUS that possesses a processable intron (GUS-2, SEQ ID NO: 44), operably linked to the 3' UTR from (T-Gb.E6-3b:1:1, SEQ ID NO: 40). Protoplast cells derived from soybean or other genus plant tissue can be transformed with the base plant vector and Luciferase control vectors as described previously in Example 2 above, and assayed for activity. To compare the relative ability of the intron to enhance expression, GUS values are expressed as a ratio of GUS to Luciferase activity and compared with those levels imparted by a construct comprising the constitutive promoter operably linked to a known intron standard such as that as the intron derived from the *Nicotiana tabacum* elongation factor 4A10 gene, I-Nt.eIF4A10-1:1:1 (SEQ ID NO: 57), as well as a construct comprising the constitutive promoter, but without an intron operably linked to the promoter.

For stable plant assay of the intron presented as SEQ ID NO: 34, a GUS expression plant transformation vector can be constructed similar to the constructs described in the previous examples in which the resulting plant expression vectors contains a right border region from *A. tumefaciens*; a first expression cassette comprised of a constitutive EXP comprised of a promoter and leader such as EXP-CaMV.35S-enh+Ph.DnaK:1:3 (SEQ ID NO: 42), operably linked 5' to a test intron element (e.g., SEQ ID NO: 34), operably linked to a coding sequence for GUS that possesses a processable intron (GUS-2, SEQ ID NO: 44), operably linked to the 3' UTR from *Gossypium barbadense* (T-Gb.E6-3b:1:1, SEQ ID NO: 40). Protoplast cells derived from corn or other genus plant tissue may be transformed with the base plant vector and luciferase control vectors, as described previously in Example 2 above, and assayed for activity. To compare the relative ability of the intron to enhance expression, GUS values are expressed as a ratio of GUS to luciferase activity and compared with those levels imparted by a construct comprising the constitutive promoter operably linked to a known intron standard such as that as the intron derived from the *Nicotiana tabacum* elongation factor 4A10 gene, I-Nt.eIF4A10-1:1:1 (SEQ ID NO: 57), as well as a construct comprising the constitutive promoter, but without an intron operably linked to the promoter.

It should be noted that the intron presented as SEQ ID NO: 34 can be modified in a number of ways, such as deleting fragments within the intron sequence, which may reduce expression or duplication of fragments with the intron that may enhance expression. In addition, DNA sequences within the intron that may affect the specificity of expression to either particular cells types or tissues and organs can be duplicated or altered or deleted to affect expression and patterns of expression of the transgene. In addition, the intron provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron may be used to enhance expression of a transgene in stably transformed plants that can be of any genus monocot or dicot plant, so long as the intron provides enhancement of the transgene. The intron can also be used to enhance expression in other organisms, such as algae, fungi, or animal cells, so long as the intron provides enhancement or attenuation or specificity of expression of the transgene to which it is operably linked.

Having illustrated and described the principles of the invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
   a) a DNA sequence comprising SEQ ID NO:30; and
   b) a fragment comprising at least 200 contiguous nucleotides of SEQ ID NO:30, wherein the fragment has gene-regulatory activity;
   wherein said DNA sequence is operably linked to a heterologous transcribable DNA molecule.

2. The recombinant DNA molecule of claim 1, wherein said DNA sequence comprises SEQ ID NO:30.

3. The recombinant DNA molecule of claim 1, wherein the heterologous transcribable polynucleotide molecule comprises a gene of agronomic interest.

4. The recombinant DNA molecule of claim 3, wherein the gene of agronomic interest confers herbicide tolerance in plants.

5. The recombinant DNA molecule of claim 3, wherein the gene of agronomic interest confers pest resistance in plants.

6. A transgenic plant cell comprising a recombinant DNA molecule comprising a DNA sequence selected from the group consisting of:
   a) a DNA sequence comprising SEQ ID NO:30; and
   b) a fragment comprising at least 200 contiguous nucleotides of SEQ ID NO:30, wherein the fragment has gene-regulatory activity;
   wherein said DNA sequence is operably linked to a heterologous transcribable DNA molecule.

7. The transgenic plant cell of claim 6, wherein said transgenic plant cell is a monocotyledonous plant cell.

8. The transgenic plant cell of claim 6, wherein said transgenic plant cell is a dicotyledonous plant cell.

9. A transgenic plant, or part thereof, comprising a recombinant DNA molecule comprising a DNA sequence selected from the group consisting of:
   a) a DNA sequence comprising SEQ ID NO:30; and
   b) a fragment comprising at least 200 contiguous nucleotides of SEQ ID NO:30, wherein the fragment has gene-regulatory activity;
   wherein said DNA sequence is operably linked to a heterologous transcribable DNA molecule.

10. A progeny plant of the transgenic plant of claim 9, or a part thereof, wherein the progeny plant or part thereof comprises said recombinant DNA molecule.

11. A transgenic seed of the transgenic plant of claim 9 wherein the transgenic seed comprises the recombinant DNA molecule.

12. A method of producing a commodity product comprising obtaining a transgenic plant or part thereof according to claim 9 and producing the commodity product therefrom.

13. The method of claim 12, wherein the commodity product is protein concentrate, protein isolate, grain, starch, seeds, meal, flour, biomass, or seed oil.

14. A method of producing a transgenic plant comprising:
   a) transforming a plant cell with the recombinant DNA molecule of claim 1 to produce a transformed plant cell; and
   b) regenerating a transgenic plant from the transformed plant cell.

* * * * *

SEQUENCE LISTING

```
<160> NUMBER OF SEQ ID NOS: 57

<210> SEQ ID NO 1
<211> LENGTH: 500
<212> TYPE: DNA
<213> ORGANISM: Medicago truncatula

<400> SEQUENCE: 1
ttaatcatct gaaactgttc accatgcatg caatcttgtg aaatatatgg ttttaattag      60
acttcaatct tatgttggct attgtactaa taaaagcatg tcatgttatt ttcatttgat     120
tttatctgta ctttggtttg tttgaagaat aaagatgagc ttgctatgca tgcatgcatg     180
ccatcgatta tcagggtttc ctttttttctt ttctggcttc ccatcaattt ggtgtgaatt     240
agtgtgtgtg atatattata ttatgctatt tatgaaataa attgttggtt atatttgatc     300
tacaatctac atacatgtga tttttatcaa caaaatatct cgggaaacaa taccttttttg    360 gtagcaaaat tcaaataata ctattttaaa taaatcaaag ttaaccaata ccttattcaa     420
gttggagggg tctcaaacaa gcaaagaat tcaagttgtt aatgaacttc ggttaatgat      480
```

```
aaaagaattc gcatttaaaa                                                500
```

<210> SEQ ID NO 2
<211> LENGTH: 500
<212> TYPE: DNA
<213> ORGANISM: Medicago truncatula

<400> SEQUENCE: 2

```
aagggctctc tgtcatgatt tcatactttc attattgagc tctgtaatta caattatgac    60
catgagaaca tctcttattg tgtggccttt taattgctga tgttagtact gaaccaaagc   120
ttatcgtgat gatgtaaaag caataagtac ttgtttgtag cttctttgtg tctccctttg   180
ggcttaatac atctgtttag tgttgtggct ttggcataga cttctcttgg taataatgcc   240
ttgcaatgca aaatttcaat tatcaaattc tattatgttc tcaccttatg gtaacagctt   300
accctgtgga agatgagatt cttgagttga gtcattgcca attttggca ttagcttttg    360
aattagtgaa ttttgacaaa aattaccgtg acactgattt tgttgaagct cttaagtgta   420
gttttttacaa aatttcagtg gctcgttgtg attatgtcaa actcacggcg aatgtagttc   480
ttacagaatt tcagtggctc                                                500
```

<210> SEQ ID NO 3
<211> LENGTH: 500
<212> TYPE: DNA
<213> ORGANISM: Medicago truncatula

<400> SEQUENCE: 3

```
gcatgaataa tcaagctcat aaatttcatg gctttgaatt tgtactattt tggttactag    60
aaagtgtatt tgtgtgttta tgcagtaata aatctctaag agatatatgt ttgttatttt   120
ttataattat ccaaaaaatc gttaatgttg aaaattgatt caaaattgat attgaagttc   180
tgaaaaaatc gtggcgtgat taaaaatcca aacttttta taaaataata ttgtgtctat    240
atctttata aatgacgata aatgggataa agtaaatgaa acaaaaccgt taatgcaatg    300
ttcatctgca caatatatat aattaaaaaa cattataaaa ccttgtttct tcactcattt   360
acaatcttga aattttagtc tttaccattt gaaagtacaa tctttcatg aaagtttata    420
gtacaaatca agagtttgga taagctgctc tgctttttat aatcactggg aaatgattta   480
tgacttggaa aaacaacttg                                                500
```

<210> SEQ ID NO 4
<211> LENGTH: 500
<212> TYPE: DNA
<213> ORGANISM: Medicago truncatula

<400> SEQUENCE: 4

```
aaaattgttg ttgaattcca aaagggtcct gtagtagaaa tttacgtaca agcaaaatcg    60
atttcttgat atacaagtta aagggtatat gagaaaatac atacatgtaa atgagtaccg   120
agttttctat agtttgagca tttgtgtcaa ataagcaagt gattgtgatg attccaagct   180
tttaaattga aaaagattta gcaaccaaga atcaaacatc cacacaccat atacatgctc   240
taggcttcaa ataccattga gcaacattat actctatatt gtttgatttc aaccaattcc   300
aagagcttga taattcgcat gagaattata ttatatcaaa aactttagtg aaagatgctc   360
caataatttc taaacttgtg atcattttt ggcattagga ataaggcaaa aatctgcaaa    420
atgcaataag aaaaaactag ctcatgaata caaagaaaat gttactacaa ctgacatttt   480
```

```
caaaattcaa caataatctt                                                500
```

```
<210> SEQ ID NO 5
<211> LENGTH: 465
<212> TYPE: DNA
<213> ORGANISM: Medicago truncatula

<400> SEQUENCE: 5
ggagcagtgt gtggtgtttg agaggaatgg tgcatcttac ataaatttca cagacattgc     60
tcttattttg aatgcgggtt catcgacatt gggtagtttt tggatgtatt ttgctagaca    120
cgatgaacgt ggagtttgat tgttttctct attgttgatc ctctgttaaa taacattgtt    180
aagtgataat tcccagctat ttcggtttta ttattcccca atgttgctct tccgcatgtc    240
ccaaagtagt cttggagtt ctcgtctgcg tttaattgta ttggaagtaa attaacagca     300
tcacgactct ttcgtaatta gttactttca aagaattttt ttggcactaa acactaccct    360
gatggagtgt tcaattttaa acatgagaac ttataaaaga tttttaaaca tgagaactta    420
tcaaaaatat tatgaatgtt cgctcgatat gaagtaggca aggtt                    465
```

```
<210> SEQ ID NO 6
<211> LENGTH: 472
<212> TYPE: DNA
<213> ORGANISM: Medicago truncatula

<400> SEQUENCE: 6
tctaacacca tggttacttc ataagttgtt cctttttaat agtttgttat cttgtccgtg     60
tcttagtttt tgttattcc agttttattt ttccagtttt agaaacttac agaactgggt     120
tcttgatcgg cgatggtacc gttttggtt ttaattgtta agagtcttga aacttgaat     180 ttcaagggc agcttaaagg tttgacatct taattttgct gctgaggaat gttgtaattg    240 cattttatt acaagacagt tttgttatgt caaatcttat atttatcttt atggttatgt     300
ttttgaattt ttgttcgtaa tatttgtcct tgattgtgtg tttgtggttc cgtgcttgca    360 atttttacttg gaaagattgg ctttctgcag gttggtttta gcctgtttaa gctgtcatga    420
catgtttgat tagtgaattc cagagaacat gcctaattca tgtgcagcag ca            472
```

```
<210> SEQ ID NO 7
<211> LENGTH: 500
<212> TYPE: DNA
<213> ORGANISM: Medicago truncatula

<400> SEQUENCE: 7
aaataaaatt acttatagat agatttggaa ctagatgact agtgttttat tgtttctggt     60
ttgtgtaatt ctataaatta atgttatctc tatgtccaag aatgttatct ctagtgctct    120
ttgttgtact tggactgaaa ttatggggat tggatttatg tgcttttcat gactcgtcaa    180
taaatgaata aataaaatgt gacttttctc ctttacttgt tgtgtttggc ttctgatgta    240
ataagaaatc caatgaatct gctaatattc ttgtgagagt tttagtgata taataataat    300
cctaccgctt caaacatagt ttttgttttt aaaaaaaaaa aaaaaaacaa gggaaagtat    360
attaacaatc tcttagattt atcccagaat aattgaattt ttcatctatt atgcttagta    420
ctattaagta aagctagtga gaggggcatt ttatggctca tcactagagc atgtacaaaa    480
gaaattgttc tcgtgaattt                                                500
```

```
<210> SEQ ID NO 8
<211> LENGTH: 452
```

<212> TYPE: DNA
<213> ORGANISM: Medicago truncatula

<400> SEQUENCE: 8

```
tgagtcaaag ttggtgtctc ttttgaagac tagaaaaagg gtttattttg ttgttatttt      60
gagtattgtg gtttgacttg cgagacagaa taattggttg gagttttatc tttttgtttt     120
cttttttgttc ttttgataat ttcaggttca gtgtacttgg tccaacccga gcaaaagggt    180
tattataaaa cactatttcg aagtgaagtt cttttttcaa tttgaaatta tgtggcttca     240
tttacacatt agattctcat cctaaattaa tccgaaattg aatgttgttt taactaatgt     300
cttgaaaatt gagagtattt tctccagtat tctataggtt ttcttccgtt gaggcaaaat     360
atatgtttat gtgcatcaaa cataaatgtg agtatcattc ttagtcggga ttaaatagga     420
ctattgagtt tttgtgagca tagcttgttt gg                                   452
```

<210> SEQ ID NO 9
<211> LENGTH: 500
<212> TYPE: DNA
<213> ORGANISM: Medicago truncatula

<400> SEQUENCE: 9

```
tgagtcaaag ttggtgtctc ttttgaagac tagaaaaagg gtttattttg ttgttatttt      60
gagtattgtg gtttgacttg cgagacagaa taattggttg gagttttatc tttttgtttt     120
cttttttgttc ttttgataat ttcaggttca gtgtacttgg tccaacccga gcaaaagggt    180
tattataaaa cactatttcg aagtgaagtt cttttttcaa tttgaaatta tgtggcttca     240
tttacacatt agattctcat cctaaattaa tccgaaattg aatgttgttt taactaatgt     300
cttgaaaatt gagagtattt tctccagtat tctataggtt ttcttccgtt gaggcaaaat     360
atatgtttat gtgcatcaaa cataaatgtg agtatcattc ttagtcggga ttaaatagga     420
ctattgagtt tttgtgagca tagcttgttt ggcggagatt tgctgtata  taggggttaa    480
ttcttgtttg gaggagattt                                                500
```

<210> SEQ ID NO 10
<211> LENGTH: 500
<212> TYPE: DNA
<213> ORGANISM: Medicago truncatula

<400> SEQUENCE: 10

```
gctgtttcat tactgtggta gtgctataaa ttggcctact ttttgtttct tacagtctat      60
tagcctagca gccgttaggc ctcttttta aatgtaataa gttgaattcc tgaactcgtg      120
aagcttgccc cttattgaac cgtagtgttt ttggttgctt aataccatta agcaatgagt     180
tgttttggat ttatatgcat ttaccgaatt ttatttggat gatagtaagc gttttttcca     240
tgttcacaaa tatgccatga aaaagcagt aaaatttcaa taaccaaca tcatgataaa       300
acaaaagtat gcatcgtatg aaaaaaagtg ggtgatgaaa tgataagtct aattttggtc    360
gaatttggtc gttgttatttt ttgcatgaac atctcttttg tacaacctaa caacttattt    420
gctattttta atattttgt actgcttttg atttgcttgc tcttcacaat attatagtgt      480
tgcattagtt gttcaattt                                                 500
```

<210> SEQ ID NO 11
<211> LENGTH: 500
<212> TYPE: DNA
<213> ORGANISM: Medicago truncatula

<400> SEQUENCE: 11

```
tatctcaata tctcaacttc aattcatttg ttgcagtgct ttgcattgtt gtattatcag        60
tgaacatatt tatttatata acatgttcgt tattgttgat gcgggttgat tatgctagag       120
ctgaaactcg agcttgtact tatatatagt taccatatag ttacctatgt tgtatttgag       180
tgttgtttag agattgcaag ttttgttgga tcttgtgttc tctgcaaatg aagagtaata       240
ttttatgtag aataggtttg tgtgaattaa ttttttagaa tctggattta aactactgcg       300
atcaattgat ttaagcccct tggatagagat cagttgactc acatcgtgac ctcgacaaat      360
tgagtgtttt ttttcttctt tttcggatag aaaaatgtaa gttttgggaa gcagattttc       420
tgctgtaaca gcagggtgct gtaaagcatc cgagctgtcc ggtcagaatt gtacggccat       480
gatccgggtc tgctcaccaa                                                   500
```

<210> SEQ ID NO 12
<211> LENGTH: 500
<212> TYPE: DNA
<213> ORGANISM: Medicago truncatula

<400> SEQUENCE: 12

```
acacatattc aagctctatt actctgtttt taggttgaga atattgtgaa gtgtgttgtg        60
tgtgcgttct gtttttatgta aaagtaaatt ctgtgaatta tattttgtaa ggaataaatt      120
atgtaagaat ggtttaatta tctattgtct cacatcgttt tttatgtcta ttttaagtat       180
tggtattgta ttctatttat acacaagagt taataatagc ataacataaa ttccacaagg       240
atcaagtaaa ataatatcca catgaaacat ctaagaaagg aaaacaatat ggctcaattt       300
cctatctttc tttatttatg ttttagtcat cttttctttcc ctatttcttg ttgaaagcta      360
ataggagtat ggtactttct acgccatttt tttttaagta ctctcttta cacaatattt        420
tatcaaattg tagtgacatt ttatttacg atgcagttaa tgttcgttgt gttactgtca        480
atgattgtcc aaaggtgaaa                                                   500
```

<210> SEQ ID NO 13
<211> LENGTH: 500
<212> TYPE: DNA
<213> ORGANISM: Medicago truncatula

<400> SEQUENCE: 13

```
gaacgccaag acatggcggc tcttgagct gaatcttctg cttttatttg catttctgtt        60
gtatttaact cctatttca ccaatgtaac tacacaagca gaagaacctg tatgtggctg       120
attatatgtt agaaatatgg atcccaagaa atgtcaactc ttgtgcatga gttcagaata      180
tttattgggc tgtcttagtc atgttttaa ttaattttcc gtaacctata tctcttattt       240
tatgttaatt agtacaaaca agacaacaaa agacctaagc caaaaataaa atcatcaact      300
acttaaaggt aagaatgggt tcaaatcaat caggtcgtag gtaaccatgc acttggatgt     360
gtcaaatgag aagtaaaatt ttgtcactat accattgatc atttatgtgt tgtaaaaaaa     420
aattgttcct tttagcattg cacttgcaca aaaactcagt ttcatgtcga attcaaactt      480
gttattttct gtctgacaaa                                                   500
```

<210> SEQ ID NO 14
<211> LENGTH: 500
<212> TYPE: DNA
<213> ORGANISM: Medicago truncatula

<400> SEQUENCE: 14

```
gaaaactagt ggtttatttta ctatatgtta ttgtatcttt caataaagag atgctccatt      60
tgaccaaaaa taaaagaga tgctccagat agtgcatctt atctatgtta taataatcaa       120
gtgtatgcat ttccttcccc tttatttgga gcatgtgtat gtttaaatat ttgtaatttg      180
aaccttcaaa cttgttctag ttaccaaata ataagatcat tattagtttg tgtgtttatc      240
tctattgtct actaatttta ttttttttt acttttctat tctttatttg tattaaatca       300
taagttctaa ttatttaatc aaaacttcaa atggtggcgg ttatacgcta ttccgaatcg      360
tcttttgttg tccgagtcta taggctacac tcatatcctg gttgaaacag actctatagc     420
tgtcctgatc aggtcaatca gattagaaga ttcttttctc aaaattggag tcttttcttt      480
caacgctgtg cagattgact                                                  500

<210> SEQ ID NO 15
<211> LENGTH: 500
<212> TYPE: DNA
<213> ORGANISM: Medicago truncatula

<400> SEQUENCE: 15
aaaggttgaa ggaaagagaa tctcagcagt catattgaat ctgtttgatt tactacacaa      60
aaggataatt ttctattttg gatgtttcaa taactgtgtg caatatttag gtatttagta      120
tgctctgtga gcaaattaat cccccctccc aaaatttcat ttcacccccac ttttctgttt     180 ttccaaatgt ctctgtatcc gtggctctgc cacaatcttt attgatattg caattttcca      240
gttttgtgca ataatcatg agcatttcaa ttcactattt tcaaatgcgg ctttataccct     300 taaacacgag ggcatagctt cacactatgg tttccatgaa tattgtcaca ccgtggtttg     360
caaggatatt gtttaaaggt taaatgtgac tgtgaatgat caatattttg cagaaaagaa      420
ataaacttaa acaaaggtg atctaaattt tcaatgacca gtaatcaata tcttacaatc      480
tctcaactgt gaaattccga                                                  500

<210> SEQ ID NO 16
<211> LENGTH: 500
<212> TYPE: DNA
<213> ORGANISM: Medicago truncatula

<400> SEQUENCE: 16
tttgctttat atatgataag aaattgtttt tttagttttg ctttccattt gtaaaattat      60
cttttgagag ttttagatt attgcacttt ctaaattttc attttgcttc tttgttggat      120
ctgggatttc tgaaatgaac attagagtaa taatcgaat ctgagtatta caagcaagtt       180
tgttgaaata atgatctcta atttgtcaa gttaaagaaa tcaaatatc ttgtaccaaa        240 aaaaaaaaaa aatcaaaaca tcatgtttga ttaacaaaac tccaatttga aatcaattta      300
aatttaaatt tcattttag aaagaaaaaa aaatattat tccatccatt attagttctc        360
gatttcacac aactagtttt tcgatttact cacgtaccta catatgagta tgtaagggtt      420
gattacgtat tcattattgc tctttgtttc acataattct ttttttttcaa tcaaaatgaa    480 aattatataa aggagtacaa                                                  500

<210> SEQ ID NO 17
<211> LENGTH: 500
<212> TYPE: DNA
<213> ORGANISM: Medicago truncatula

<400> SEQUENCE: 17
```

```
aaatgaatga atcagctttc tcttgttcat aaagaattgt gtggaaatga attgtgtgtt      60
gctatataca tgagtgtgtt ggttgctgcc ttatgtgttc ttctagggtt atttttttctt   120 ttgctttgta ataatttgtg cgttactatt gtaaacaatg tatttaatga ataatgaaag    180
tctaaagttt gtaatggagg gaagtaaatg taaatccttt cgcaagtgtt tttttagctt    240
gaaagtcttt catgcattgg tttggagtac catcatatca cccttaattt ttctagttat    300
gattttaggg acaagagaag ttcaaattac actccaatta tgtgctcggg gaaatttaat    360
tggtagcaga caatacacga aaagtaaca  catttagtat cttactatca tctgcaaatc    420
gtgcatatgt tcatatcatt tcacattttt ataatccagc atattataaa ttcaaaccta    480
attttggtac ataatagtat                                                500
```

<210> SEQ ID NO 18
<211> LENGTH: 500
<212> TYPE: DNA
<213> ORGANISM: Medicago truncatula

<400> SEQUENCE: 18

```
ttaatccatc atcatcggca tgtgtgtttg tttttttttgt gtctattttg accaaatcat   60
atattcatat gtatgtgtaa attattatga actactgtat gttagtgctt catgttcgtg   120
aactgaacac attgaatggt ctgtggagtg tggagattct ttcatgttgt tatttattat   180 gagttttttct tttttattttc ttcaaaagca gactactgaa atattgattt gataccacca   240
aaaagaaaaa gtaatatatc ttactattaa tatttatagt tgatataaac atcatcaaaa   300
tttaaaatca gtttctaatc ttggtttgtt cggggtggcc cttggattcc attttgcata    360
tgctgttgcc caggaactaa gctctttcat aagataatgt tcggggtagc tctgttacta    420
ggtcataaaa aagaccgatt gttgtcatcg ttcgaaaaag cgaaaaaaca aacacaagca    480
ttctcgtcat aacaaagacc                                                500
```

<210> SEQ ID NO 19
<211> LENGTH: 500
<212> TYPE: DNA
<213> ORGANISM: Medicago truncatula

<400> SEQUENCE: 19

```
tgaagaagga taatgattga ttaattgttt aatataaagt tgagggaatt tttttatatt    60
ttctataaat tatcaaaata tgttgattgt tgagaataag aattctaggt tcaaaacaga    120
atcttgaatt gtcaaggagt ctgttaaatg tgagatttat tattatgttt catttcaaaa    180
gtattaagtt ttatttgtgt gactatttgg attgtgatta ttgctaaatg tttatacgta    240
ttaaaatttg catgcttttt gtcccactca aataaaaatt aattagtatt gcttgcttcc    300
aagttttaga tttactataa tatgtatttt tttttttttag agatacatgt aatatgtata    360 aatatttttgt aacgagcaaa aaaaatacac tctaattatc tcataataga gaaaagacac   420
tctttatgtg agtgtaaatt cctataaaga aaagagatgt gaaaactacc ctcagtatac    480
ggataattgc actcacaata                                                500
```

<210> SEQ ID NO 20
<211> LENGTH: 289
<212> TYPE: DNA
<213> ORGANISM: Medicago truncatula

<400> SEQUENCE: 20

```
gggtcttagt ttactttttct tgatttgtaa tgtacaatgg ggctgtggtg tttatatttc    60
```

| | |
|---|---|
| atttaatcgt taatgtacta ctttatacta gttgtttata tttaaaaaag cataaacttt | 120 |
| gcctcatcta aatgtacttg aattgagttt acttagaagt gcttgaattg agtttgtgta | 180 |
| aatgaacata attttagtag tgcttagatt aagttcacat atcactactt tataccaggg | 240 |
| gattactatt cttttagct tttgttttta ctgttggttt tttgccaaa | 289 |

<210> SEQ ID NO 21
<211> LENGTH: 382
<212> TYPE: DNA
<213> ORGANISM: Medicago truncatula

<400> SEQUENCE: 21

| | |
|---|---|
| gaagggtctt gatctatgaa gcacggaaac gcctccgatt aggcgtgtcc aggtgtccga | 60 |
| cacgtatcat ctctgatacc gacacgcac cgacacttac aattcacgg aattatgtaa | 120 |
| ttttctcaaa ttattagagg tgtcggcgtg tcagtgtacg tgtcgtgtcc tttgtatccg | 180 |
| tgtttcatag gtcttggttc attttttcttg atttgtaatg tacaatgggg ttgttgtgtt | 240 |
| taaatttcat ctaatcttta ctgtactatt ataaatatat atactagttt gttcataaaa | 300 |
| gcataaagtt ttgcttatct ctttggtgtt accggttcaa tgctcgacct aggaaaaaat | 360 |
| taataaaatt tcattcataa aa | 382 |

<210> SEQ ID NO 22
<211> LENGTH: 400
<212> TYPE: DNA
<213> ORGANISM: Medicago truncatula

<400> SEQUENCE: 22

| | |
|---|---|
| gcaaggagga tcatgaacat cacaaagtga atttatttta tgtttgcacc atatattatt | 60 |
| atttgtgaca cattttagaa ctcttaaacc attttttctgt ttgcattttta gctactggtt | 120 |
| gttgtattca cataatgat gcagtcctat gcttcttggt gtaagattca atactatgta | 180 |
| aagtgtatgt ctttggttgt atactatttta aaatctattc ttgtattgta taatttattt | 240 |
| tagcctttgt ttgagattga ggttacttgt tctgttgcat ttaatcacaa gttttcattt | 300 |
| tgttatacgt acgtgttata ccctgttttt ggacctaaaa atactgggcc caatttcatt | 360 |
| tcaaactttg tcaattatca aatttcaact gcacagttca | 400 |

<210> SEQ ID NO 23
<211> LENGTH: 699
<212> TYPE: DNA
<213> ORGANISM: Medicago truncatula

<400> SEQUENCE: 23

| | |
|---|---|
| actgcagtca cagtcataaa taccggtgca taacatgaat taattttata tttgcaacat | 60 |
| gttttaaaa tcttaaacct tctatttttc cactccatag gttatcaatt aagtattatt | 120 |
| attttgtgtg attctactac tttggaatat aagaagattg aaaaggaatt tctgtgagcc | 180 |
| ctatatataa accctaaacc ctatgtttat tgcctattgg tacccactgt actttgcggc | 240 |
| tgttgtgaag atcaagttat aattgctagg atagtttcta tttggttcat gttagttttc | 300 |
| aacaaagtga tttcaattat gttgtttgaa cactttaaac tagttattgg ttgttgtatt | 360 |
| cacaataatg atgtagttct atgcttcttg gtgcatgaac aaatactaca taaagtgtaa | 420 |
| gcccttggtt gtaattgtat tttaggaaat atttactatt ttgtaattga ttttagcctt | 480 |
| tgtttgagat tgagataaca tgtatttact ttcctttctc attttatcac aattcttcat | 540 |

```
cttttttttac attttggttt tatgaagagg actaaaaata tctctagtta cttaacttct    600
cttttgtagt aagaaaaata ctatgatcag aaacataaat caagcatctg ttacgaacgg    660
tatacttgga aaacaatat cattattaac aactttagt                            699
```

<210> SEQ ID NO 24
<211> LENGTH: 500
<212> TYPE: DNA
<213> ORGANISM: Medicago truncatula

<400> SEQUENCE: 24

```
aaacaccaat tccatcttct tcaataataa ccactatata tatatagaag caacttcaaa     60
aatacttaat acttgtatta taaattgagt tactttgaat gtcctacgat agagacggag    120
ttcaaatctc ctcaagtatg gttgaaaaat ggtcttcaat gtaactttaa ataaaaactt    180
tgtacgtcct cgctaataaa aataatgttt gtttaattac tttatatatg tattttttaa    240
tgctatttta tatatgttgt accccaaact tgtctgacca atttaatcag aagaacatgt    300
agagtgtagg tttgccggga agatttggat taaagtcttc gtttggttgg gtttggtctt    360
ggtcatgccg gaaaatttat tttccttgta cttcaaatgt tttgctttt cgatcggaaa    420 gggaatagga gattaaaggg cctccttta atatggcaaa cagaattata gctttagact    480
gacgctgcgg tttagcttca                                                500
```

<210> SEQ ID NO 25
<211> LENGTH: 500
<212> TYPE: DNA
<213> ORGANISM: Medicago truncatula

<400> SEQUENCE: 25

```
ttatggtagt agttttgaaa tgttgggaac ttgttttca tgttttgtta ccatctgttt      60
taaactatgt actgtctcca tctgacattt taataactcg atcctcgggt tattttagtt    120
ttcctattta ttactgcagt acttttgttt caattttgat ttagttgttt ccattatact    180
tccaattttg gtgttttatt ccttttctt aaaattttga tttattata cttccgcata    240 gtgttttttt tacattgcga ttctatttaa attattatgt ttttcattta ggtttacaat    300
tttggtttag ttgttcccat aatattttca ttgtttagtt gttcgcatag tgtttttac    360 atttatgttt ttcatttcct aaattaaatt gttaatttga gatgatgctt ttttgtgaac    420
aatgaaaaca ttcttgatat tttcattgtt tcaatgtctt gtataaatat tttcacatgt    480 tagaatttt atgttgttgg                                                 500
```

<210> SEQ ID NO 26
<211> LENGTH: 500
<212> TYPE: DNA
<213> ORGANISM: Medicago truncatula

<400> SEQUENCE: 26

```
gagtactctc aacatggac acaccatggg attgtgtaac ataataatg tgtcgtttgt      60 aatgaatgct cgcaactttt ctagctaatt aagctagagt tgaacttgag ctacttttat    120
gtaccctaaa gaggcacaat ctttgctgtt gatgtactat gatcatgtta taatatgatg    180
aaaatggagt gtgcctcatt ttataatttt tattttcctg agtatatgtt tttagggcta    240
aacaccttat aaaaaaggt cacttagaat atgaaacatg aacttttgta aaaaagtaga    300
gattaaaatt gaaatcaaaa attttttag gatcaatatt cgaagaattt ttttagaggg    360
attaaaatta aatatagttt cggactgacc caaggcacaa tccggctccg ctcgggttcg    420
```

```
acctgagtcc accatgcatc tgtcacctta ccattgacac gccctaaaat acattagatc    480
gcagtacaaa ttgagagtta                                                500

<210> SEQ ID NO 27
<211> LENGTH: 500
<212> TYPE: DNA
<213> ORGANISM: Medicago truncatula

<400> SEQUENCE: 27
caaattgtta gtgtttttct gatttagttc agagattgta agtaagatac cccaaaagtt     60
gtattatact atactattat agttagtaaa gcaatgtaat aactgtgcag gatgtcaaaa    120
gaaaagctag aaaaaatgat ttaaggggat atccggatat gagattgagt ccataggagc    180
acccacattc atgccaccca aatgagtggt ataaatggga cccacataat atattatatt    240
actttatact ttccaattat ttaaaccact caactacatt ttctaaatat ccataccact    300
cctctaaaac tctaaaatgg gtcccactta tcttacaact acaatatact ttaaattata    360
ttttaaatta atatataaaa tgtgtaatga aaatatataa aatgtatcac acaatatact    420
caaaatgaat caaatatata tgttaaaaaa attagccgtt gcatgagtga aaaaaaaaaa    480
atattaccgt tgcatgagtt                                                500

<210> SEQ ID NO 28
<211> LENGTH: 500
<212> TYPE: DNA
<213> ORGANISM: Medicago truncatula

<400> SEQUENCE: 28
tgaagaagga taatgattga ttaattgttt aatataaagt tgagggaatt tttttatatt     60
ttctataaat tatcaaaata tgttgattgt tgagaataag aattctaggt tcaaaacaga    120
atcttgaatt gtcaaggagt ctgttaaatg tgagatttat tattatgttt catttcaaaa    180
gtattaagtt ttatttgtgt gactatttgg attgtgatta ttgctaaatg tttatacgta    240
ttaaaatttg catgcttttt gtcccactca aataaaaatt aattagtatt gcttgcttcc    300
aagttttaga tttactataa tatgtatttt tttttttag agatacatgt aatatgtata    360 aatatttgt aacgagcaaa aaaaatacac tctaattatc tcataataga gaaaagacac    420
tctttatgtg agtgtaaatt cctataaaga aaagagatgt gaaaactacc ctcagtatac    480
ggataattgc actcacaata                                                500

<210> SEQ ID NO 29
<211> LENGTH: 481
<212> TYPE: DNA
<213> ORGANISM: Medicago truncatula

<400> SEQUENCE: 29
gcagctggaa acttactagt gttaaagttg tatctggctc atttcgagct gggtatatat     60
atatgtgatt gtggaatttc ttgtggtctg gaagtatttt caacagttgt gatgcagtat    120
tatggaattt atgacatgcg gtattatgga atttatgaca ttatgtggtg tttgcttcaa    180
taatatgtat caaaggagtt ttataagact tcatttaaca tttcagatgc ttggatgtgt    240
tactttatgt ttaccgtgct atgttttat accagattca agatttaga tgccttaggc    300 ttggaacaag ttttgattgt ttaacaatta aaaaggtttt atgacctaaa accatggatt    360
ttcctgattt ccgaaagttt taaaattatt tcaaataaaa tcatggatgt tggtttaagt    420
```

```
ggcgaagtct tctgctcttt cttttcaagt agagtaagat cttggattct agtcaccatg    480
a                                                                    481

<210> SEQ ID NO 30
<211> LENGTH: 600
<212> TYPE: DNA
<213> ORGANISM: Medicago truncatula

<400> SEQUENCE: 30
tcattcaatt tgaccctttt gctacattct tgctgtcata gttatttaat ttaatttctt     60
aaggtgcata ttcttttggt gaatttaagc cccccccgaaa catggaagga ggttggctgc   120
aaagttcctg aaggataatc gttttttttca ttcccttttaa ttttttgttat tcattatttc  180 acatttacc taaaacttca gggagtgaga taaagaactc tttctctctg aactgtttat    240
gttgtctact agaaaaaaaa atcctgtaag aggtaaggta ttcttccaaa acaggattct    300 tttttcttatc attttacttc attagttcct aagttccttt tcctacattg tataagattc   360
tgtcagtaca tttatgttgc ttatgtagga agtgggactg agtttcttat gaaggaattt    420
atgagttatt gaatatttat tgcaagctat attttagaat acagtatact ttcttcttat    480
gttattattt ttttaagtgt attgtgttgt gttattatta taagctttgt taaactctga    540
tcattttcaa attcaaaaca atgtttagtt caaaggcaaa gctgagttgt gctgattatt    600

<210> SEQ ID NO 31
<211> LENGTH: 1594
<212> TYPE: DNA
<213> ORGANISM: Medicago truncatula

<400> SEQUENCE: 31
actgttaata attttttaaac gtcagcgcac taaaaaaacg aaaagacgga cacgtgaaaa    60
taaaaaacac acactagttt atgacgcaat actattttac ttatgatttg ggtacattag    120
acaaaaccgt gaaagagatg tatcagctat gaaacctgta tacttcaata cagagacgta    180
ctcatatcgg atacgtacgc acgaagtatc atattaatta tttttaattt t taataaatat    240 tttatcggat acttatgtga tactctacat atacacaagg atatttctaa gatactttat    300
agatacgtat cctagaaaaa catgaagagt aaaaaagtga acaatgttg taaaaattca     360 ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttccttttaa tgatgtttct ctcaatatca catcatatga    540
aaatgtaata tgatttataa gaaaattttt aaaaaattta ttttaataat cacatgtact    600 atttttttaaa aattgtatct tttataataa tacaataata aagagtaatc agtgttaatt    660
tttcttcaaa tataagtttt attataaatc attgttaacg tatcataagt cattaccgta    720
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagc tgccgttggc gtaatataac    960
agccaatcga ttttttgctat aaaagcaaat caggtaaact aaacttcttc attctttttct  1020 tccccatcgc tacaaaaccg gttccttttgg aaaagagatt cattcaaacc tagcacccaa  1080
ttccgtttca aggtataatc tactttctat tcttcgatta ttttattatt attagctact   1140
atcgtttaat cgatcttttc ttttgatccg tcaaatttaa attcaattag ggttttgttc   1200
```

```
ttttctttca tctgattgaa atccttctga attgaaccgt ttacttgatt ttactgttta   1260
ttgtatgatt taatcctttg tttttcaaag acagtcttta gattgtgatt aggggttcat   1320 ataaatttt agatttggat ttttgtattg tatgattcaa aaaatacgtc ctttaattag    1380
attagtacat ggatattttt tacccgattt attgattgtc agggagaatt tgatgagcaa   1440 gttttttga tgtctgttgt aaattgaatt gattataatt gctgatctgc tgcttccagt    1500
tttcataacc catattcttt taaccttgtt gtacacacaa tgaaaaattg gtgattgatt   1560
catttgtttt tctttgtttt ggattataca gggt                              1594

<210> SEQ ID NO 32
<211> LENGTH: 1000
<212> TYPE: DNA
<213> ORGANISM: Medicago truncatula

<400> SEQUENCE: 32
actgttaata attttaaac gtcagcgcac taaaaaaacg aaaagacgga cacgtgaaaa     60 taaaaacac acactagttt atgacgcaat actatttac ttatgatttg ggtacattag    120
acaaaaccgt gaaagagatg tatcagctat gaaacctgta tacttcaata cagagacgta   180
ctcatatcgg atacgtacgc acgaagtatc atattaatta ttttaatttt taataaatat   240
tttatcggat acttatgtga tactctacat atacacaagg atatttctaa gatactttat   300
agatacgtat cctagaaaaa catgaagagt aaaaagtga caatgttg taaaaattca      360 ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttaa tgatgtttct ctcaatatca catcatatga    540
aaatgtaata tgatttataa gaaaattttt aaaaaattta ttttaataat cacatgtact    600
attttttaaa aattgtatct tttataataa tacaataata aagagtaatc agtgttaatt   660
tttcttcaaa tataagtttt attataaatc attgttaacg tatcataagt cattaccgta    720
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagc tgccgttggc gtaatataac    960
agccaatcga tttttgctat aaaagcaaat caggtaaact                         1000

<210> SEQ ID NO 33
<211> LENGTH: 92
<212> TYPE: DNA
<213> ORGANISM: Medicago truncatula

<400> SEQUENCE: 33
aaacttcttc attcttttct tccccatcgc tacaaaaccg gttcctttgg aaaagagatt    60
cattcaaacc tagcacccaa ttccgtttca ag                                  92

<210> SEQ ID NO 34
<211> LENGTH: 502
<212> TYPE: DNA
<213> ORGANISM: Medicago truncatula

<400> SEQUENCE: 34
gtataatcta ctttctattc ttcgattatt ttattattat tagctactat cgtttaatcg    60
```

```
atcttttctt ttgatccgtc aaatttaaat tcaattaggg ttttgttctt ttctttcatc    120
tgattgaaat ccttctgaat tgaaccgttt acttgatttt actgtttatt gtatgattta    180
atcctttgtt tttcaaagac agtctttaga ttgtgattag gggttcatat aaatttttag    240
atttggattt ttgtattgta tgattcaaaa aatacgtcct ttaattagat tagtacatgg    300 atattttta cccgatttat tgattgtcag ggagaaattg atgagcaagt ttttttgatg     360
tctgttgtaa attgaattga ttataattgc tgatctgctg cttccagttt tcataaccca    420 tattcttta accttgttgt acacacaatg aaaaattggt gattgattca tttgttttc     480 tttgttttgg attatacagg gt                                             502

<210> SEQ ID NO 35
<211> LENGTH: 1141
<212> TYPE: DNA
<213> ORGANISM: Medicago truncatula

<400> SEQUENCE: 35
tggattaatt tatttggact ggtttcgtaa tgagttgtat tcaatcattc tcttctttac     60
aattttgggt gaaagtggtc attgtatttt cttaaataac ttttttgctt atataaaaag    120
agagagaaaa aaagatcgtt tattgtctct actttgatta tagaatagaa gtttaagact    180
taatcaaacg ttataaaata ataaagatag taagtcttgc aaataaaata aaaaatgaga    240
gtgctgataa agccaaaacc ttacacaaat tgagggatta aaaagttact cacgtctatg    300
cataatcata cttacactca atattctcca ccaatgataa aatttgagga gttacttcaa    360
ctttagaaat taattttttt ttttgacaag actttagaaa ttaattatta tatattgagt    420
gtaatatgga ttaatcatat actaattcat tatatgcgtg actagtcaaa caagataaac    480
ctggatggta attgattgta atgcaccacc aacattgaat taaaaattag caagtttttt    540
tttgttggaa aaaattaaca agttaaatac caaaatgtga tttaattttt ttaatacgca    600
aattttaatg gttaatctgt taggaggaaa aattgtgaat tttttagtgc ataaatcaaa    660
ccgttgacct ttttattgaa ctcgtttagt ctcaactcat atcattggac tctaccttcg    720
agaatgtacc aaaatgtgtt tagttagacc tagcagggcc acataaatga actcgaacat    780 actttttcttg aaaaattgtt cttctcccat ttaaaattgc tcactccttt gatctatcgg    840
gagttaactc atactcggca ttattcaacg gtagctaacc cacattgtca ctgttagatt    900
agttcaatca ttttttaaat cgagtcaacc aatcttaaaa gtctcagcat gagttaacta    960
ccgctgaaaa atgtcgagcc cgagttaact tcatctgaat caagggaatg aacaatttta   1020 aagggagaa aagcaatttt cctttttcttg aactcattaa ggttccaaat tcttttataa    1080
aagggccact acactgcttt catatataca ccattcatac atagaaacca atagccaaaa   1140
a                                                                   1141

<210> SEQ ID NO 36
<211> LENGTH: 1107
<212> TYPE: DNA
<213> ORGANISM: Medicago truncatula

<400> SEQUENCE: 36
tggattaatt tatttggact ggtttcgtaa tgagttgtat tcaatcattc tcttctttac     60
aattttgggt gaaagtggtc attgtatttt cttaaataac ttttttgctt atataaaaag    120
agagagaaaa aaagatcgtt tattgtctct actttgatta tagaatagaa gtttaagact    180
taatcaaacg ttataaaata ataaagatag taagtcttgc aaataaaata aaaaatgaga    240
```

```
gtgctgataa agccaaaacc ttacacaaat tgagggatta aaaagttact cacgtctatg    300
cataatcata cttacactca atattctcca ccaatgataa aatttgagga gttacttcaa    360
ctttagaaat taatttttt ttttgacaag actttagaaa ttaattatta tatattgagt    420
gtaatatgga ttaatcatat actaattcat tatatgcgtg actagtcaaa caagataaac    480
ctggatggta attgattgta atgcaccacc acattgaat taaaaattag caagttttt    540 tttgttggaa aaaattaaca agttaaatac caaaatgtga tttaattttt ttaatacgca    600
aattttaatg gttaatctgt taggaggaaa aattgtgaat ttttagtgc ataaatcaaa    660 ccgttgacct ttttattgaa ctcgtttagt ctcaactcat atcattggac tctaccttcg    720
agaatgtacc aaaatgtgtt tagttagacc tagcagggcc acataaatga actcgaacat    780
acttttcttg aaaaattgtt cttctcccat ttaaaattgc tcactccttt gatctatcgg    840
gagttaactc atactcggca ttattcaacg gtagctaacc cacattgtca ctgttagatt    900
agttcaatca ttttttaaat cgagtcaacc aatcttaaaa gtctcagcat gagttaacta    960
ccgctgaaaa atgtcgagcc cgagttaact tcatctgaat caagggaatg aacaattta   1020 aaagggagaa aagcaatttt ccttttcttg aactcattaa ggttccaaat tctttataa   1080 aagggccact acactgcttt catatat                                      1107

<210> SEQ ID NO 37
<211> LENGTH: 34
<212> TYPE: DNA
<213> ORGANISM: Medicago truncatula

<400> SEQUENCE: 37
acaccattca tacatagaaa ccaatagcca aaaa                                34

<210> SEQ ID NO 38
<211> LENGTH: 298
<212> TYPE: DNA
<213> ORGANISM: Gossypium hirsutum

<400> SEQUENCE: 38
tgtcgtacag tatttctaca tttgatgtgt gatttgtgaa gaacatcaaa caaaacaagc     60
actggcttta atatgatgat aagtattatg gtaattaatt aattggcaaa acaacaatg    120 aagctaaaat tttatttatt gagccttgcg gttactttct tgtgatgatc tttttattt    180 tctaattata tatagtttcc ttcgctttga aatgctaaag gtttgagaga gttatgttct    240
ttttctcttc ctctttcttt tttaactta tcaaacaatt tttgaataaa aatgtgag      298

<210> SEQ ID NO 39
<211> LENGTH: 436
<212> TYPE: DNA
<213> ORGANISM: Gossypium barbadense

<400> SEQUENCE: 39
aacaaaagag tgcctcacat ttgatgcaat agctctgtaa tgtttcattc atttgcttat     60
ttcggccttg tttttctcgt attctatggg ctgatgtctc atatgggact tttctactag    120
agagcctacg ttactttacc attatattgt attctttgag acattattat tattttta    180 ccttttgagg acactctttt tttgtatttg aaggaattta ttgtttattt tgtttggaat    240
atgtttggtt ggattattc gattcatata tattatataa aagtaattat gttattaaga    300
aacgtagtaa gaacttacaa atataaggat cgaatcccga acttcatgca aatcaattta    360
```

```
caacccacac aagtttaaca ttaaattaac gtgattggtt agtaaattca tgtttctctg    420
tttaatttgt tgaatt                                                   436

<210> SEQ ID NO 40
<211> LENGTH: 315
<212> TYPE: DNA
<213> ORGANISM: Gossypium barbadense

<400> SEQUENCE: 40
tgatcacctg tcgtacagta tttctacatt tgatgtgtga tttgtgaaga acatcaaaca    60
aaacaagcac tggctttaat atgatgataa gtattatggt aattaattaa ttggcaaaaa   120
caacaatgaa gctaaaattt tatttattga gccttgcggt taatttcttg tgatgatctt   180
tttttttatt ttctaattat atatagtttc ctttgctttg aaatgctaaa ggtttgagag   240
agttatgctc tttttttctt cctctttctt ttttaacttt atcatacaaa ttttgaataa   300
aaatgtgagt acatt                                                   315

<210> SEQ ID NO 41
<211> LENGTH: 315
<212> TYPE: DNA
<213> ORGANISM: Gossypium barbadense

<400> SEQUENCE: 41
accatatgac actggtgcat gtgccatcat catgcagtaa tttcatggta tatcttaatt    60
atatggttaa taaaaaaaag atggtgagtg aataatgtgc gtgcattcct ccatgcacca   120
atggtgaatc tctttgcata catagagatt ctgaatgatt atagtttatg ttgtagtgaa   180
attaattttg aatgttgttt ttaaattta atgtcacttg gcttgattta tgttttaacg    240
aagcttatgt tatgtatttt actttaatga tattgcatgt attgttaatt taacattgct   300
tgatcagtat actct                                                   315

<210> SEQ ID NO 42
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression
      element group or EXP.

<400> SEQUENCE: 42
ggtccgatgt gagacttttc aacaaagggt aatatccgga aacctcctcg gattccattg    60
cccagctatc tgtcacttta ttgtgaagat agtggaaaag gaaggtggct cctacaaatg   120
ccatcattgc gataaaggaa aggccatcgt tgaagatgcc tctgccgaca gtggtcccaa   180
agatggaccc ccacccacga ggagcatcgt ggaaaaagaa gacgttccaa ccacgtcttc   240
aaagcaagtg gattgatgtg atggtccgat tgagactttt caacaaaggg taatatccgg   300
aaacctcctc ggattccatt gcccagctat ctgtcacttt attgtgaaga tagtggaaaa   360
ggaaggtggc tcctacaaat gccatcattg cgataaagga aaggccatcg ttgaagatgc   420
ctctgccgac agtggtccca agatggaccc ccacccacg aggagcatcg tggaaaaaga   480
agacgttcca accacgtctt caaagcaagt ggattgatgt gatatctcca ctgacgtaag   540
ggatgacgca caatcccact atccttcgca agacccttcc tctatataag gaagttcatt   600
tcatttggag aggacactct agacagaaaa atttgctaca ttgtttcaca aacttcaaat   660
```

```
attattcatt tatttgtcag ctttcaaact ctttgtttct tgtttgttga tt          712
```

<210> SEQ ID NO 43
<211> LENGTH: 613
<212> TYPE: DNA
<213> ORGANISM: Artificial sequence
<220> FEATURE:
<221> NAME/KEY: misc_feature
<222> LOCATION: (1)..(613)
<223> OTHER INFORMATION: Enhanced Cauliflower mosaic virus 35S promoter.

<400> SEQUENCE: 43

```
ggtccgatgt gagactttc aacaaagggt aatatccgga aacctcctcg gattccattg    60
cccagctatc tgtcactta ttgtgaagat agtggaaaag aaggtggct cctacaaatg    120 ccatcattgc gataaaggaa aggccatcgt tgaagatgcc tctgccgaca gtggtcccaa   180
agatggaccc ccacccacga ggagcatcgt ggaaaaagaa gacgttccaa ccacgtcttc   240
aaagcaagtg gattgatgtg atggtccgat tgagactttt caacaaaggg taatatccgg   300
aaacctcctc ggattccatt gcccagctat ctgtcacttt attgtgaaga tagtggaaaa   360
ggaaggtggc tcctacaaat gccatcattg cgataaagga aaggccatcg ttgaagatgc   420
ctctgccgac agtggtccca agatggaccc ccacccacg aggagcatcg tggaaaaaga   480
agacgttcca accacgtctt caaagcaagt ggattgatgt gatatctcca ctgacgtaag   540
ggatgacgca caatcccact atccttcgca agacccttcc tctatataag gaagttcatt   600
tcatttggag agg                                                    613
```

<210> SEQ ID NO 44
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Native E. coli GUS coding sequence with
      processable intron.

<400> SEQUENCE: 44

```
atggtccgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa   120
gaaagccggg caattgctgt gccaggcagt tttaacgatc agttcgccga tgcagatatt   180
cgtaattatg cgggcaacgt ctggtatcag cgcgaagtct ttataccgaa aggttgggca   240
ggccagcgta tcgtgctgcg tttcgatgcg gtcactcatt acggcaaagt gtgggtcaat   300
aatcaggaag tgatggagca tcagggcggc tatacgccat ttgaagccga tgtcacgccg   360
tatgttattg ccgggaaaag tgtacgtaag tttctgcttc tacctttgat atatataaa    420 taattatcat taattagtag taatataata tttcaaatat ttttttcaaa ataaagaat    480 gtagtatata gcaattgctt ttctgtagtt tataagtgtg tatattttaa tttataactt   540
ttctaatata tgaccaaaat tgttgatgt gcaggtatca ccgtttgtgt gaacaacgaa    600
ctgaactggc agactatccc gccgggaatg gtgattaccg acgaaaacgg caagaaaaag   660
cagtcttact ccatgatttt cttaactat gccggaatcc atcgcagcgt aatgctctac   720
accacgccga cacctgggt ggacgatatc accgtggtga cgcatgtcgc gcaagactgt   780
aaccacgcgt ctgttgactg gcaggtggtg gccaatggtg atgtcagcgt tgaactgcgt   840
gatgcggatc aacaggtggt tgcaactgga caaggcacta gcgggacttt tcaagtggtg   900
```

```
aatccgcacc tctggcaacc gggtgaaggt tatctctatg aactgtgcgt cacagccaaa      960
agccagacag agtgtgatat ctacccgctt cgcgtcggca tccggtcagt ggcagtgaag     1020
ggcgaacagt tcctgattaa ccacaaaccg ttctacttta ctggctttgg tcgtcatgaa     1080
gatgcggact tgcgtggcaa aggattcgat aacgtgctga tggtgcacga ccacgcatta     1140
atggactgga ttggggccaa ctcctaccgt acctcgcatt acccttacgc tgaagagatg     1200
ctcgactggg cagatgaaca tggcatcgtg gtgattgatg aaactgctgc tgtcggcttt     1260
aacctctctt taggcattgg tttcgaagcg ggcaacaagc cgaaagaact gtacagcgaa     1320
gaggcagtca acggggaaac tcagcaagcg cacttacagg cgattaaaga gctgatagcg     1380
cgtgacaaaa accacccaag cgtggtgatg tggagtattg ccaacgaacc ggatacccgt     1440
ccgcaaggtg cacgggaata tttcgcgcca ctggcggaag caacgcgtaa actcgacccg     1500
acgcgtccga tcacctgcgt caatgtaatg ttctgcgacg ctcacaccga taccatcagc     1560
gatctctttg atgtgctgtg cctgaaccgt tattacggat ggtatgtcca aagcggcgat     1620
ttggaaacgg cagagaaggt actggaaaaa gaacttctgg cctggcagga gaaactgcat     1680
cagccgatta tcatcaccga atacggcgtg gatacgttag ccgggctgca ctcaatgtac     1740
accgacatgt ggagtgaaga gtatcagtgt gcatggctgg atatgtatca ccgcgtcttt     1800
gatcgcgtca gcgccgtcgt cggtgaacag gtatggaatt cgccgatttt gcgacctcg     1860
caaggcatat tgcgcgttgg cggtaacaag aaagggatct tcactcgcga ccgcaaaccg     1920
aagtcggcgg ctttctctgct gcaaaaacgc tggactggca tgaacttcgg tgaaaaaccg     1980
cagcagggag gcaaacaatg a                                                2001

<210> SEQ ID NO 45
<211> LENGTH: 1653
<212> TYPE: DNA
<213> ORGANISM: Photinus pyralis

<400> SEQUENCE: 45
atggaagacg ccaaaaacat aaagaaaggc ccggcgccat tctatcctct agaggatgga      60
accgctggag agcaactgca taaggctatg aagagatacg cctggttcc tggaacaatt      120
gcttttacag atgcacatat cgaggtgaac atcacgtacg cggaatactt cgaaatgtcc      180
gttcggttgg cagaagctat gaaacgatat gggctgaata caaatcacag aatcgtcgta      240
tgcagtgaaa actctcttca attctttatg ccggtgttgg gcgcgttatt tatcggagtt      300
gcagttgcgc ccgcgaacga catttataat gaacgtgaat tgctcaacag tatgaacatt      360
tcgcagccta ccgtagtgtt tgtttccaaa aagggggttgc aaaaaatttt gaacgtgcaa      420
aaaaaattac caataatcca gaaaattatt atcatggatt ctaaaacgga ttaccaggga      480
tttcagtcga tgtacacgtt cgtcacatct catctacctc ccggttttaa tgaatacgat      540
tttgtaccag agtcctttga tcgtgacaaa acaattgcac tgataatgaa ttcctctgga      600
tctactgggt tacctaaggg tgtggccctt ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg atatttgat atgtggattt      780
cgagtcgtct taatgtatag atttgaagaa gagctgtttt tacgatccct tcaggattac      840
aaaattcaaa gtgcgttgct agtaccaacc ctattttcat tcttcgccaa aagcactctg      900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
```

```
gggctcactg agactacatc agctattctg attacacccg aggggggatga taaaccgggc    1080 gcggtcggta aagttgttcc atttttgaa gcgaaggttg tggatctgga taccgggaaa    1140
acgctgggcg ttaatcagag aggcgaatta tgtgtcagag acctatgat tatgtccggt    1200 tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aagtcttac cggaaaactc gacgcaagaa aaatcagaga gatcctcata    1620
aaggccaaga agggcggaaa gtccaaattg taa                                 1653

<210> SEQ ID NO 46
<211> LENGTH: 936
<212> TYPE: DNA
<213> ORGANISM: Renilla reniformis

<400> SEQUENCE: 46
atggcttcca agtgtacga ccccgagcaa cgcaaacgca tgatcactgg gcctcagtgg      60
tgggctcgct gcaagcaaat gaacgtgctg gactccttca tcaactacta tgattccgag    120
aagcacgccg agaacgccgt gatttttctg catggtaacg ctgcctccag ctacctgtgg    180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360 tgggggggctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca cgctattgt cgaggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cagtaa                              936

<210> SEQ ID NO 47
<211> LENGTH: 1446
<212> TYPE: DNA
<213> ORGANISM: Artificial sequence
<220> FEATURE:
<221> NAME/KEY: misc_feature
<222> LOCATION: (1)..(1446)
<223> OTHER INFORMATION: Chimeric transcriptional regulatory expression
      element group or EXP.

<400> SEQUENCE: 47
ggtccgattg agactttca acaaagggta atatccggaa acctcctcgg attccattgc       60
ccagctatct gtcactttat tgtgaagata gtggaaaagg aaggtggctc ctacaaatgc     120
```

```
catcattgcg ataaaggaaa ggccatcgtt gaagatgcct ctgccgacag tggtcccaaa      180
gatggacccc cacccacgag gagcatcgtg aaaaagaag acgttccaac cacgtcttca      240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacgctg acaagctgac tctagcagat ctaccgtctt cggtacgcgc    660
tcactccgcc ctctgccttt gttactgcca cgtttctctg aatgctctct tgtgtggtga    720
ttgctgagag tggtttagct ggatctagaa ttacactctg aaatcgtgtt ctgcctgtgc    780
tgattacttg ccgtcctttg tagcagcaaa atatagggac atggtagtac gaaacgaaga   840
tagaacctac acagcaatac gagaaatgtg taatttggtg cttagcggta tttatttaag   900
cacatgttgg tgttataggg cacttggatt cagaagtttg ctgttaattt aggcacaggc  960
ttcatactac atgggtcaat agtatagga ttcatattat aggcgatact ataataattt    1020
gttcgtctgc agagcttatt atttgccaaa attagatatt cctattctgt ttttgtttgt   1080
gtgctgttaa attgttaacg cctgaaggaa taaatataaa tgacgaaatt ttgatgttta   1140
tctctgctcc tttattgtga ccataagtca agatcagatg cacttgtttt aaatattgtt   1200
gtctgaagaa ataagtactg acagtatttt gatgcattga tctgcttgtt tgttgtaaca    1260
aaatttaaaa ataaagagtt tccttttgt tgctctcctt acctcctgat ggtatctagt    1320
atctaccaac tgacactata ttgcttctct ttacatacgt atcttgctcg atgccttctc   1380
cctagtgttg accagtgtta ctcacatagt ctttgctcat ttcattgtaa tgcagatacc   1440
aagcgg                                                                1446
```

<210> SEQ ID NO 48
<211> LENGTH: 675
<212> TYPE: DNA
<213> ORGANISM: Artificial sequence
<220> FEATURE:
<221> NAME/KEY: misc_feature
<222> LOCATION: (1)..(675)
<223> OTHER INFORMATION: Chimeric transcriptional regulatory expression
      element group or EXP.

<400> SEQUENCE: 48

```
ggtccgatgt gagacttttc aacaaagggt aatatccgga aacctcctcg gattccattg       60
cccagctatc tgtcacttta ttgtgaagat agtggaaaag gaaggtggct cctacaaatg     120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc   240
aaagcaagtg gattgatgtg atggtccgat gtgagacttt tcaacaaagg gtaatatccg   300
gaaacctcct cggattccat tgcccagcta tctgtcactt tattgtgaag atagtggaaa   360
aggaaggtgg ctcctacaaa tgccatcatt gcgataaagg aaaggccatc gttgaagatg   420
cctctgccga cagtggtccc aaagatggac ccccacccac gaggagcatc gtggaaaaag   480
aagacgttcc aaccacgtct tcaaagcaag tggattgatg tgatatctcc actgacgtaa   540
gggatgacgc acaatcccac tatccttcgc aagacccttc ctctatataa ggaagttcat   600
```

```
ttcatttgga gaggaaccat cttccacaca ctcaagccac actattggag aacacacagg    660
gacaacacac cataa                                                    675

<210> SEQ ID NO 49
<211> LENGTH: 253
<212> TYPE: DNA
<213> ORGANISM: Agrobacterium tumefaciens

<400> SEQUENCE: 49
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggttttatg attagagtcc cgcaattata catttaatac     180
gcgatagaaa acaaaatata gcgcgcaaac taggataaat tatcgcgcgc ggtgtcatct    240
atgttactag atc                                                      253

<210> SEQ ID NO 50
<211> LENGTH: 841
<212> TYPE: DNA
<213> ORGANISM: Glycine max

<400> SEQUENCE: 50
ggcaaaaaca tttaatacgt attatttaag aaaaaaatat gtaataatat atttatattt     60
taatatctat tcttatgtat tttttaaaaa tctattatat attgatcaac taaaatattt    120
ttatatctac acttattttg catttttatc aattttcttg cgtttttggg catatttaat    180
aatgactatt ctttaataat caatcattat tcttacatgg tacatattgt tggaaccata    240
tgaagtgtcc attgcatttg actatgtgga tagtgttttg atccaggcct ccatttgccg    300
cttattaatt aatttggtaa cagtccgtac taatcagtta cttatccttc ctccatcata    360
attaatcttg gtagtctcga atgccacaac actgactagt ctcttggatc ataagaaaaa    420
gccaaggaac aaaagaagac aaaacacaat gagagtatcc tttgcatagc aatgtctaag    480
ttcataaaat tcaaacaaaa acgcaatcac acacagtgga catcacttat ccactagctg    540
atcaggatcg ccgcgtcaag aaaaaaaaac tggaccccaa aagccatgca caacaacacg    600
tactcacaaa ggtgtcaatc gagcagccca aaacattcac caactcaacc catcatgagc    660
ccacacattt gttgtttcta acccaacctc aaactcgtat tctcttccgc cacctcattt    720
ttgtttattt caacacccgt caaactgcat gccaccccgt ggccaaatgt ccatgcatgt    780
taacaagacc tatgactata aatatctgca atctcggccc aggttttcat catcaagaac    840
c                                                                   841

<210> SEQ ID NO 51
<211> LENGTH: 422
<212> TYPE: DNA
<213> ORGANISM: Dahlia mosaic virus

<400> SEQUENCE: 51
atcaacggag aaacaaagat aaaaatcaat tactcacatg aaagagtatt gatcacgagt     60
cactatggag cgacaatctc cagacaggat gtcagcatct tatcttcctt tgaagaaagc    120
atcatcaata acgatgtaat ggtggggaca tccactaagt tattgctctg caaacagctc    180
aaaaagctac tggccgacaa tcataattgc tcggcatgtg caggtgggc ctccactagc     240 aataatacaa gctttacagc ttgcagtgac tcatcctcca ataatggaga aaaagacgtc    300
```

```
agcagtgacg aacaagggtc gaaagacttg cctatataag ggcattctcc cctcagttga    360
agatcatcga agttggagc aataaactct ctcttcaaca aatctatctt ttatctttta    420
tc                                                                   422

<210> SEQ ID NO 52
<211> LENGTH: 595
<212> TYPE: DNA
<213> ORGANISM: Banana streak virus strain Acuminata Vietnam

<400> SEQUENCE: 52
agacatcctg gaccaatatg ctgaagatta tgctacctac accaggatag gacttgaagc     60
acttaacctt gaagattggt tcgaagaacc agaacccgat ccacctaacc ctgtggaccg    120
ccagaggata gaggacatcc tggacctact gaacgtcagc aatgacgact gaaagattcc    180
caggacaccg gcggaagtgg tggacccagt ctaggtgcga tgcttagtcg cgcacgatga    240
ctatgtcgga aggcatcttt gctttcggca aactttagta atactttaag gaaagtattg    300
tacaagttag gtgcagagac aataatgcac ccagctttag ctttgtttat ggaattattg    360
tgtcggttgc attattggat gcctgcgtgc accctaagca atccccggcc ctcttctcta    420
taagaggagc ccttgcaatc agttgcaagc attcaagttt cccactgcaa gcttacttct    480
gagtttgagt tcaagttcaa taaaattcaa gctttcctct tacattctgt tcttgaaagg    540
ttcgatctaa tcgagcgagt agagaacaag atctttggg atttccgccg ttcca         595

<210> SEQ ID NO 53
<211> LENGTH: 382
<212> TYPE: DNA
<213> ORGANISM: Carnation etched ring virus

<400> SEQUENCE: 53
atcctcaact tccaatcaga agttagcagc tgcaagcttt taggattcca tagtgataag     60
atatgttctt atctaaacaa aaaagcaagc gtcggcaaac catacagctg tccacaaaaa    120
ggaaaggctg taataacaag cggacccagc ttctcagtgg aagatacttt atcagacact    180
gaataatgga tggaccctac cacgattaaa gaggagcgtc tgtctaaagt aaagtagatg    240 cgtcttttaat aattcatcta ctttagacgt catgcatgac gtttaacatg cattgtatcc    300
agatcctccc tggctatata aagggagtta aatttcattg ttaaggcatc gaaaaaaaaa    360
tttcaagtct atctctcaag aa                                             382

<210> SEQ ID NO 54
<211> LENGTH: 1235
<212> TYPE: DNA
<213> ORGANISM: Cucumis melo

<400> SEQUENCE: 54 aaatttaat aattaaaatg aacaatttt caagagtaat agagtttgag agatgtcaga     60
gaagtttgag gaagaagata acaagtggga gaagagaata agtttgttgt gtgaaagaga    120
aggggaaatt tcattcaagg gtatattgaa cttttactc aaattttgta agtctatttt    180
ttccgatcaa tcctaaatc acacacaccc ttaaaaatg gattatattt ggcaattttc    240
catgataaac tcatttttaa tttagagtta ttttttcaac gagatattaa cagttttagt    300
tcatatacta attgtaagaa tagttctctt taagttgaat agaattttg aaacttttaa    360 tagttcaaaa ggtattttg aaacaaata agaatgtttt tgaactttt ataaaaagaa    420 ttgagatttt tttgaaattt ttgataaaga gaaaagaaaa gaagaaagaa aaaagaaaaa    480
```

```
caagtttgta gaactccgtg ggaaaatcgt cgagggccct gtgaaggaat tttgaaatta      540
taatgagggt attttcgtca acaagggaat ttagacatcg tatataagca tcctcaaacc      600
ctataattaa gcccttcaat ccaattgcca ttctccatct ctcgccgcaa gggtttaaga      660
gcagcttctc tcctcaggtt gggggtttccc cctatcttct tcattcttcc tcttctcgat     720
ttctttcttc tatttgctcg atagtctctt atttcttgag cttttgctgt ttttctcctg      780
tacatcctaa catgaattat aacttggttt tgattttgtc ttttacttct gtattaaaca      840
acttttctta ccctttattt cttctcttct tcttcgtgtc cctgcccttt tgttttttatg     900 ctaatttat gtttctgttt atcaatctat cgaggcgtga cctgtcgttc ttccaatagc       960
gtagatctgc acttaatcta ttctagctga ttggattggt cgttttcgt ttttttaatt      1020 tattttctct gttctagttc cgataaattt ttttatatat aattaacaag ttctccagcc     1080
aaaagggtta atattgcgtt ggatattta atttttacgt tatttagatg tgtgaatcta      1140
ataaaattag ggttattcat aaatttcagt aatgatattt tggttatctg ttcttgctgt     1200
tcctgtttcg cagttctttt acctaatatt caagc                                1235
```

<210> SEQ ID NO 55
<211> LENGTH: 1865
<212> TYPE: DNA
<213> ORGANISM: Artificial sequence
<220> FEATURE:
<221> NAME/KEY: misc_feature
<222> LOCATION: (1)..(1865)
<223> OTHER INFORMATION: Chimeric transcriptional regulatory expression
      element group or EXP.

<400> SEQUENCE: 55

```
aattctcagt ccaaagcctc aacaaggtca gggtacagag tctccaaacc attagccaaa       60
agctacagga gatcaatgaa gaatcttcaa tcaaagtaaa ctactgttcc agcacatgca      120
tcatggtcag taagtttcag aaaaagacat ccaccgaaga cttaaagtta gtgggcatct      180
ttgaaagtaa tcttgtcaac atcgagcagc tggcttgtgg ggaccagaca aaaaaggaat      240
ggtgcagaat tgttaggcgc acctaccaaa agcatctttg cctttattgc aaagataaag      300
cagattcctc tagtacaagt ggggaacaaa ataacgtgga aaagagctgt cctgacagcc      360
cactcactaa tgcgtatgac gaacgcagtg acgaccacaa agaattagc ttgagctcag       420 gatttagcag cattccagat tgggttcaat caacaaggta cgagccatat cactttattc      480
aaattggtat cgccaaaacc aagaaggaac tcccatcctc aaaggtttgt aaggaagaat      540
tctcagtcca aagcctcaac aaggtcaggg tacagagtct ccaaaccatt agccaaaagc      600
tacaggagat caatgaagaa tcttcaatca agtaaacta ctgttccagc acatgcatca       660
tggtcagtaa gtttcagaaa aagacatcca ccgaagactt aaagttagtg gcatctttg      720 aaagtaatct tgtcaacatc gagcagctgg cttgtgggga ccagacaaaa aaggaatggt      780
gcagaattgt taggcgcacc taccaaaagc atctttgcct ttattgcaaa gataaagcag      840
attcctctag tacaagtggg gaacaaaata acgtggaaaa gagctgtcct gacagcccac      900
tcactaatgc gtatgacgaa cgcagtgacg accacaaaag aattccctct atataagaag      960
gcattcattc ccatttgaag gatcatcaga tacaaccatc ttccacacac tcaagccaca     1020
```

```
ctattggaga acacacaggg acaacacacc ataacggacc gaccgtcttc ggtacgcgct    1080
cactccgccc tctgcctttg ttactgccac gtttctctga atgctctctt gtgtggtgat    1140
tgctgagagt ggtttagctg gatctagaat tacactctga aatcgtgttc tgcctgtgct    1200
gattacttgc cgtcctttgt agcagcaaaa tataggggaca tggtagtacg aaacgaagat    1260
agaacctaca cagcaatacg agaaatgtgt aatttggtgc ttagcggtat ttatttaagc    1320
acatgttggt gttatagggc acttggattc agaagtttgc tgttaattta ggcacaggct    1380
tcatactaca tgggtcaata gtatagggat tcatattata ggcgatacta ataatatttg    1440
ttcgtctgca gagcttatta tttgccaaaa ttagatattc ctattctgtt tttgtttgtg    1500
tgctgttaaa ttgttaacgc ctgaaggaat aaatataaat gacgaaattt tgatgtttat    1560
ctctgctcct ttattgtgac cataagtcaa gatcagatgc acttgtttta aatattgttg    1620
tctgaagaaa taagtactga cagtattttg atgcattgat ctgcttgttt gttgtaacaa    1680
aatttaaaaa taaagagttt ccttttttgtt gctctcctta cctcctgatg gtatctagta    1740
tctaccaact gacactatat tgcttctctt tacatacgta tcttgctcga tgccttctcc    1800
ctagtgttga ccagtgttac tcacatagtc tttgctcatt tcattgtaat gcagatacca    1860
agcgg                                                                1865

<210> SEQ ID NO 56
<211> LENGTH: 300
<212> TYPE: DNA
<213> ORGANISM: Oryza sativa

<400> SEQUENCE: 56
attaatcgat cctccgatcc cttaattacc ataccattac accatgcatc aatatccata      60
tatatataaa cccttttcgca cgtacttata ctatgttttg tcatacatat atatgtgtcg    120
aacgatcgat ctatcactga tatgatatga ttgatccatc agcctgatct ctgtatcttg    180
ttatttgtat accgtcaaat aaaagtttct tccacttgtg ttaataatta gctactctca    240
tctcatgaac cctatatata actagtttaa tttgctgtca attgaacatg atgatcgatg    300

<210> SEQ ID NO 57
<211> LENGTH: 892
<212> TYPE: DNA
<213> ORGANISM: Nicotiana tabacum

<400> SEQUENCE: 57
gttagctatg ttttttttcc ctttaatatt ttaatgtatt tcttgtaata tttgtttgtg      60
tattgaagat tgaatcttga tgattgattg ttggtctgac tacagctggg ttttgtgtta    120
tgtaactatt tttaactatt ttggatagag gtctgtttga tgtgatgttc ttgattataa    180
aaataccatc ctactttgtt atctcatatc tggttggaac atgagcaatt tcatttctcc    240
tagttcttga attaaaaacc tgaaagtatt gtgcaaaaag atgctaggaa tgagactatc    300
attgttttga tgcaatatgt tcttttaagt aataggtgtt ttgtaagaag tctacgcagt    360
tctggatgta ttttactact cgggaaaact ggatagttgg atacttatta tgtataggaa    420
gtaaatgtgg ggattataat gcctttctct gccatctgct ctttgtattt tgtgtaaagc    480
ttggcatgcc tctcgtcaga tagccatcgc taccgtacat tcttttaaga atgaagcact    540
tagacacttg ctcgtttctg ccttttgtcac attgacccag catcatataa tctgaaagat    600
tggttagcag ttggctgcta tttaacttgt atgttaaaac aattgatttt catgtgtatc    660
tcctcctttt gtgctttgtg cttcttcata aaagaaagaa aacatacatt cggttgtgct    720
```

```
ctcctcctttt ttcaatggta gagaggaaga acagataatt ttattgctgc tgtaggtatt    780
tgacatctgt gatattttca tagtaaggtt ttgtttttc cttttattt agttcaagat       840 tgtttcatga atttccataa gcgtaatacc atagttcttt tatttgctac ag            892
```